(12) United States Patent
Chen

(10) Patent No.: US 11,390,685 B2
(45) Date of Patent: Jul. 19, 2022

(54) ERBB2 ANTIBODIES AND USES THEREFORE

(71) Applicant: Biosion, Inc., Nanjing (CN)

(72) Inventor: Mingjiu Chen, Nanjing (CN)

(73) Assignee: BIOSION, INC., Nanjing (CN)

( * ) Notice: Subject to any disclaimer, the term of this patent is extended or adjusted under 35 U.S.C. 154(b) by 121 days.

(21) Appl. No.: 16/475,770

(22) PCT Filed: Jan. 4, 2018

(86) PCT No.: PCT/IB2018/000078
§ 371 (c)(1),
(2) Date: Jul. 3, 2019

(87) PCT Pub. No.: WO2018/127791
PCT Pub. Date: Jul. 12, 2018

(65) Prior Publication Data
US 2020/0002434 A1    Jan. 2, 2020

Related U.S. Application Data

(60) Provisional application No. 62/443,078, filed on Jan. 6, 2017.

(51) Int. Cl.
*C07K 16/32* (2006.01)
*A61K 47/68* (2017.01)
*A61P 35/00* (2006.01)
*A61K 39/00* (2006.01)

(52) U.S. Cl.
CPC .......... *C07K 16/32* (2013.01); *A61K 47/6849* (2017.08); *A61P 35/00* (2018.01); *A61K 2039/505* (2013.01); *A61K 2039/507* (2013.01); *C07K 2317/24* (2013.01); *C07K 2317/33* (2013.01); *C07K 2317/73* (2013.01); *C07K 2317/76* (2013.01); *C07K 2317/77* (2013.01); *C07K 2317/92* (2013.01)

(58) Field of Classification Search
CPC ............... C07K 16/32; C07K 2317/33; A61K 47/6849; A61K 2039/505
See application file for complete search history.

(56) References Cited

U.S. PATENT DOCUMENTS

| | | |
|---|---|---|
| 4,676,980 A | 6/1987 | Segal et al. |
| 4,816,397 A | 3/1989 | Boss et al. |
| 4,816,567 A | 3/1989 | Cabilly et al. |
| 5,225,539 A | 7/1993 | Winter |
| 5,530,101 A | 6/1996 | Queen et al. |
| 5,565,332 A | 10/1996 | Hoogenboom et al. |
| 5,571,894 A | 11/1996 | Wels et al. |
| 5,585,089 A | 12/1996 | Queen et al. |
| 5,587,458 A | 12/1996 | King et al. |
| 5,693,762 A | 12/1997 | Queen et al. |
| 5,714,352 A | 2/1998 | Jakobovits |
| 5,723,323 A | 3/1998 | Kauffman et al. |
| 5,731,168 A | 3/1998 | Carter et al. |
| 5,763,192 A | 6/1998 | Kauffman et al. |
| 5,766,886 A | 6/1998 | Studnicka et al. |
| 5,807,715 A | 9/1998 | Morrison et al. |
| 5,814,476 A | 9/1998 | Kauffman et al. |
| 5,817,483 A | 10/1998 | Kauffman et al. |
| 5,821,337 A | 10/1998 | Carter et al. |
| 5,824,514 A | 10/1998 | Kauffman et al. |
| 5,837,234 A | 11/1998 | Gentile et al. |
| 5,976,862 A | 11/1999 | Kauffman et al. |
| 6,180,370 B1 | 1/2001 | Queen et al. |
| 6,204,023 B1 | 3/2001 | Robinson et al. |
| 7,371,376 B1 | 5/2008 | Fendly |
| 2007/0020261 A1 | 1/2007 | Sliwkowski et al. |
| 2016/0053011 A1 | 2/2016 | Lee et al. |
| 2017/0037146 A1 | 2/2017 | Zhou et al. |

FOREIGN PATENT DOCUMENTS

| | | |
|---|---|---|
| CN | 105164160 A | 12/2015 |
| CN | 105985435 A | 10/2016 |
| EP | 0239400 A2 | 9/1987 |
| EP | 0308936 A2 | 9/1988 |
| EP | 0519596 A1 | 12/1992 |

(Continued)

OTHER PUBLICATIONS

Hu, S. et al., "Epitope mapping and structural analysis of an anti-ErbB2 antibody A21: Molecular basis for tumor inhibitory mechanism," vol. 70(3), Feb. 15, 2008, pp. 938-949, XP055006703, Proteins: Structure, Function, and Bioinformatics.
Pedersen, M.W. et al., "Targeting three distinct HER2 domains with a recombinant antibody mixture overcomes trastuzumab resistance," vol. 14(3), Jan. 22, 2015, pp. 669-680, XP055267284, Molecular Cancer Therapeutics.
Extended European Search Report for European Application No. 18 736 067.2, dated Sep. 7, 2020, 11 pages.
Arteaga et al., Cancer Research 54, 3758-3765, Jul. 15, 1994.
Baselga et al., J. Clin. Oncol. 28:1138-1144, 2010.

(Continued)

*Primary Examiner* — Peter J Reddig
*Assistant Examiner* — Cheng Lu
(74) *Attorney, Agent, or Firm* — Duane Morris LLP; Thomas J Kowalski; Deborah L. Lu

(57) ABSTRACT

Provided is binding protein comprising an antigen binding fragment that specifically binds receptor tyrosine-protein kinase ErbB-2 (ErbB2), polynucleotides encoding the binding protein, vectors comprising the polynucleotides, pharmaceutical composition comprising the binding protein as well as methods of using the binding protein. The binding protein can be used for treating a disease or disorder, in which an ErbB2 activity is detrimental or inhibiting growth of ErbB2 positive cells or tumors synergistically with another ErbB2 antibody such as Trastuzumab. The binding protein can also be used for enhancing internalization of an agent or another ErbB2 antibody, for example, Trastuzumab, into ErbB2 positive cells.

18 Claims, 5 Drawing Sheets

Specification includes a Sequence Listing.

(56) References Cited

FOREIGN PATENT DOCUMENTS

| | | |
|---|---|---|
| EP | 0592106 A1 | 4/1994 |
| JP | 2013-529904 A | 7/2013 |
| JP | 2016-501234 A | 1/2016 |
| WO | 9014424 A1 | 11/1990 |
| WO | 9014430 A1 | 11/1990 |
| WO | 9014443 A1 | 11/1990 |
| WO | 9100360 A1 | 1/1991 |
| WO | 9109967 A1 | 7/1991 |
| WO | 9201047 A1 | 1/1992 |
| WO | 9203461 A1 | 3/1992 |
| WO | 9211272 A1 | 7/1992 |
| WO | 9220373 A1 | 11/1992 |
| WO | 9306213 A1 | 4/1993 |
| WO | 9308829 A1 | 5/1993 |
| WO | 9316185 A2 | 8/1993 |
| WO | 9404690 A1 | 3/1994 |
| WO | 9418219 A1 | 8/1994 |
| WO | 9616673 A1 | 6/1996 |
| WO | 9720032 A1 | 6/1997 |
| WO | 9802463 A1 | 1/1998 |
| WO | 9906834 A2 | 2/1999 |
| WO | 0100245 A2 | 1/2001 |
| WO | 2011147986 A1 | 12/2011 |
| WO | 2014089127 A1 | 6/2014 |
| WO | 2016205531 A3 | 12/2016 |

OTHER PUBLICATIONS

Carter et al., Proc. Natl. Acad. Sci. USA, vol. 89, pp. 4285-4289, May 1992.
Chothia et al., J. Mol. Biol. 227, 799-817, 1992.
Drebin et al., Proc. Natl. Acad. Sci. USA, vol. 83, pp. 9129-9133, Dec. 1986.
Holliger et al., Proc. Natl. Acad. Sci. USA, vol. 90, pp. 6444-6448, Jul. 1993.
Hudziak et al., Molecular and Cellular Biology, pp. 1165-1172, Mar. 1989.
International Preliminary Report on Patentability on Application No. PCT/IB2018/000078, dated Jul. 9, 2019—10 pages.
International Search Report and Written Opinion for International Application PCT/IB2018/000078, dated Jul. 11, 2018—15 pages.
King et al., Cancer Research 49, 4185-4191, Aug. 1, 1989.
Köhler et al., J. Immunol., 174:2453-2455, 2005.
Konecny et al., Breast Cancer Research and Treatment 67, 223-233, 2001.
Morrison et al., Proc. Natl. Acad. Sci. USA, vol. 81, pp. 6851-6855, Nov. 1984.
Morrison et al., Science, New Series, vol. 229, No. 4719, pp. 1202-1207, Sep. 20, 1985.
Pegram et al., Journal of the National Cancer Institute, vol. 96, No. 10, pp. 739-749, May 19, 2004.
Roguska et al., Proc. Natl. Acad. Sci. USA, vol. 91, pp. 969-973, Feb. 1994.
Rubin et al., Annals of Oncology 12 (Suppl. 1):S3-S8, 2001.
Shalaby et al., J. Exp. Med., The Rockefeller University Press, vol. 175, pp. 217-225, Jan. 1992.
Slamon et al., N. Engl. J. Med., vol. 344, No. 11, pp. 783-792, Mar. 15, 2001.
Stancovski et al., Proc. Natl. Acad. Sci. USA, vol. 88, pp. 8691-8695, Oct. 1991.
Traunecker et al., The EMBO Journal, vol. 10, No. 12, pp. 3655-3659, 1991.
Tutt et al., J. Immunol., 161:3176-3185, 1998.
Urlaub et al. Proc. Natl. Acad. Sci. USA, vol. 77, No. 7, pp. 4216-4220, Jul. 1980.
Akiyama et al., Arch Biochem Biophys 245, 531-536, (1986).
Baselga et al., J Clin Oncol 14, 737-744 (1996).
Beeram et al., Cancer 118, 5733-5740 (2007).
Ben-Kasus et al., Molecular Oncology 1, 42-54 (2007).
Brennan et al., Science, 229:81 (1985).
Chothia et al., J Mol Biol 196:901-917 (1987).
Chou, T., Pharmacol Rev 58:621-681 (2006).
Citri et al., Nature Reviews Molecular Cell Biology 7, 505-516 (2006).
Cobleigh et al., Clin Oncol 17: 2639-2648 (1999).
Gillies et al., J Immunol Methods 125:191-202 (1989).
Gruber et al., J Immunol, 152:5368-74 (1994).
Jones et al., Nature, 321:522-525 (1986).
Kabat et al., Ann NY Acad Sci, 190:382-391 (1971).
Kaufman et al., J. Mol Biol, 159: 601-621 (1982).
Koeppen et al., Histopathology 38, 96-104 (2001).
Kostelny et al., J Immunol, 148(5):1547-1553 (1992).
Lewis et al., Immmol Immunother: 37, 255-263 (1993).
Marmor et al., Int J Radiat Oncol Biol Phys 58, 903-913, (2004).
Munro, A., Nature, vol. 306, Dec. 1983, pp. 537-538 (1983).
Neuberger et al, Nature, 312:604-608 (1984).
Padlen, Molecular Immunology, 28(4/5):489-498 (1991).
Pegram et al., Oncogene 18:2241-2551 (1999).
Presta et al, J. Immunol, 151:2623-2632 (1993).
Riechmann et al, Nature, 332:323-327 (1988).
Schrama et al., Nature Reviews/Drug Discovery 5:147-159 (2006).
Sims et al., J. Immunol., 151(4):2296-2308 (1993).
Slamon et al., Science 235: 177-182 (1987).
Studnicka et al., Protein Engineering, 7(6):805-814 (1994).
Takeda et al., Nature, 314:452-454 (1985).
Verhoeyen et al., Science, 239:1534-1536 (1988).
Wahl et al., J Nucl Med 24:316-325 (1983).
Wu et al., Nature Biotechnology 34(2):137-138 (2016).
Harlow et al., Antibodies: A Laboratory Manual, second edition, (Cold Spring Harbor Laboratory Press, Cold Spring Harbor (1988), 43 pages.
Kabat et al., Sequences of Proteins of Immunological Interest, Fifth Edition, U.S. Department of Health and Human Services, NIH Publication No. 91-3242 (1991).
Plückthun, Pharmacology of Monoclonal Antibodies, vol. 113, Rosenburg and Moore eds., Springer-Verlag, New York, pp. 269-315 (1994).
Suresh et al., Methods in Enzymology, 121:210-228 (1986).
Milstein et al., Nature, vol. 305, Oct. 6, 1983, pp. 537-540 (1983).
JPO, Notice of Reasons for Rejection for the counterpart Japanese application, dated Nov. 2, 2021.
Mikkel W. Pedersen et al., Targeting three distinct HER2 domains with a recombinant antibody mixture overcomes trastuzumab resistance, Molecular Cancer Therapeutics, Mar. 2015, vol. 14, Issue 3, pp. 669-680.

A.

B.

C.

D.

E.

A.

B.

A.

B.

ERBB2 ANTIBODIES AND USES THEREFORE

CROSS-REFERENCE TO RELATED APPLICATION

This application is a U.S. national phase application of International Application No. PCT/IB2018/000078, filed Jan. 4, 2018, claiming priority to U.S. Provisional Application No. 62/443,078, filed Jan. 6, 2017, the entire disclosure of each of which is incorporated herein by reference in its entirety for all purposes.

SEQUENCE STATEMENT

The Sequence Listing for this application is labeled "SubstitutedSequenceListing" which was created on Jul. 2, 2019, amended on Nov. 19, 2021, and is 69.6 KB. The entire content of the sequence listing is incorporated herein by reference in its entirety.

FIELD OF THE INVENTION

The present invention relates generally to ErbB2 antibodies and uses thereof, either alone or in combination with other ErbB2 antibodies (e.g., Trastuzumab) in, for example, human cancer therapies.

BACKGROUND OF THE INVENTION

Receptor tyrosine-protein kinase ErbB-2 (ErbB2) is a member of the epidermal growth factor receptor (EGFR) family, which also includes EGFR, ErbB3 and ErbB4 (Akiyama et al., Arch Biochem Biophys 245, 531-6 (1986); Rubin and Yarden, Ann Oncol. 12 Suppl 1: S3-82001 (2001)). ErbB2 is also frequently called human epidermal growth factor receptor 2 (HER2), and used interchangeably in scientific literature. Each of these four receptors contains an extracellular ligand binding domain, a transmembrane domain, and an intracellular domain, which comprises a tyrosine kinase domain and whose C-terminus interacts with a multitude of signaling molecules, and exhibits both ligand-dependent and ligand-independent bioactivities (Marmor et al., Int J Radiat Oncol Biol Phys 58, 903-13 (2004)). HER2 hetero-dimerizes with any of EGFR members, i.e., EGFR, ErbB3 and ErbB4, and is considered a preferred dimerization partner of the other ErbB receptors. Upon being trans-activated, ErbB2 activates several downstream signaling cascades, including Ras-mitogen-activated protein kinase (MAPK) and PI3K-mTOR cascades, to promote cell proliferation and evade apoptosis (reviewed in Citri et al., Nat Rev Mol Cell Biol 7: 505-16 (2006)). ErbB2 is moderately expressed in normal adult tissues, where it regulates cell growth and differentiation. Gene amplification and overexpression of the ErbB2 protein have been reported in 20-30% of breast cancer, gastric cancer and ovarian cancer (King et al, Cancer Res 49: 4185-91 (1989); Slamon et al., Science 235: 177-82 (1987); Koeppen et al, Histopathology 38, 96-104 (2001)). In general, erbB2 gene amplification correlates to greater metastatic potential and poor prognosis. Since its expression is at relatively low level in normal tissues, ErbB2 is an attractive target for targeted therapies (Drebin et al., Proc Natl Acad Sci USA 83: 9129-33 (1986)).

Trastuzumab (CAS 180288-69-1, HERCEPTIN® Genentech) is a recombinant humanized monoclonal antibody version of a murine HER2 antibody that selectively binds to the human ErbB2 extracellular domain with a high affinity in a cell-based assay (Kd=5 nM) (Carter et al., Proc Natl Acad Sci USA 89: 4285-9 (1992)). Trastuzumab has been shown, in both in vitro assays and in mouse xenograft tumor models, to inhibit proliferation of human tumor cells that overexpress ErbB2 (Hudziak et al., Mol Cell Biol 9, 1165-1172 (1989); Lewis et al., Immunol Immunother 37, 255-263 (1993)). Besides direct effect on tumor cells, several mechanisms of action have been proposed, including immune mechanisms, such as antibody-dependent cellular cytotoxicity (ADCC) and complement-dependent cytototoxicity (CDC), (reviewed in Ben-Kasus et al., Mol Cell Biol 9, 1165-1172 (2007)). Trastuzumab was approved in 1998 for treatment of patients with ErbB2-overexpressing, also known as HER2-positive or HER2-positive metastatic breast cancers (MBCs) that have progressed after an extensive prior anti-cancer therapy (Baselga et al., J Clin Oncol 14, 737-744(1996); Slamon et al., N Engl J Med 344, 783-792 (2001)). However, patients' response to Trastuzumab monotherapy is relatively low (approximately 15%) and short lived (a median duration of 9 months) (Cobleigh et al., Clin Oncol 17: 2639-48 (1999)). On the other hand, Trastuzumab seems to display a synergistic effect when combined with chemotherapy, probably due to interruption of ErbB2-driven survival pathways (Arteaga et al., Cancer Res 54: 3758-65 (1994)). Although Trastuzumab provides patients with HER2-positive tumors a markedly better outcome than chemotherapy alone, virtually all treated patients will eventually progress on available therapies. Opportunities remain to improve outcomes for the patients with cancers that overexpress HER2.

One approach to antibody-targeted therapies is to utilize antibodies for delivery of cytotoxic drugs specifically to antigen-expressing cancer cells. Antibody-drug conjugates (ADCs), which may be called "immunotoxins", composed of maytansinoid DM1 linked to Trastuzumab show potent anti-tumor activities in HER2-overexpressing and Trastuzumab-sensitive or Trastuzumab-resistant tumor cell lines, and xenograft models of human breast cancer. Trastuzumab-MCC-DM1 (T-DM1) is approved for patients whose disease is refractory to HER2-directed therapies (Beeram et al., Cancer 118, 5733-5740 (2007)). However, T-DM1 shows no advantage over Trastuzumab when used as a first line therapy in patients with HER2+ metastatic breast cancer (MBC).

An alternative approach is a combination therapy, which has advantages: (i) reducing frequency of developing resistance, (ii) lowering doses of drugs that have non-overlapping toxicity and similar therapeutic profiles, and consequently increasing therapeutic index, (iii) sensitizing cells to one drug through use of another drug, and (iv) achieving enhanced potency by exploiting additive or synergistic effects on a biological activity by two drugs (Pegram et al., Oncogene 18:2241-2251 (1999); Konecny et al., Breast Cancer Res. and Treatment 67:223-233 (2001); Pegram et al., J. of the Nat. Cancer Inst. 96(10):739-749 (2004)).

HER2 dimerization inhibitor antibodies and EGFR inhibitors have been reported for combination therapies against cancer (US 2007/0020261). Pertuzumab (PERJETA) alone has been demonstrated to have a therapeutic activity in MBC patients. In addition, Pertuzumab is indicated for use in combination with Trastuzumab and docetaxel for treatment of patients with HER2-positive metastatic breast cancer (MBC) who have not received a prior anti-ErbB2 therapy or chemotherapy for a metastatic disease (Baselga et al., J Clin Oncol 28, 1138-1144, (2010)).

There remains a need for novel ErbB2 antibodies having therapeutic effects on HER2-positive tumor cells when used alone or in combination with other therapeutic agents such as Trastuzumab, preferably synergistically.

SUMMARY OF THE INVENTION

The present invention relates to five anti-HER2 antibodies 4C9, 4H2, 4G6, 5H12, and 5G9 and related binding proteins, polynucleotides, vectors and pharmaceutical compositions as well as uses thereof. The terms "ErbB2 antibody," "HER2 antibody," "anti-ErbB2 antibody" and "anti-HER2 antibody" are used herein interchangeably and refer to an antibody that binds specifically to ErbB2 or HER2.

A binding protein is provided. The binding protein comprises an antigen binding fragment that specifically binds to receptor tyrosine-protein kinase ErbB-2 (ErbB2). The antigen binding fragment comprises at least one amino acid sequence selected from the group consisting of SEQ ID NOs: 17-51 and 56-160.

The antigen binding fragment may comprise at least one variable domain consisting of an amino acid sequence selected from the group consisting of SEQ ID NOs: 17-51.

The antigen binding fragment may comprise two variable domains selected from the group consisting of: SEQ ID NOs: 17 and 18; SEQ ID NOs: 19 and 20; SEQ ID NOs: 21 and 22; SEQ ID NOs: 23 and 24; SEQ ID NOs: 25 and 26; SEQ ID NOs: 27 and 32; SEQ ID NOs: 27 and 33; SEQ ID NOs: 27 and 34; SEQ ID NOs: 27 and 35; SEQ ID NOs: 27 and 36; SEQ ID NOs: 27 and 37; SEQ ID NOs: 27 and 38; SEQ ID NOs: 28 and 32; SEQ ID NOs: 28 and 33; SEQ ID NOs: 28 and 34; SEQ ID NOs: 28 and 35; SEQ ID NOs: 28 and 36; SEQ ID NOs: 28 and 37; SEQ ID NOs: 28 and 38; SEQ ID NOs: 29 and 32; SEQ ID NOs: 29 and 33; SEQ ID NOs: 29 and 34; SEQ ID NOs: 29 and 35; SEQ ID NOs: 29 and 36; SEQ ID NOs: 29 and 37; SEQ ID NOs: 29 and 38; SEQ ID NOs: 30 and 32; SEQ ID NOs: 30 and 33; SEQ ID NOs: 30 and 34; SEQ ID NOs: 30 and 35; SEQ ID NOs: 30 and 36; SEQ ID NOs: 30 and 37; SEQ ID NOs: 30 and 38; SEQ ID NOs: 31 and 32; SEQ ID NOs: 31 and 33; SEQ ID NOs: 31 and 34; SEQ ID NOs: 31 and 35; SEQ ID NOs: 31 and 36; SEQ ID NOs: 31 and 37; SEQ ID NOs: 31 and 38; SEQ ID NOs: 39 and 45; SEQ ID NOs: 39 and 46; SEQ ID NOs: 39 and 47; SEQ ID NOs: 39 and 48; SEQ ID NOs: 39 and 49; SEQ ID NOs: 39 and 50; SEQ ID NOs: 39 and 51; SEQ ID NOs: 40 and 45; SEQ ID NOs: 40 and 46; SEQ ID NOs: 40 and 47; SEQ ID NOs: 40 and 48; SEQ ID NOs: 40 and 49; SEQ ID NOs: 40 and 50; SEQ ID NOs: 40 and 51; SEQ ID NOs: 41 and 45; SEQ ID NOs: 41 and 46; SEQ ID NOs: 41 and 47; SEQ ID NOs: 41 and 48; SEQ ID NOs: 41 and 49; SEQ ID NOs: 41 and 50; SEQ ID NOs: 41 and 51; SEQ ID NOs: 42 and 45; SEQ ID NOs: 42 and 46; SEQ ID NOs: 42 and 47; SEQ ID NOs: 42 and 48; SEQ ID NOs: 42 and 49; SEQ ID NOs: 42 and 50; SEQ ID NOs: 42 and 51; SEQ ID NOs: 43 and 45; SEQ ID NOs: 43 and 46; SEQ ID NOs: 43 and 47; SEQ ID NOs: 43 and 48; SEQ ID NOs: 43 and 49; SEQ ID NOs: 43 and 50; SEQ ID NOs: 43 and 51; SEQ ID NOs: 44 and 45; SEQ ID NOs: 44 and 46; SEQ ID NOs: 44 and 47; SEQ ID NOs: 44 and 48; SEQ ID NOs: 44 and 49; SEQ ID NOs: 44 and 50; and SEQ ID NOs: 44 and 51.

The antigen binding fragment may comprise at least one complementarity determining region (CDR) consisting of an amino acid sequence selected from the group consisting of SEQ ID NOs: 56-160.

The antigen binding fragment may comprise at least one set of three CDRs, wherein at least one CDR set is selected from the group consisting of 4C9 VH Set, 4C9 VL Set, 4H2 VH Set, 4H2 VL Set, 4G6 VH Set, 4G6 VL Set, 5F12 VH Set, 5F12 VL Set, 5G9 VH Set, 5G9 VL Set, 5F12.VH.V1 Set, 5F12.VH.1 Set, 5F12.VH.2 Set, 5F12.VH.3 Set, 5F12.VH.4 Set, 5F12.VL.V1 Set, 5F12.VL.1 Set, 5F12.VL.2 Set, 5F12.VL.3 Set, 5F12.VL.4 Set, 5F12.VL.5 Set, 5F12.VL.6 Set, 5G9.VH.V1 Set, 5G9.VH.1 Set, 5G9.VH.2 Set, 5G9.VH.3 Set, 5G9.VH.4 Set, 5G9.VH.5 Set, 5G9.VL.V1 Set, 5G9.VL.1 Set, 5G9.VL.2 Set, 5G9.VL.3 Set, 5G9.VL.4 Set, 5G9.VL.5 Set and 5G9.VL.6 Set.

The antigen binding fragment may comprise two CDR sets of three CDRs, and wherein the two CDR sets are selected from the group consisting of 4C9 VH Set and 4C9 VL Set; 4H2 VH Set and 4H2 VL Set; 4G6 VH Set and 4G6 VL Set; 5F12 VH Set and 5F12 VL Set; 5G9 VH Set and 5G9 VL Set; 5F12.VH.V1 Set and 5F12.VL.V1 Set; 5F12.VH.1 Set and 5F12.VL.V1 Set; 5F12.VH.2 Set and 5F12.VL.V1 Set; 5F12.VH.3 Set and 5F12.VL.V1 Set; 5F12.VH.4 Set and 5F12.VL.V1 Set; 5F12.VH.V1 Set and 5F12.VL.1 Set; 5F12.VH.1 Set and 5F12.VL.1 Set; 5F12.VH.2 Set and 5F12.VL.1 Set; 5F12.VH.3 Set and 5F12.VL.1 Set; 5F12.VH.4 Set and 5F12.VL.1 Set; 5F12.VH.V1 Set and 5F12.VL.2 Set; 5F12.VH.1 Set and 5F12.VL.2 Set; 5F12.VH.2 Set and 5F12.VL.2 Set; 5F12.VH.3 Set and 5F12.VL.2 Set; 5F12.VH.4 Set and 5F12.VL.2 Set; 5F12.VH.V1 Set and 5F12.VL.3 Set; 5F12.VH.1 Set and 5F12.VL.3 Set; 5F12.VH.2 Set and 5F12.VL.3 Set; 5F12.VH.3 Set and 5F12.VL.3 Set; 5F12.VH.4 Set and 5F12.VL.3 Set; 5F12.VH.V1 Set and 5F12.VL.4 Set; 5F12.VH.1 Set and 5F12.VL.4 Set; 5F12.VH.2 Set and 5F12.VL.4 Set; 5F12.VH.3 Set and 5F12.VL.4 Set; 5F12.VH.4 Set and 5F12.VL.4 Set; 5F12.VH.V1 Set and 5F12.VL.5 Set; 5F12.VH.1 Set and 5F12.VL.5 Set; 5F12.VH.2 Set and 5F12.VL.5 Set; 5F12.VH.3 Set and 5F12.VL.5 Set; 5F12.VH.4 Set and 5F12.VL.5 Set; 5F12.VH.V1 Set and 5F12.VL.6 Set; 5F12.VH.1 Set and 5F12.VL.6 Set; 5F12.VH.2 Set and 5F12.VL.6 Set; 5F12.VH.3 Set and 5F12.VL.6 Set; 5F12.VH.4 Set and 5F12.VL.6 Set; 5G9.VH.V1 Set and 5G9.VL.V1 Set; 5G9.VH.1 Set and 5G9.VL.V1 Set; 5G9.VH.2 Set and 5G9.VL.V1 Set; 5G9.VH.3 Set and 5G9.VL.V1 Set; 5G9.VH.4 Set and 5G9.VL.V1 Set; 5G9.VH.5 Set and 5G9.VL.V1 Set; 5G9.VH.V1 Set and 5G9.VL.1 Set; 5G9.VH.1 Set and 5G9.VL.1 Set; 5G9.VH.2 Set and 5G9.VL.1 Set; 5G9.VH.3 Set and 5G9.VL.1 Set; 5G9.VH.4 Set and 5G9.VL.1 Set; 5G9.VH.5 Set and 5G9.VL.1 Set; 5G9.VH.V1 Set and 5G9.VL.2 Set; 5G9.VH.1 Set and 5G9.VL.2 Set; 5G9.VH.2 Set and 5G9.VL.2 Set; 5G9.VH.3 Set and 5G9.VL.2 Set; 5G9.VH.4 Set and 5G9.VL.2 Set; 5G9.VH.5 Set and 5G9.VL.2 Set; 5G9.VH.V1 Set and 5G9.VL.3 Set; 5G9.VH.1 Set and 5G9.VL.3 Set; 5G9.VH.2 Set and 5G9.VL.3 Set; 5G9.VH.3 Set and 5G9.VL.3 Set; 5G9.VH.4 Set and 5G9.VL.3 Set; 5G9.VH.5 Set and 5G9.VL.3 Set; 5G9.VH.V1 Set and 5G9.VL.4 Set; 5G9.VH.1 Set and 5G9.VL.4 Set; 5G9.VH.2 Set and 5G9.VL.4 Set; 5G9.VH.3 Set and 5G9.VL.4 Set; 5G9.VH.4 Set and 5G9.VL.4 Set; 5G9.VH.5 Set and 5G9.VL.4 Set; 5G9.VH.V1 Set and 5G9.VL.5 Set; 5G9.VH.1 Set and 5G9.VL.5 Set; 5G9.VH.2 Set and 5G9.VL.5 Set; 5G9.VH.3 Set and 5G9.VL.5 Set; 5G9.VH.4 Set and 5G9.VL.5 Set; 5G9.VH.5 Set and 5G9.VL.5 Set; 5G9.VH.V1 Set and 5G9.VL.6 Set; 5G9.VH.1 Set and 5G9.VL.6 Set; 5G9.VH.2 Set and 5G9.VL.6 Set; 5G9.VH.3 Set and 5G9.VL.6 Set; 5G9.VH.4 Set and 5G9.VL.6 Set; and 5G9.VH.5 Set and 5G9.VL.6 Set.

The antigen binding fragment may comprise CDR-H1, CDR-H2, CDR-H3, CDR-L1, CDR-L2 and CDR-L3, wherein CDR-H1 is selected from the group consisting of SEQ ID NOs: 56, 62, 68, 74, 80, 86, 89, 92, 95, 98, 122, 125, 128, 131, 134 and 137; CDR-H2 is selected from the group consisting of SEQ ID NOs: 57, 63, 69, 75, 81, 87, 90, 93, 96, 99, 123, 126, 129, 132, 135 and 138; CDR-H3 is selected from the group consisting of SEQ ID NOs: 58, 64, 70, 76, 82, 88, 91, 94, 97, 100, 124, 127, 130, 133, 136 and 139; CDR-L1 is selected from the group consisting of SEQ ID NOs: 59, 65, 71, 77, 83, 101, 104, 107, 110, 113, 116, 119, 140, 143, 146, 149, 152, 155 and 158; CDR-L2 is selected from the group consisting of SEQ ID NOs: 60, 66, 72, 78, 84, 102, 105, 108, 111, 114, 117, 120, 141, 144, 147, 150, 153, 156 and 159; and CDR-L3 is selected from the group consisting of SEQ ID NOs: 61, 67, 73, 79, 85, 103, 106, 109, 112, 115, 118, 121, 142, 145, 148, 151, 154, 157 and 160.

The binding protein may further comprise a human acceptor framework sequence. The human acceptor framework sequence may comprise an amino acid sequence selected from the group consisting of SEQ ID NOs: 3-10. The human acceptor framework sequence may comprise an amino acid sequence selected from the group consisting of SEQ ID NOs: 3-10 and 161-166. The human acceptor framework sequence may comprise at least one framework region amino acid substitution at a key residue, and the key residue is selected from the group consisting of: a residue adjacent to a CDR; a glycosylation site residue; a rare residue; a residue capable of interacting with human ErbB2; a residue capable of interacting with a CDR; a canonical residue; a contact residue between heavy chain variable region and light chain variable region; a residue within a Vernier zone; and a residue in a region that overlaps between a Chothia-defined variable heavy chain CDR1 and a Kabat-defined first heavy chain framework.

Where the binding protein comprises a human acceptor framework sequence comprising at least one framework region amino acid substitution at the key residue, the binding protein may further comprise a consensus human variable domain sequence.

Where the human acceptor framework comprises at least one framework region amino acid substitution, the human acceptor framework may consist of an amino acid sequence at least about 65% identical to a sequence of a human germline acceptor framework, and comprise at least 70 amino acid residues identical to the human germline acceptor framework. The binding protein may be selected from the group consisting of an immunoglobulin molecule, a monoclonal antibody, a chimeric antibody, a CDR-grafted antibody, a Fab, a Fab', a F(ab')$_2$, an Fv, a disulfide linked Fv, an scFv, a single domain antibody, a diabody, a multispecific antibody, a dual specific antibody, and a bispecific antibody.

The binding protein may be an antibody. The antibody may be selected from the group consisting of a monoclonal antibody, a full-length tetrameric immunoglobulin, an IgG molecule, an IgG1 molecule, a chimeric antibody, a CDR-grafted antibody, a humanized antibody, and an affinity matured antibody. In one embodiment, the binding protein is a humanized antibody. In another embodiment, the antibody is a monoclonal antibody.

The terms "ErbB2-mediated bioactivity" and "ErbB2 activity" are used herein interchangeably and refer to a biological activity caused or interfered by ErbB2 in a biological system such as cell, tissue, organ or subject, or a sample. The ErbB2-mediated bioactivity or ErbB2 activity may be upregulated in cells overexpressing ErbB2. Examples of ErbB2-mediated bioactivities include homodimering with itself, heterodimerizing with EGFR, or ErbB3 or ErbB4, signaling pathways regulated by ErbB2 and ErbB2-dependent cell growth. The sample may be obtained from a subject. The cells may be in a subject.

A subject may be a mammal, for example, a human. The subject may suffer from a disease or disorder, in which an ErbB2 activity is detrimental. The term "detrimental" as used herein refers to an alteration of an ErbB2 activity in a subject having a disease or disorder as compared with that in a control subject, who does not have the disease or disorder. Where the ErbB2 activity is detrimental in a subject having a disease or disorder, the ErbB2 activity may be higher than that in a control subject not having the disease or disorder, for example, by at least about 10%, 20%, 30%, 40%, 50%, 60%, 70%, 80%, 90%, 95% or 99%.

The binding protein may modulate an ErbB2-mediated bioactivity. The term "modulate" as used herein refers to increasing or reducing an ErbB2-mediated bioactivity. Where an ErbB2-mediated bioactivity is altered, the binding protein may neutralize the altered ErbB2-mediated bioactivity. Where an ErbB2-mediated bioactivity is upregulated, the binding protein may reduce, inhibit, block, or antagonize the upregulated ErbB2-mediated bioactivity. The binding protein may modulate at least about 10%, 20%, 30%, 40%, 50%, 60%, 70%, 80%, 90%, 95% or 99% of an ErbB2-mediated bioactivity, for example, in a sample or cells. For such a binding protein, a method of modulating an ErbB2-mediated bioactivity in a sample or cells is provided. The method comprises administering an effective amount of the binding protein to the sample or the cells having an ErbB2-mediated bioactivity, whereby the ErbB2-mediated bioactivity is modulated, for example, by at least about 10%, 20%, 30%, 40%, 50%, 60%, 70%, 80%, 90%, 95% or 99%. A medicament for modulating an ErbB2-mediated bioactivity in, for example, a sample, cells or a subject is provided. The medicament may comprise an effective amount of the binding protein and a pharmaceutically acceptable carrier. A method for manufacturing the medicament is provided. The manufacturing method comprises mixing the binding protein with the pharmaceutically acceptable carrier.

The binding protein may be internalized into an ErbB2-positive cell upon contact with the cell. The term "ErbB2-positive cell" as used herein refers to a cell that expresses ErbB2. In one embodiment, the ErbB2-positive cell overexpresses ErbB2. Such a binding protein may be used in antibody-drug conjugate (ADC) applications. The binding protein may have an internalization rate of at least about 5%, 10%, 15%, 20%, 30% or 50%. The binding protein may be internalized by endocytosis. The binding protein may be internalized in a complex with ErbB2. For such a binding protein, a method of internalizing the binding protein into an ErbB2-positive cell is provided. The method comprising contacting the cell with an effective amount of the binding protein, whereby the binding protein is internalized into the cell. The cell may be in a subject. A medicament for internalizing the binding protein into ErbB2-positive cells is provided. The medicament may comprise an effective amount of the binding protein and a pharmaceutically acceptable carrier. A method for manufacturing the medicament is provided. The manufacturing method comprises mixing the binding protein with the pharmaceutically acceptable carrier.

The binding protein may enhance internalization of an additional agent into ErbB2-positive cells upon contact with the cells together, either concurrently or sequentially. The enhancement may be at least about 10%, 20%, 30%, 40%, 50%, 60%, 70%, 80%, 90%, 95% or 99% within a predetermined period of time, for example, within about 0.5, 1, 2, 4, 6, 8, 10, 12, 16 or 24 hours after contact. The additional agent may be an antibody or antigen binding fragment thereof capable of binding ErbB2, but different from the binding protein. The ErbB2 may be human ErbB2. The additional agent may comprise Trastuzumab, Pertuzumab or a combination thereof. The binding protein may enhance internalization of Trastuzumab into ErbB2 cells by at least about 20% within 2 hours after contact.

The binding protein may inhibit growth of ErbB2-positive cells. The growth of the ErbB2 cells may be inhibited by at least about 10%, 20%, 30%, 40%, 50%, 60%, 70%, 80%, 90%, 95% or 99%. The ErbB2-positive cells may be BT474 cells. The binding protein may inhibit the growth of the BT474 cells by at least about 70%.

The binding protein may inhibit growth of an ErbB2-positive tumor, optionally synergistically with an additional ErbB2 antibody. The growth of the ErbB2-positive tumor may be inhibited by at least about 10%, 20%, 30%, 40%, 50%, 60%, 70%, 80%, 90%, 95% or 99%. The tumor may be resistant to the additional ErbB2 antibody. The synergistic inhibition of the tumor growth by the binding protein and the additional ErbB2 antibody used together, either concurrently or sequentially, may be at least about 5%, 10%, 20%, 30%, 40% or 50% more than that the additive inhibition by the binding protein and the additional ErbB2 antibody used alone. The additional ErbB2 antibody may be Trastuzumab. The binding protein may inhibit the growth of a tumor that is ErbB2-positive and Trastuzumab-resistant by at least about 70% when used with Trastuzumab.

A binding protein construct is also provided. The binding protein construct comprises a binding protein of the present invention and a linker polypeptide or an immunoglobulin constant domain. The immunoglobulin constant domain may be a heavy chain immunoglobulin constant domain selected from the group consisting of a human IgM constant domain, a human IgG1 constant domain, a human IgG2 constant domain, a human IgG3 constant domain, a human IgG4 constant domain, a human IgE constant domain, and a human IgA constant domain. The immunoglobulin constant domain may comprise an amino acid sequence selected from the group consisting of SEQ ID NO: 1, SEQ ID NO: 2 and combinations thereof. In the binding protein construct, the binding protein may possess a human glycosylation pattern.

A binding protein conjugate is further provided. The binding protein conjugate comprises a binding protein construct of the present invention and an agent selected from the group consisting of an imaging agent, a therapeutic agent, a cytotoxic agent, and an immunoadhesion molecule. The imaging agent may be selected from the group consisting of a radiolabel, an enzyme, a fluorescent label, a luminescent label, a bioluminescent label, a magnetic label, and biotin. The agent may be selected from the group consisting of an anti-metabolite, an alkylating agent, an antibiotic, a growth factor, a cytokine, an anti-angiogenic agent, an anti-mitotic agent, an anthracycline, a toxin, and an apoptotic agent. In the binding protein conjugate, the binding protein may possess a human glycosylation pattern. The binding protein conjugate may be an antibody conjugate.

The binding protein conjugate may be internalized into an ErbB2-positive cell upon contact with the cell. The binding protein conjugate may be internalized by endocytosis. The binding protein conjugate may be internalized in a complex with ErbB2. For such a binding protein conjugate, a method of internalizing the binding protein conjugate into an ErbB2-positive cell is provided. The method comprising contacting the cell with an effective amount of the binding protein conjugate, whereby the binding protein conjugate is internalized into the cell. The cell may be in a subject. A medicament for internalizing the binding protein conjugate into an ErbB2-positive cell is provided. The medicament may comprise an effective amount of the binding protein conjugate and a pharmaceutically acceptable carrier. A method for manufacturing the medicament is provided. The manufacturing method comprises mixing the binding protein conjugate with the pharmaceutically acceptable carrier.

The binding protein may exist as a crystal. The crystal is a carrier-free pharmaceutical controlled release crystal. The binding protein crystal may have a greater half-life in vivo than a soluble counterpart of the binding protein. The binding protein crystal may retain biological activity of a non-crystal form of the binding protein.

The binding protein construct may exist as a crystal. The crystal is a carrier-free pharmaceutical controlled release crystal. The binding protein construct crystal may have a greater half-life in vivo than a soluble counterpart of the binding protein construct. The binding protein construct crystal may retain biological activity of a non-crystal form of the binding protein construct.

The binding protein conjugate may exist as a crystal. The crystal is a carrier-free pharmaceutical controlled release crystal. The binding protein conjugate crystal may have a greater half-life in vivo than a soluble counterpart of the binding protein conjugate. The binding protein conjugate crystal may retain biological activity of a non-crystal form of the binding protein conjugate.

For each binding protein of the present invention, a polynucleotide encoding the binding protein is provided. A vector comprising the polynucleotide is also provided. The vector may be selected from the group consisting of pcDNA, pTT, pTT3, pEFBOS, pBV, NV, and pBJ.

A host cell comprising a vector of the present invention is provided. The host cell may be a prokaryotic cell. The host cell may be *Escherichia coli*. The host cell may be a eukaryotic cell. The eukaryotic cell may be selected from the group consisting of a protist cell, an animal cell, a plant cell, and a fungal cell. The animal cell may be selected from the group consisting of a mammalian cell, an avian cell, and an insect cell. The mammalian cell may be a CHO cell or a COS cell. The fungal cell may be *Saccharomyces cerevisiae*. The insect cell may be an Sf9 cell.

A method of producing the binding protein of the present invention is provided. The method comprises culturing a host cell in a culture medium under conditions sufficient to produce the binding protein. The host cell comprises a vector, which comprises a polynucleotide encoding the binding protein. A binding protein produced according to this method is provided.

A releasing composition for releasing the binding protein of the present invention is provided. The composition comprises a formulation and at least one polymeric carrier. The formulation comprises a crystallized binding protein and an ingredient. The polymeric carrier may be a polymer selected from the group consisting of poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutyrate), poly (caprolactone), poly (dioxanone), poly (ethylene glycol), poly ((hydroxypropyl) methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof. The ingredient may be selected from the group consisting of albumin, sucrose, trehalose, lactitol, gelatin, hydroxypropyl-cyclodextrin, methoxypolyethylene glycol and polyethylene glycol. A method for releasing a binding protein in a mammal from the releasing composition is provide. The method comprises administering to the mammal an effective amount of the releasing composition, whereby the binding protein is released in the mammal. A method for manufacturing the releasing composition is provided. The manufacturing method comprises mixing the formulation with at least one polymeric carrier.

A pharmaceutical composition comprising the binding protein of the present invention and a pharmaceutically acceptable carrier. The pharmaceutical composition may further comprise at least one additional agent for treating a disorder in which ErbB2 activity is detrimental. The additional agent may be selected from the group consisting of a therapeutic agent; an imaging agent; an antineoplastic agent; a chemotherapeutic agent; an angiogenesis inhibitor; an anti-VEGF antibody; an anti-EGFR antibody; an anti-cMet antibody; an anti-ErbB3 antibody; an anti-ErbB2 antibody; an anti-CD20 antibody; aflibercept; a kinase inhibitor; a co-stimulation molecule blocker; an anti-B7.2 antibody; a CTLA4-Ig; an adhesion molecule blocker; an anti-E selectin antibody; an anti-L selectin antibody; an anti-cytokine antibody or functional fragment thereof; an anti-IL-18 antibody; an anti-TNF antibody; anti-IL-6 antibody; methotrexate; a corticosteroid; a cyclosporin; a rapamycin; FK506; a DNA alkylating agent; cisplatin; carboplatin; an anti-tubulin agent; paclitaxel; docetaxel; doxorubicin; gemcitabine; gemzar; an anthracycline; adriamycin; a topoisomerase I inhibitor; a topoisomerase II inhibitor; 5-fluorouracil (5-FU); leucovorin; irinotecan; a receptor tyrosine kinase inhibitor, an apoptosis inhibitor; a Bcl2/Bclx inhibitor; erlotinib, gefitinib, a COX-2 inhibitor, celecoxib, cyclosporin; rapamycin; a detectable label or reporter molecule; a TNF antagonist; an antirheumatic; a muscle relaxant; a narcotic; an analgesic; an anesthetic; a sedative; a local anesthetic; a neuromuscular blocker; an antimicrobial agent; an antipsoriatic agent; a corticosteroid; an anabolic steroid; an erythropoietin; an immunization; an immunoglobulin; an immunosuppressive agent; a growth hormone; a hormone replacement drug; a radiopharmaceutical drug; an antidepressant; an antipsychotic drug; a stimulant; an asthma medication; a beta agonist; an inhaled steroid; an epinephrine; an epinephrine analog thereof; a cytokine; and a cytokine antagonist.

A method for treating a disease or disorder in subject is provided. ErbB2 activity is detrimental in the disease or disorder. The treatment method comprises administering to the subject an effective amount of a binding protein, binding protein construct or binding protein conjugate of the present invention, whereby the ErbB2 activity is modulated in the subject. The disease or disorder may be selected from the group consisting of breast cancer, gastric cancer, colon cancer, rectal cancer, lung cancer, oropharynx cancer, hypopharynx cancer, esophageal cancer, stomach cancer, pancreas cancer, liver cancer, gallbladder cancer, bile duct cancer, small intestine cancer, urinary tract cancer, female genital tract cancer, male genital tract cancer, endocrine gland cancer, skin cancer, hemangioma, melanoma, sarcoma, brain tumor, nerve cancer, eye tumor, meninges cancer, solid tumor from hematopoietic malignancy, tumor metastases, ocular neovascularization, edema, rheumatoid arthritis, atherosclerotic plaques, Crohn's disease, inflammatory bowel disease, refractory ascites, psoriasis, sarcoidosis, arterial arteriosclerosis, sepsis, peptic ulcers, burns, pancreatitis, polycystic ovarian disease (POD), endometriosis, uterine fibroid, benign prostate hypertrophy, T-cell acute lymphoblastic leukemia (T-ALL), cerebral autosomal dominant arteriopathy with subcortical infarcts and leukoencephalopathy (CADA-SIL), multiple sclerosis (MS), tetralogy of Fallot (TOF), Alagille syndrome (AS), macular degeneration and age-related macular degeneration diseases, and other angiogenesis independent and dependent diseases characterized by aberrant ErbB2 activity. The disease or disorder may be a primary and metastatic cancer. The disease or disorder may be breast cancer. The female genital tract cancer is selected from the group consisting of cervical cancer, uterine cancer, ovarian cancer, choriocarcinoma, and gestational trophoblastic disease. The female genital tract cancer may be ovarian cancer. The disease or disorder may be gastric cancer. The disease or disorder may be lung cancer. The meninges cancer may be selected from the group consisting of an astrocytoma, a glioma, a glioblastoma, a retinoblastoma, a neuroma, a neuroblastoma, a Schwannoma, and a meningioma. The solid tumor from a hematopoietic malignancy may be a leukemia, a Hodgkin's leukemia, a non-Hodgkin's leukemia, a lymphoma, a Hodgkin's lymphoma, and a non-Hodgkin's lymphomas. The ocular neovascularization may be selected from the group consisting of diabetic blindness, a retinopathy, an age-related macular degeneration, and a rubeosis. Where the disease or disorder is a tumor, the treatment method may further comprise inhibiting growth of the tumor in the subject by, for example, at least about 10%, 20%, 30%, 40%, 50%, 60%, 70%, 80%, 90%, 95% or 99%. The tumor may be ErbB2-positive.

According to the treatment method, the binding protein, binding protein construct or binding protein conjugate, may be administered to the subject by at least one mode selected from the group consisting of parenteral, subcutaneous, intramuscular, intravenous, intraarterial, intraarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

The treatment method may further comprise administering one or more additional agents, either concurrently or sequentially. The additional agent may be an antibody or antigen binding fragment thereof capable of binding ErbB2, but different from the binding protein, binding protein construct or binding protein conjugate. The ErbB2 may be human ErbB2. The one or more additional agents may comprise Trastuzumab, Pertuzumab or a combination thereof. The method may further comprise modulating the ErbB2 activity in the subject synergistically with the one or more additional agents. The synergistic effect by the binding protein, binding protein construct or binding protein conjugate, and the one or more additional agents used together, either concurrently or sequentially, may be at least about 5%, 10%, 20%, 30%, 40% or 50% more than that the additive effect by the binding protein, binding protein construct or binding protein conjugate, and the one or more additional agents used alone.

The treatment method may further comprise administering a therapeutically effective amount of a second agent, either concurrently or sequentially. The second agent may be selected from the group consisting of methotrexate; an antibody or fragment thereof capable of binding human TNF; a corticosteroid; a cyclosporine; a rapamycin; FK506;

a non-steroidal anti-inflammatory agent (NSAID); a radiotherapeutic agent; an antineoplastic agent; a chemotherapeutic agent; a DNA alkylating agent; cisplatin; carboplatin; an anti-tubulin agent; paclitaxel; docetaxel; taxol; doxorubicin; gemcitabine; gemzar; an anthracycline; adriamycin; a topoisomerase I inhibitor; a topoisomerase II inhibitor; 5-fluorouracil (5-FU); leucovorin; irinotecan; a receptor tyrosine kinase inhibitor; erlotinib; gefitinib; a COX-2 inhibitor; celecoxib; a kinase inhibitor; an angiogenesis inhibitor; an anti-VEGF antibody; aflibercept; a co-stimulation molecule blocker; an anti-B7.1 antibody; an anti-B7.2 antibody; a CTLA4-Ig; an anti-CD20 antibody; an adhesion molecule blocker; an anti-LFA-1 antibody; an anti-E selectin antibody; and anti-L selectin antibody; a small molecule inhibitor; an anti-cytokine antibody or functional fragment thereof; an anti-IL-18 antibody; anti-TNF antibody; an anti-IL-6 antibody; an anti-cytokine receptor antibody; a detectable label or reporter; a TNF antagonist; an anti-rheumatic; a muscle relaxant; a narcotic; an analgesic; an anesthetic; a sedative; a local anesthetic; a neuromuscular blocker; an antimicrobial agent; an anti-psoriatic drug; a corticosteroid; an anabolic steroid; an erythropoietin; an immunization; an immunoglobulin; an immunosuppressive agent; a growth hormone; a hormone replacement drug; a radiopharmaceutical drug; an antidepressant; an antipsychotic drug; a stimulant; an asthma medication; a beta agonist; an inhaled steroid; an epinephrine; an epinephrine analog; a cytokine; and a cytokine antagonist.

For each treatment method, a medicament for treating a disease or disorder in subject is provided. ErbB2 activity is detrimental in the disease or disorder. The medicament may comprise an effective amount of the binding protein, binding protein construct or binding protein conjugate, and a pharmaceutically acceptable carrier. The medicament may further comprise one or more additional agents and/or a second agent. A method for manufacturing the medicament is provided. The manufacturing method comprises mixing the binding protein, binding protein construct or binding protein conjugate with the pharmaceutically acceptable carrier, and optionally the one or more additional agents and/or the second agent.

A method for inhibiting growth of ErbB2-positive cells is provided. The inhibition method comprises contacting the cells with an effective amount of a binding protein, binding protein construct or binding protein conjugate of the present invention. The growth of the ErbB2 cells may be inhibited by at least about 10%, 20%, 30%, 40%, 50%, 60%, 70%, 80%, 90%, 95% or 99%. The ErbB2-positive cells may be BT474 cells. The binding protein, binding protein construct or binding protein conjugate may inhibit the growth of the BT474 cells by at least 70%. The inhibition method may further comprise contacting the cells with one or more additional agents. The additional agent may be an antibody or antigen binding fragment thereof capable of binding ErbB2 but different from the binding protein, binding protein construct or binding protein conjugate. The binding protein, binding protein construct or binding protein conjugate, and the one or more additional agents may inhibit the growth of the cells synergistically. The synergistic inhibition of the growth of the ErbB2-positive cells by the binding protein, binding protein construct or binding protein conjugate, and the additional ErbB2 antibody used together, either concurrently or sequentially, may be at least about 5%, 10%, 20%, 30%, 40% or 50% more than that the additive inhibition by the binding protein, binding protein construct or binding protein conjugate, and the additional ErbB2 antibody used alone. The one or more additional agents may comprise Trastuzumab, Pertuzumab or a combination thereof. The cells may be in a subject. The subject may suffer from a disease or disorder in which ErbB2 activity is detrimental. The subject may be a mammal, for example, a human. For each inhibition method, a medicament for inhibiting growth of ErbB2-positive cells in a subject is provided. The medicament may comprise an effective amount of the binding protein, binding protein construct or binding protein conjugate, and a pharmaceutically acceptable carrier. The medicament may further comprise one or more additional agents. A method for manufacturing the medicament is provided. The manufacturing method comprises mixing the binding protein, binding protein construct or binding protein conjugate, with the pharmaceutically acceptable carrier, and optionally the one or more additional agents.

A method for inhibiting growth of an ErbB2-positive tumor is provided. The inhibition method comprises contacting the tumor with an effective amount of a binding protein, binding protein construct or binding protein conjugate of the present invention. The growth of the tumor may be inhibited by at least about 10%, 20%, 30%, 40%, 50%, 60%, 70%, 80%, 90%, 95% or 99%. The inhibition method may further comprise contacting the tumor with one or more additional agents. The additional agent may be an antibody or antigen binding fragment thereof capable of binding ErbB2, but different from the binding protein, binding protein construct or binding protein conjugate. The binding protein, binding protein construct or binding protein conjugate, and the one or more additional agents may inhibit the growth of the tumor synergistically. The synergistic inhibition of tumor growth by the binding protein, binding protein construct or binding protein conjugate, and the additional ErbB2 antibody used together, either concurrently or sequentially, may be at least about 5%, 10%, 20%, 30%, 40% or 50% more than that the additive inhibition by the binding protein, binding protein construct or binding protein conjugate, and the additional ErbB2 antibody used alone. The one or more additional agents may comprise Trastuzumab, Pertuzumab or a combination thereof. The tumor may be Trastuzumab-resistant. Where the additional ErbB2 antibody is Trastuzumab and the tumor is Trastuzumab-resistant, the growth of the tumor may be inhibited by at least about 70% by the binding protein, binding protein construct or binding protein conjugate when used in combination with Trastuzumab. The tumor may be in a subject. The subject may suffer from a disease or disorder in which ErbB2 activity is detrimental. The subject may be a mammal, for example, a human. For each inhibition method, a medicament for inhibiting growth of ErbB2-positive cells in a subject is provided. The medicament may comprise an effective amount of the binding protein, binding protein construct or binding protein conjugate, and a pharmaceutically acceptable carrier. The medicament may further comprise one or more additional agents. A method for manufacturing the medicament is provided. The manufacturing method comprises mixing the binding protein, binding protein construct or binding protein conjugate, with the pharmaceutically acceptable carrier, and optionally the one or more additional agents.

DETAILED DESCRIPTION OF THE INVENTION

Figure 1:
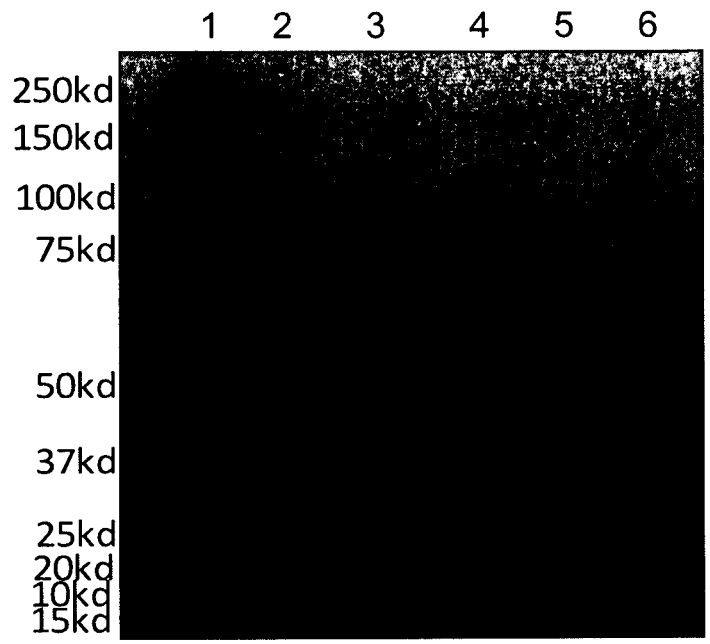
FIG. 1 depicts SDS-PAGE analysis of reduced IgG molecules isolated by the present invention. Note: Lane 1—molecular weight marker; Lane 2—IgG 4C9; Lane 3—IgG 4H2; Lane 4—IgG 4G6; Lane 5—IgG 5F12; Lane 6—IgG 5G9.
Figure 2:
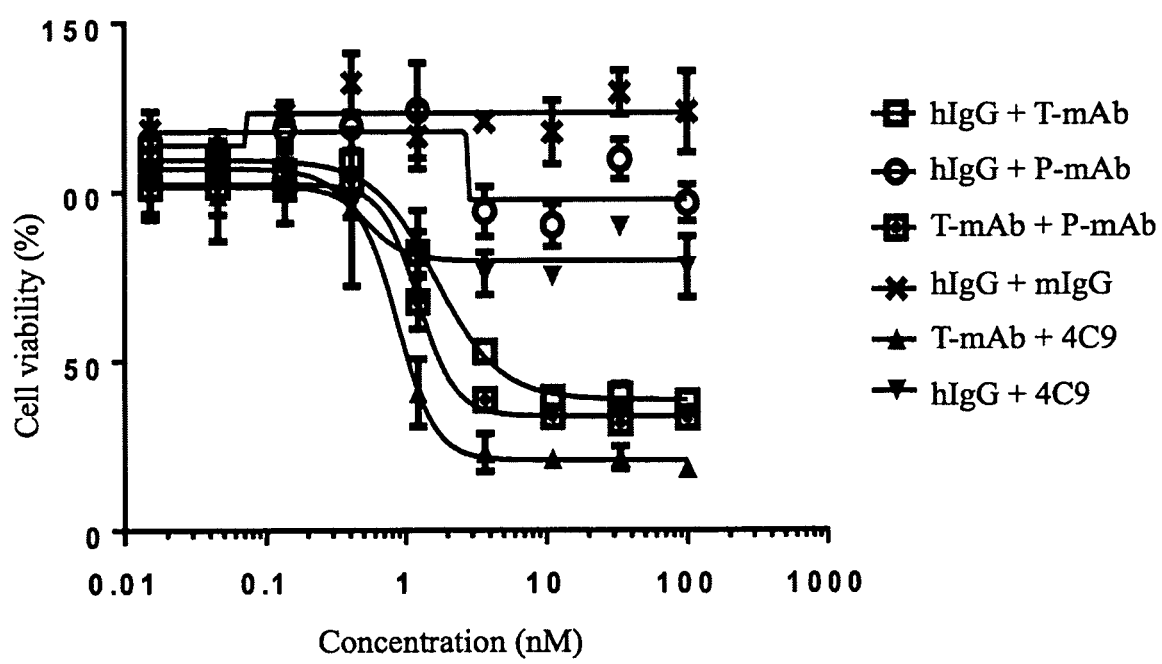
FIGS. 2A-2E show dose-response curves of five antibodies and the combinations of the present invention on inhibition of cell proliferation of BT474 breast cancer cell line. BT474 cells were seeded in 96 well plates and allowed to adhere for overnight. Experiment was carried out in medium containing 10% fetal bovine serum. Anti-ErbB2 antibodies, antibody mixture, or control IgGs were added and the cells were incubated for 144 hours at 37° C. Upon adding 50 μl of CellTiter-Glo (PROMEGA, G7573) for 10 min, measure luminescent signal according to manufacturer's instruction. The sample sets includes hIgG+mIgG (x), hIgG+Trastuzumab (□), hIgG+Pertuzumab (○), Trastuzumab+Pertuzumab (⊠), Trastuzumab+mAb of the present invention (▲), and hIgG+mAb of the present invention (▼). "mAb of the present invention" represents 4C9, 4H2, 4G6, 5F12, or 5G9. Note: T-mAb represents Trastuzumab, P-mAb represents Pertuzumab.
Figure 2:
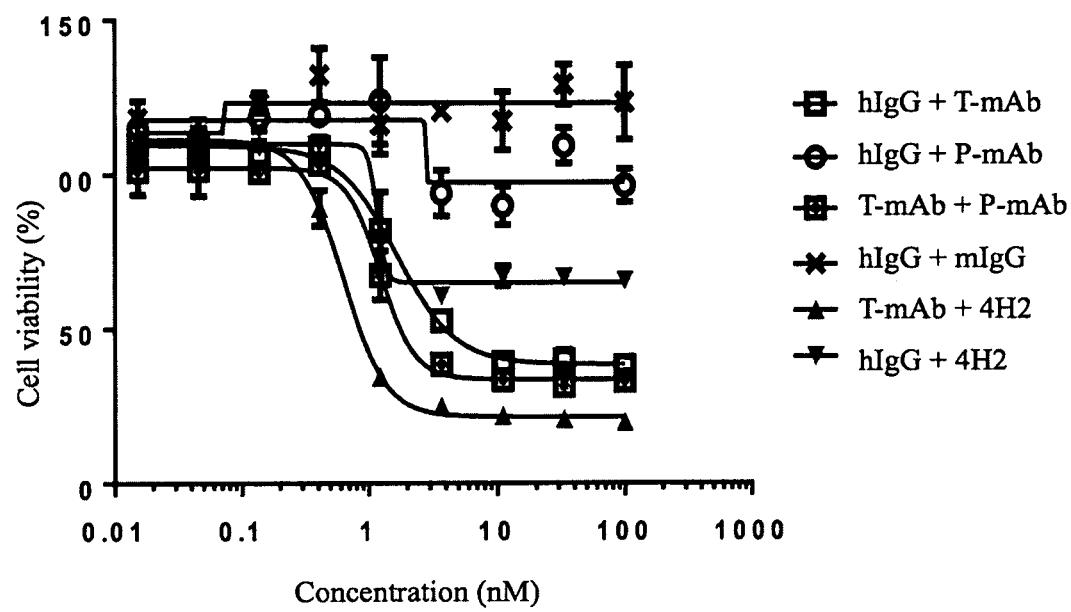
Figure 2:
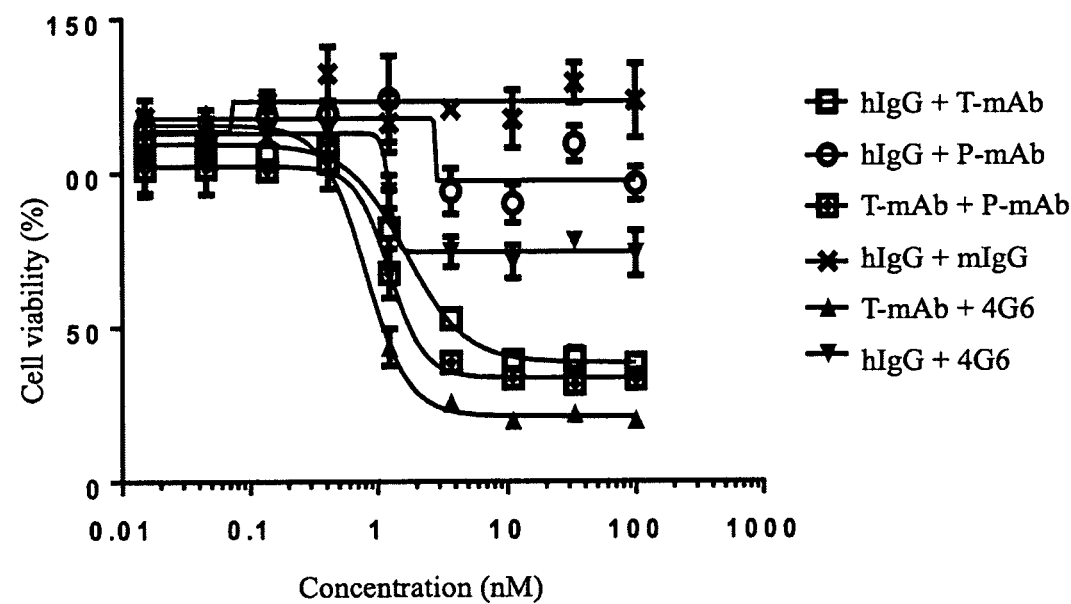
Figure 2:
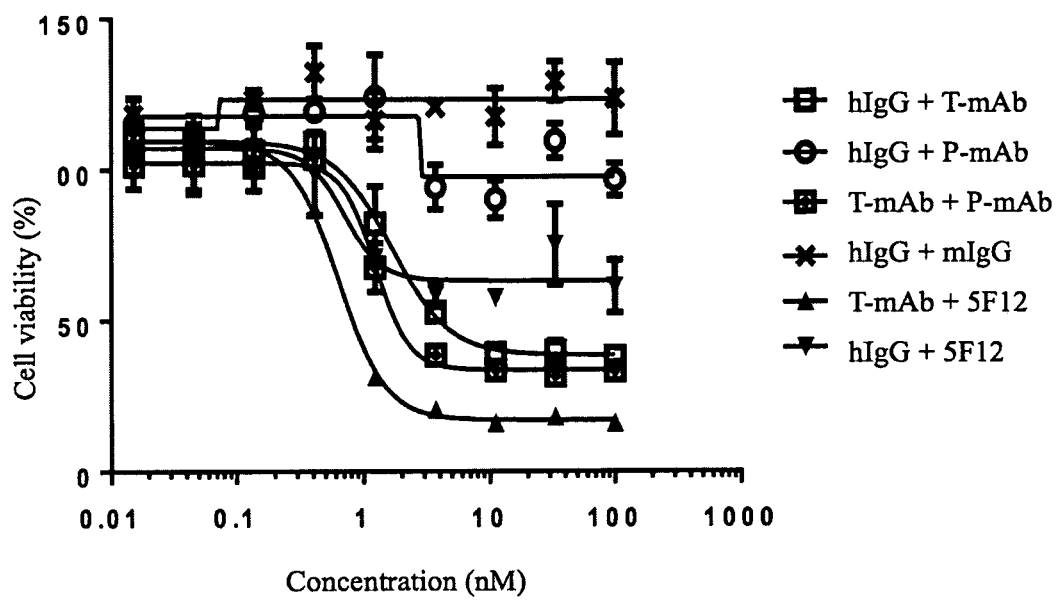
Figure 2:
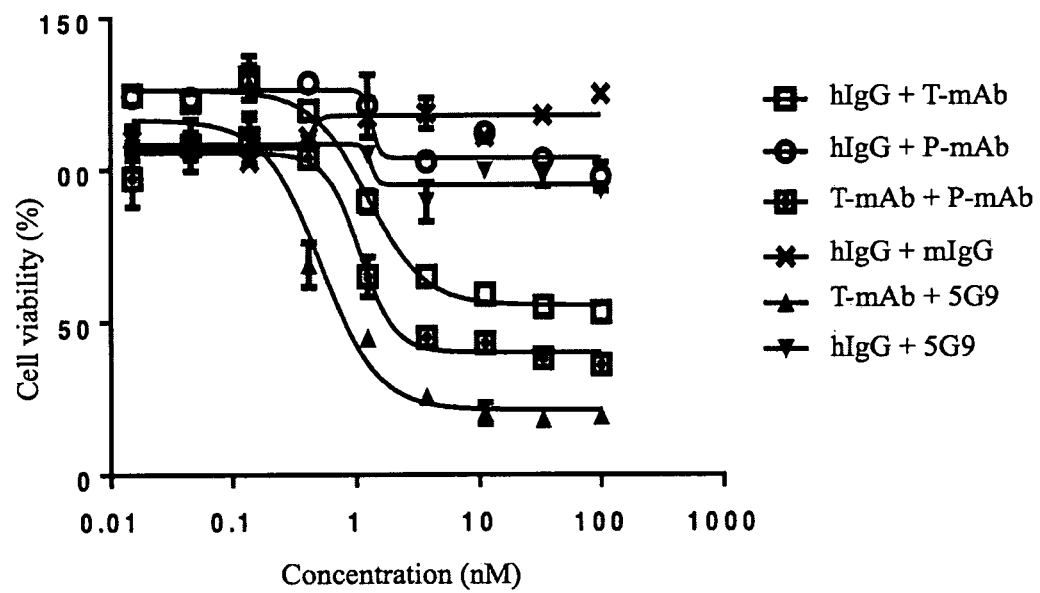

The present invention provides binding proteins that bind to human ErbB2 specifically, and optionally enhance synergistically Trastuzumab's anti-tumor efficacy (e.g., inhibiting, antagonizing, modulating ErbB2 expression, activity and/or signaling). The present invention is based on the discovery of five novel antibodies identified from a large-scale Trastuzumab-based synergistic efficacy screening by using cell-based functional assay as having more potent synergistic efficacy than Pertuzumab when being used with Trastuzumab. Specifically compared to the combination treatment of Trastuzumab and Pertuzumab, a combination of Trastuzumab with any one of these antibodies provides a significantly higher efficacy outcome for inhibiting growth of ErbB2-positive cells or tumors, for example, ErbB2-positive and Trastuzumab-resistant tumors.

Binding proteins that bind specifically to ErbB2, including anti-ErbB2 antibodies 4C9, 4H2, 4G6, 5H12, and 5G9, as well as chimeric and humanized variants thereof, are provided. In one embodiment, the binding protein comprises heavy chain CDR1, CDR2 and CDR3 sequences and light chain CDR1, CDR2 and CDR3 sequences of any one of these antibodies. In another embodiment, the binding protein comprises a heavy chain variable region sequence and a light chain variable region sequence of any one of these antibodies is provided. In yet another embodiment, a binding protein comprising an amino acid sequence at least 80%, 85%, 90% or 95% identical to a heavy chain variable region sequence of any one of these antibodies and an amino acid sequence at least 80%, 85%, 90% or 95% identical to a light chain variable region sequence of any one of these antibodies is provided.

A nucleic acid molecule having a nucleotide sequence that encodes a binding protein of the present invention is provided. Also provided are an expression vector comprising such a polynucleotide and a host cell comprising such an expression vector.

A method for producing a binding protein of the present invention is provided.

A composition comprising Trastuzumab and a binding protein of the present invention is provided. The binding protein may bind a distinct epitope different from the epitope bound by Trastuzumab or Pertuzumab. The binding protein may improve internalization of another ErbB2 antibody such as Trastuzumab significantly, and/or modulate ErbB2-mediated bioactivities, for example, phosphorylation of downstreaming signaling pathway and cell proliferation, synergistically with another ErbB2 antibody such as Trastuzumab.

A binding protein conjugate comprising a binding protein of the present invention and an anti-cancer agent is provided. The binding protein conjugate may be immunotoxic. Also provided is a composition comprising the binding protein conjugate and another ErbB2 antibody such as Trastuzumab and the binding protein conjugate, which may be immunotoxic.

A method for treating a disease or disorder in a subject, comprising administering an effective amount of a binding protein or composition of the present invention to the subject. The subject may be a mammal, for example, a human. The method may further comprise administering to the subject another ErbB2 antibody such as Trastuzumab. Also provided is a medicament comprising the binding protein, and optionally another ErbB2 antibody such as Trastuzumab for treating a disease or disorder (e.g., cancer) in a subject (e.g., human).

A method for enhancing internalization of another ErbB2 antibody such as Trastuzumab into ErbB2-positive is provided. The method comprises contacting the cells with a binding protein or composition of the present invention.

A. Definitions

The term "antibody" is used in the broadest sense, including immunoglobulin molecules and immunologically active portions of immunoglobulin molecules, i.e., molecules that contain an antigen binding site that immunospecifically binds to an antigen, and specifically covers monoclonal antibodies (including full-length monoclonal antibodies), polyclonal antibodies, and multi-specific antibodies (e.g., bispecific antibodies). Antibodies (Abs) and immunoglobulins (Igs) are glycoproteins having the same structural characteristics. While antibodies exhibit binding specificity to a specific target, immunoglobulins include both antibodies and other antibody-like molecules, which lack target specificity. Native antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end. Moreover, the term "antibody" (Ab) or "monoclonal antibody" (mAb) is meant to include both intact molecules, as well as, antibody fragments (such as, for example, Fab and F(ab')$_2$ fragments) which are capable of specifically binding to a protein. Fab and F(ab')$_2$ fragments lack the Fc fragment of intact antibody, clear more rapidly from the circulation of the animal or plant, and may have less non-specific tissue binding than an intact antibody (Wahl, et al., J Nucl Med 24:316 (1983)).

A "chimeric antibody" refers in its broadest sense to an antibody that contains one or more regions from one antibody and one or more regions from one or more other antibodies. As used herein, a "chimeric antibody" is generally an antibody that is partially of human origin and partially of non-human origin, i.e., derived in part from a non-human animal such as a mouse or a rat. Methods for producing chimeric antibodies are known in the art. See e.g., Morrison, Science 229: 1202 (1985); Oi, et al, BioTechniques 4:214 (1986); Gillies, et al, J Immunol Methods 125:191 (1989).

The terms "Kabat numbering" refer to a system of numbering amino acid residues which are more variable (i.e., hypervariable) than other amino acid residues in the heavy and light chain variable regions of an antibody, or an antigen binding portion thereof (Kabat et al, Ann. NY Acad. Sci, 190: 382-391 (1971) and Kabat et al. *Sequences of Proteins of Immunological Interest*, Fifth Edition, U.S. Department of Health and Human Services, NIH Publication No. 91-3242 (1991)). For the heavy chain variable region (VH), the hypervariable region ranges from amino acid positions 31 to 35 for CDR1, amino acid positions 50 to 66 for CDR2, and amino acid positions 95 to 102 for CDR3. For the light chain variable region (VL), the hypervariable region ranges from amino acid positions 24 to 34 for CDR1, amino acid positions 50 to 56 for CDR2, and amino acid positions 89 to 97 for CDR3.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like," i.e., more similar to human germline variable sequences. A "humanized antibody" is an antibody or a variant, derivative, analog, or fragment thereof, which specifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98% or 100% identical to the amino acid sequence of a non-human antibody CDR.

As used herein, the terms "acceptor" and "acceptor antibody" refer to an antibody or nucleic acid sequence providing or encoding at least 80%, at least 85%, at least 90%, at least 95%, at least 98%, or 100% of the amino acid sequences of one or more of the framework regions (FRs). In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the frame-work regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well known in the art, antibodies in development, or antibodies commercially available).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994). ErbB2 antibody scFv fragments are described in WO93/16185; U.S. Pat. Nos. 5,571,894; and 5,587,458.

The term "immunoglobulin" is commonly used as a collective designation of the mixture of antibodies found in blood or serum, but may also be used to designate a mixture of antibodies derived from other sources.

The term "cognate $V_H$ and $V_L$ coding pair" describes an original pair of $V_H$ and $V_L$ coding sequences contained within or derived from the same antibody-producing cell. Thus, a cognate $V_H$ and $V_L$ pair represents the $V_H$ and $V_L$ pairing originally present in the donor from which such a cell is derived. The term "an antibody expressed from a $V_H$ and $V_L$ coding pair" indicates that an antibody or an antibody fragment is produced from a vector, plasmid or other polynucleotide containing the $V_H$ and $V_L$ coding sequence. When a cognate $V_H$ and $V_L$ coding pair is expressed, either as a complete antibody or as a stable fragment thereof, they preserve the binding affinity and specificity of the antibody originally expressed from the cell they are derived from. A library of cognate pairs is also termed a repertoire or collection of cognate pairs, and may be kept individually or pooled.

The term "recombinant antibody" refers to an antibody that is expressed from a cell or cell line transfected with an expression vector (or possibly more than one expression vector, typically two expression vectors) comprising the coding sequence of the antibody, where said coding sequence is not naturally associated with the cell.

As used herein, the term "canonical" residue refers to a residue in a CDR or framework that defines a particular canonical CDR structure as defined by Chothia et al. (J. Mol. Biol., 196: 901-917 (1987); Chothia et al., J. Mol. Biol., 227: 799-817 (1992)). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the term "framework" or "framework sequence" refers to the remaining sequences of a variable region minus the CDRs. Because the exact definition of a CDR sequence can be determined by different systems (for example, see above), the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region.

Human heavy chain and light chain framework (FR) sequences are known in the art that can be used as heavy chain and light chain "acceptor" framework sequences (or simply, "acceptor" sequences) to humanize a non-human antibody using techniques known in the art. In an embodiment of this invention, human heavy chain and light chain acceptor sequences are selected from the framework sequences listed in publicly available databases such as V-base (hypertext transfer protocol://vbase.mrc-cpe.cam.ac.uk/) or in the international IMMUNOGENETICS® (IMGT®) information system (hypertext transfer protocol://imgt.cines.fr/texts/IMGTrepertoire/LocusGenes/). Table 2, below, provides a non-limiting list of examples of human heavy chain acceptor sequences known in the art. Table 3, below, provides a non-limiting list of examples of human light chain acceptor sequences known in the art. In an embodiment of this invention, human heavy chain and light chain acceptor sequences are selected from the amino acid sequences described in Table 2 and Table 3, below, however, other human heavy chain and light acceptors sequences not listed in Table 2 and Table 3 may also be used to humanize an antibody according to this invention.

In one embodiment, heavy chain human acceptor framework sequences from Table 2 for use in generating humanized antibodies that bind ErbB2 according to this invention include a set consisting of the hIGHV1-69 FR1, the hIGHV1-69 FR2, the hIGHV1-69 FR3, and the hIGHJ4 FR4 acceptor sequences; a set consisting of the hIGHV1-46 FR1, the hIGHV1-46 FR2, the hIGHV1-46 FR3, and the hIGHJ4 FR4 acceptor sequences.

In another embodiment, light chain human acceptor framework sequences from Table 3 for use in generating humanized antibodies that bind ErbB2 according to this invention include a set consisting of the hIGKV1-33 FR1, hIGKV1-33 FR2, hIGKV1-33 FR3, and hIGKJ1 FR4 acceptors sequences and a set a consisting of the hIGKV1-27 FR1, hIGKV1-27 FR2, hIGKV1-27 FR3, and hIGKJ1 FR4 acceptor sequences.

In yet another embodiment, a set of human acceptor framework sequences for use in generating a humanized antibody that binds ErbB2 according to the present invention comprises one or more (e.g., any one, two, three, four, five, six, seven, or eight per binding domain) of the acceptor framework sequences selected from the group consisting of:

Heavy chain framework-1 (H-FR1):
(SEQ ID NO: 52)
Q-V-Q-L-V-Q-S-G-A-E-V-K-K-P-G-S-S-V-K-V-S-C-K-

$X_{24}$-S-G-G-T-F-$X_{30}$,

Wherein $X_{24}$ is A or T, $X_{30}$ is S or T;

Heavy chain framework-2 (H-FR2):
(SEQ ID NO: 4)
W-V-R-Q-A-P-G-Q-G-L-E-W-M-G;

Heavy chain framework-3 (H-FR3):
(SEQ ID NO: 53)
R-$X_{67}$-T-I-T-A-D-$X_{73}$-S-T-$X_{76}$-T-A-Y-M-E-L-S-S-L-R-S-

E-D-T-A-V-Y-Y-C-A-R, wherein $X_{67}$ is A or V, $X_{73}$ is K or Q, $X_{76}$ is S or N Heavy chain framework-4 (H-FR4):
(SEQ ID NO: 6)
W-G-Q-G-T-L-V-T-V-S-S Light chain framework-1 (L-FR1):
(SEQ ID NO: 7)
D-I-Q-M-T-Q-S-P-S-S-L-S-A-S-V-G-D-R-V-T-I-T-C;

Light chain framework-2 (L-FR2):
(SEQ ID NO: 54)
W-Y-Q-$X_{38}$-K-P-G-K-G-P-K-L-L-I-Y-$X_{49}$, wherein $X_{38}$ is Q or H, $X_{49}$ is Y or H, Light chain framework-3 (L-FR3):
(SEQ ID NO: 55)
G-$X_{58}$-P-S-R-F-S-G-S-G-S-G-$X_{69}$-D-$X_{71}$-T-$X_{73}$-T-I-S-S-

L-Q-P-E-D-F-A-T-Y-Y-C, wherein $X_{58}$ is I or V, $X_{69}$ is K, T or R, $X_{71}$ is Y or F, $X_{73}$ is L or F;

Light chain framework-4 (LF4):
(SEQ ID NO: 10)
F-G-Q-G-T-K-V-E-I-K.

In a preferred embodiment, an antibody that binds ErbB2 according to the present invention is humanized using a set of human acceptor sequences consisting of an H-FR1, H-FR2, H-FR3, H-FR-4, L-FR1, L-FR2, L-FR3, and L-FR4 acceptor sequence described above.

The term "a combination of antibodies" or "antibody combination" or "antibody mixture" refers to at least two distinct antibodies, having different CDR sequences.

The term "synergistic" as used herein refers to an antibody combination that is more effective than the additive effects of the two or more monoclonal antibodies. The experimental design for the synergism of a drug combination was described by Chou (*Pharmacol Rev* 58:621-681, 2006). The combinations provided by this invention have been evaluated in several assay systems, and the data can be analyzed utilizing a standard program for quantifying synergism, additivism, and antagonism among anticancer agents. The combination therapy may provide "synergy" and prove "synergistic", i.e., the effect achieved when the active ingredients used together, either concurrently or sequentially, is greater than the sum of the effects that results from using the compounds alone. A synergistic effect may be attained when two or more antibodies are: (1) co-formulated and administered or delivered simultaneously in a combined formulation; (2) delivered by alternation as separate formulations; or (3) by some other regimen such as bispecific IgG format.

The term "neutralizing" refers to counteracting the biological activity of an antigen when an antibody specifically binds the antigen. In an embodiment, the neutralizing antibody binds an antigen and neutralizes its biological activity by at least about 20%, 40%, 60%, 80%, 85%, 90%, 95%, or more.

The term "distinct epitopes" refers to the fact that when two different antibodies of this invention bind distinct epitopes preferably less than 80% competition for antigen binding, more preferably less than 50% competition for antigen binding, and most preferably as little competition as possible, such as less than about 25% competition for antigen binding. Antibodies capable of competing with each other for binding to the same antigen may bind the same or overlapping epitopes or may have a binding site in the close vicinity of one another, so that competition is mainly caused by steric hindrance, therefore, the term "same epitope" refers to the fact that when two different antibodies of the present invention bind same epitope preferably more than 80% competition for antigen binding, more preferably more than 85% competition for antigen binding, more preferably more than 90% competition for antigen binding, and most preferably more than 95% competition for antigen binding. An analysis for "distinct epitopes" or "same epitope" of antibody pairs may be performed by methods known in the art, for example, by way of binding experiments under saturating antibody conditions using either FACS (fluorescence activated cell sorting) or other flow cytometry analysis on cells expressing ErbB2 and individual fluorescent labeled antibodies, or by Surface Plasmon Resonance (SPR) using ErbB2 antigen captured or conjugated to a flow cell surface. A method for determining competition between antibodies using SPR is described in the examples.

The term "antibody conjugate" refers to an antibody, chemically linked to a second chemical moiety such as a therapeutic or cytotoxic agent. The term "agent" is used herein to denote a chemical compound, a mixture of chemical compounds, a biological macromolecule, or an extract made from biological materials. Preferably, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone mithramycin, actinomycin D, 1-dehydrotestosterone, glucocorticoids, procaine, tetracaine, lidocaine, propranolol, and puromycin and analogs or homologs thereof.

B. Generation of Trastuzumab-Synergistic Anti-ErbB2 Antibodies

One aspect of the present invention provides isolated mouse monoclonal antibodies that bind to ErbB2 with Trastuzumab-synergistic neutralizing capacity. Another aspect of the present invention provides chimeric antibodies that bind ErbB2. Another aspect of the present invention provides CDR grafted antibodies, or antigen-binding portion thereof, that bind to ErbB2. Another aspect of the present invention provides humanized antibodies, or antigen-binding portions thereof, that bind ErbB2. In an embodiment, the antibodies, or portions thereof, are isolated antibodies or isolated portions thereof. In another embodiment, the antibodies, or antigen-binding portions thereof of the present invention are neutralizing anti-ErbB2 antibodies. Advantageously, such antibodies or antigen-binding portions thereof that bind ErbB2 find use as Trastuzumab functional synergistic partners that can be administered as an individual (human or other mammal). Preferably, the antibodies or antigen-binding portions thereof of the present invention are synergistically inhibiting the growth of ErbB2-positive cancer cell when combining with Trastuzumab.

A description follows as to exemplary techniques for the generation of the antibodies used in accordance with the present invention. The ErbB2 antigen to be used for generation of antibodies may be a soluble form of the extracellular domain of ErbB2. Alternatively, cells expressing ErbB2 at their cell surface (e.g., a carcinoma cell line such as SKBR3 cells, see Stancovski et al. *PNAS* (*USA*) 88:8691-8695 (1991)) can be used to generate antibodies.

(i) Anti-ErbB2 Monoclonal Antibodies Using Hybridoma Technology

Monoclonal antibodies can be prepared using a wide variety of techniques known in the art including the use of hybridoma, recombinant, and phage display technologies, or combination thereof. For example, monoclonal antibodies can be produced using hybridoma techniques including those known in the art and taught, for example, in Harlow et al., *Antibodies: A Laboratory Manual*, second edition, (Cold Spring Harbor Laboratory Press, Cold Spring Harbor, 1988).

After immunization of mice with an ErbB2 antigen or ErbB2-overexpressing cancer cells, antibodies and/or antibody-producing cells may be obtained from the animal. An anti-ErbB2 antibody-containing serum is obtained from the animal by bleeding or sacrificing the animal. The serum may be used as it is obtained from the animal, or the anti-ErbB2 antibodies may be purified from the serum.

Once an immune response is detected (e.g., antibodies specific for the antigen ErbB2) in the mouse serum, the mouse spleen is harvested and splenocytes isolated. The splenocytes are then fused by well-known techniques to any suitable myeloma cells, for example, cells from cell line SP2/0 available from the American Type Culture Collection (ATCC, Manassas, Va., US). The hybridoma clones are then assayed by methods known in the art for cells that secrete antibodies capable of binding to ErbB2. Positive hybridomas are selected and cloned by limited dilution. Ascites fluid, which generally contains high levels of antibodies, can be generated by inoculating mice with positive hybridoma clones.

(ii) Screening for Antibodies with the Trastuzumab-Synergistic Anti-Tumor Bioactivity Techniques for generating antibodies have been described above. The present invention further provides a method of isolating antibody combination containing synergistic bioactivity (such as cell-proliferation inhibition activity). The antibody combination of the present invention contains at least two or more monoclonal antibodies with the following desired properties: <1> they bind to distinct non-overlapping epitope present on ErbB2; <2> they are novel antibodies or part of combination is novel antibodies; <3> the efficacy of the antibody combination (any antibody of the present invention+Trastuzumab) is more potent than either that of each individual component or than the sum of each individual's efficacy. Preferably, the present invention has provided a synergistic combination of two monoclonal antibodies, one of five monoclonal antibodies of this invention and the other Trastuzumab. The anti-tumor activity of such a two-antibody combination is more potent than that of either component or than the sum of each individual's efficacy.

Preferably, to identify an antibody that is capable to synergize with Trastuzumab in inhibiting cell growth of ErbB2-positive cells, the following procedure may be followed: (a) Perform ELISA or cell-based binding to confirm the specific ErbB2 binding activity of antibodies of interest. The ability of the antibody binding to recombinant human ErbB2 and to cells expressing human ErbB2 may be determined. (b) Perform Trastuzumab-based synergistic inhibition of cell proliferation screening. For example, inhibition of BT474 cell growth by individual anti-ErbB2 antibodies and/or antibody combinations may be performed using BT474-based cell proliferation inhibition assay as described in Example 4 below. Anti-ErbB2 monoclonal antibodies or antibody combination may be added to each well and incubated for about 144 hours. Dose response curves may be prepared and an $IC_{50}$ value may be calculated for the antibody of interest or the antibody combination of interest. In one embodiment, the growth inhibitory antibody combination is able to inhibit growth of BT474 cells by about 20-80% higher than that of each individual antibody at the concentration of about 0.5 to 20 µg/ml.

The hypothesized mechanisms for such superior synergistic anti-tumor activity could be, but not limited to, one of the following possibilities: (a) the synergistic cross enhancement by blocking two or more functional epitopes of target (e.g., ErbB2), and/or (b) The avidity or synergistic binding affinity to the target (e.g., ErbB2) of two or more monoclonal antibodies is much higher than the affinity of a single monoclonal antibody, and/or (c) Unlike the antibody-antigen trimer formation of a single monoclonal antibody, the formation of antibody-antigen aggregates mediated by two or more monoclonal antibodies with distinct epitopes may be much bigger and easier for immune system to detect for clearance and/or for cell endocytosis. Based on one of the above mechanism or the combination of the above all, or other possible mechanisms, anti-ErbB2 synergistic antibody combination may be used for prevention or treatment of ErbB2-positive cancer. Preferably, the antibodies of this invention may be used as a combination with Trastuzumab to treat ErbB2-positive cancer or Trastuzumab-resistant ErbB2-positive cancer.

(iii) Production of Recombinant ErbB2 Antibodies

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a eukaryotic host cell, e.g., electroporation, calcium-phosphate precipitation, DEAE-dextran transfection and the like. Exemplary mammalian host cells for expressing the recombinant antibodies of the present invention include Chinese Hamster Ovary (CHO cells) (including dhfr-CHO cells, described in Urlaub and Chasin, Proc. Natl. Acad. Sci. USA, 77: 4216-4220 (1980), used with a DHFR selectable marker, e.g., as described in Kaufman and Sharp, J. Mol. Biol., 159: 1-621 (1982), NSO Myeloma cells, COS cells, and SP2 cells. when recombinant expression vectors encoding an antibody are introduced into mammalian host cells, the antibody is produced by culturing the host cells for a period of time sufficient to allow for expression of the antibody in the host cells or, more preferably, secretion of the antibody into the culture medium in which the host cells are grown. The antibody can be recovered from the culture medium using standard protein purification methods.

Host cells can also be used to produce functional antibody fragments, such as Fab fragments or scFv molecules. It will be understood that variation on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the present invention. In addition, bifunctional antibodies may be produced in which one heavy and one light chain are an antibody of the present invention (i.e., binds human ErbB2) and the other heavy and light chain are specific for an antigen other than human ErbB2 by crosslinking an antibody of the present invention to a second antibody by standard chemical crosslinking methods.

In a preferred system for recombinant expression of an antibody, or antigen-binding portion thereof, of the present invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the present invention provides a method of synthesizing a recombinant antibody of the present invention by culturing a host cell of the present invention in a suitable culture medium until a recombinant antibody of the present invention is synthesized. The method can further comprise isolating the recombinant antibody from the culture medium 1. Anti-ErbB2 Antibodies.

Amino acid sequences of VH and VL regions of isolated mouse monoclonal antibodies that bind human ErbB2 are shown for clones 4C9, 4H2, 4G6, 5F12, and 5G9 in Table 12 (See Example below). The isolated anti-ErbB2 antibody CDR sequences described herein establish a family of ErbB2 antibodies, isolated in accordance with this invention, and comprising polypeptides that include the CDR sequences derived therefrom. Sequences of variable regions and CDRs of the monoclonal antibodies and humanized antibodies derivatives thereof are listed in Tables 12, 16, and 19. To generate and to select CDRs for antibodies according to this invention having preferred ErbB2 binding and/or neutralizing activity with respect to human ErbB2, standard methods known in the art for generating antibodies of the present invention and assessing the ErbB2 binding and/or neutralizing characteristics of those antibody may be used, including but not limited to those specifically described herein Based on an alignment of the amino acid sequences of the CDRs of the heavy chain variable regions (VH) and the light chain variable regions (VL) of the anti-ErbB2 antibody clones described herein, the present invention provides an ErbB2 antibody comprising an antigen binding domain capable of binding human ErbB2, said antigen binding domain comprising at least one or more of the six CDRs, i.e., CDR-H1, CDR-H2, CDR-H3, CDR-L1, CDR-L2, and CDR-L-3, defined below:

CDR-H1 is selected from the group consisting of:
$X_1$-$X_2$-$X_3$-$X_4$-$X_5$ (SEQ ID NO: 11), wherein:
$X_1$ is S
$X_2$ is Y
$X_3$ is T or Y
$X_4$ is M or I
$X_5$ is H
Residues 31-35 of 4C9 CDR-H1 (SEQ ID NO: 17)
Residues 31-35 of 4H2 CDR-H1 (SEQ ID NO: 19)
Residues 31-35 of 4G6 CDR-H1 (SEQ ID NO: 21)
Residues 31-35 of 5F12 CDR-H1 (SEQ ID NO: 23)
Residues 31-35 of 5G9 CDR-H1 (SEQ ID NO: 25)
Residues 31-35 of 5F12 CDR-H2VH.V1 (SEQ ID NO: 27)
Residues 31-35 of 5F12 CDR-H1 VH.1 (SEQ ID NO: 28)
Residues 31-35 of 5F12 CDR-H1 VH.2 (SEQ ID NO: 29)
Residues 31-35 of 5F12 CDR-H1 VH.3 (SEQ ID NO: 30)
Residues 31-35 of 5F12 CDR-H1 VH.4 (SEQ ID NO: 31)
Residues 31-35 of 5G9 CDR-H1 VH.V1 (SEQ ID NO: 39)
Residues 31-35 of 5G9 CDR-H1 VH.1 (SEQ ID NO: 40)
Residues 31-35 of 5G9 CDR-H1 VH.2 (SEQ ID NO: 41)
Residues 31-35 of 5G9 CDR-H1 VH.3 (SEQ ID NO: 42)
Residues 31-35 of 5G9 CDR-H1 VH.4 (SEQ ID NO: 43)
Residues 31-35 of 5G9 CDR-H1 VH.5 (SEQ ID NO: 44)
CDR-H2 is selected from the group consisting of:
$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$ (SEQ ID NO: 12),
wherein:
$X_1$ is Y
$X_2$ is I
$X_3$ is N
$X_4$ is P
$X_5$ is S
$X_6$ is S
$X_7$ is S or D
$X_8$ is Y
$X_9$ is T
$X_{10}$ is A or N
$X_{11}$ is Y
$X_{12}$ is N
$X_{13}$ is Q
$X_{14}$ is K or N
$X_{15}$ is F
$X_{16}$ is K or R
$X_{17}$ is D
Residues 50-66 of 4C9 CDR-H2 (SEQ ID NO: 17)
Residues 50-66 of 4H2 CDR-H2 (SEQ ID NO: 19)
Residues 50-66 of 4G6 CDR-H2 (SEQ ID NO: 21)
Residues 50-66 of 5F12 CDR-H2 (SEQ ID NO: 23)
Residues 50-66 of 5G9 CDR-H2 (SEQ ID NO: 25)
Residues 50-66 of 5F12 CDR-H2VH.V1 (SEQ ID NO: 27)
Residues 50-66 of 5F12 CDR-H2VH.1 (SEQ ID NO: 28)
Residues 50-66 of 5F12 CDR-H2VH.2 (SEQ ID NO: 29)
Residues 50-66 of 5F12 CDR-H2VH.3 (SEQ ID NO: 30)
Residues 50-66 of 5F12 CDR-H2VH.4 (SEQ ID NO: 31)
Residues 50-66 of 5G9 CDR-H1 VH.V1 (SEQ ID NO: 39)
Residues 50-66 of 5G9 CDR-H2VH.1 (SEQ ID NO: 40)
Residues 50-66 of 5G9 CDR-H2VH.2 (SEQ ID NO: 41)
Residues 50-66 of 5G9 CDR-H2VH.3 (SEQ ID NO: 42)
Residues 50-66 of 5G9 CDR-H2VH.4 (SEQ ID NO: 43)
Residues 50-66 of 5G9 CDR-H2VH.5 (SEQ ID NO: 44)

and
CDR-H3 is selected from the group consisting of:
$X_1$-$X_2$-$X_3$-$X_4$-$X_5$-$X_6$-$X_7$-$X_8$-$X_9$ (SEQ ID NO: 13), wherein:
$X_1$ is A
$X_2$ is S
$X_3$ is A or S
$X_4$ is F
$X_5$ is S
$X_6$ is L
$X_7$ is D
$X_8$ is F
$X_9$ is W
Residues 95-103 of 4C9 CDR-H3 (SEQ ID NO: 17)
Residues 95-103 of 4H2 CDR-H3 (SEQ ID NO: 19)
Residues 95-103 of 4G6 CDR-H3 (SEQ ID NO: 21)
Residues 95-103 of 5F12 CDR-H3 (SEQ ID NO: 23)
Residues 95-103 of 5G9 CDR-H3 (SEQ ID NO: 25)
Residues 95-103 of 5F12 CDR-H3VH.V1 (SEQ ID NO: 27)
Residues 95-103 of 5F12 CDR-H3VH.1 (SEQ ID NO: 28)
Residues 95-103 of 5F12 CDR-H3VH.2 (SEQ ID NO: 29)
Residues 95-103 of 5F12 CDR-H3VH.3 (SEQ ID NO: 30)
Residues 95-103 of 5F12 CDR-H3VH.4 (SEQ ID NO: 31)
Residues 95-103 of 5G9 CDR-H1 VH.V1 (SEQ ID NO: 39)
Residues 95-103 of 5G9 CDR-H3VH.1 (SEQ ID NO: 40)
Residues 95-103 of 5G9 CDR-H3VH.2 (SEQ ID NO: 41)
Residues 95-103 of 5G9 CDR-H3VH.3 (SEQ ID NO: 42)
Residues 95-103 of 5G9 CDR-H3VH.4 (SEQ ID NO: 43)
Residues 95-103 of 5G9 CDR-H3VH.5 (SEQ ID NO: 44)
CDR-L1 is selected from the group consisting of:
$X_1$-$X_2$-$X_3$-$X_4$-$X_5$-$X_6$-$X_7$-$X_8$-$X_9$-$X_{10}$-$X_{11}$ (SEQ ID NO: 14), wherein:
$X_1$ is K
$X_2$ is A
$X_3$ is S
$X_4$ is H or Q
$X_5$ is D
$X_6$ is I
$X_7$ is N
$X_8$ is K
$X_9$ is Y
$X_{10}$ is I
$X_{11}$ is A
Residues 24-34 of 4C9 CDR-L1 (SEQ ID NO: 18)
Residues 24-34 of 4H2 CDR-L1 (SEQ ID NO: 20)
Residues 24-34 of 4G6 CDR-L1 (SEQ ID NO: 22)
Residues 24-34 of 5F12 CDR-L1 (SEQ ID NO: 24)
Residues 24-34 of 5G9 CDR-L1 (SEQ ID NO: 26)
Residues 24-34 of 5F12 CDR-L1VL.V1 (SEQ ID NO: 32)
Residues 24-34 of 5F12 CDR-L1VL.1 (SEQ ID NO: 33)
Residues 24-34 of 5F12 CDR-L1VL.2 (SEQ ID NO: 34)
Residues 24-34 of 5F12 CDR-L1VL.3 (SEQ ID NO: 35)
Residues 24-34 of 5F12 CDR-L1VL.4 (SEQ ID NO: 36)
Residues 24-34 of 5F12 CDR-L1VL.5 (SEQ ID NO: 37)
Residues 24-34 of 5F12 CDR-L1VL.6 (SEQ ID NO: 38)
Residues 24-34 of 5G9 CDR-L1VL.V1 (SEQ ID NO: 45)
Residues 24-34 of 5G9 CDR-L1VL.1 (SEQ ID NO: 46)
Residues 24-34 of 5G9 CDR-L1VL.2 (SEQ ID NO: 47)
Residues 24-34 of 5G9 CDR-L1VL.3 (SEQ ID NO: 48)
Residues 24-34 of 5G9 CDR-L1VL.4 (SEQ ID NO: 49)
Residues 24-34 of 5G9 CDR-L1VL.5 (SEQ ID NO: 50)
Residues 24-34 of 5G9 CDR-L1VL.6 (SEQ ID NO: 51)
CDR-L2 is selected from group consisting of:
$X_1$-$X_2$-$X_3$-$X_4$-$X_5$-$X_6$-$X_7$ (SEQ ID NO:15), wherein:
$X_1$ is Y or S
$X_2$ is T
$X_3$ is S
$X_4$ is T
$X_5$ is L
$X_6$ is Q or Y
$X_7$ is P
Residues 50-56 of 4C9 CDR-L2 (SEQ ID NO: 18)
Residues 50-56 of 4H2 CDR-L2 (SEQ ID NO: 20)
Residues 50-56 of 4G6 CDR-L2 (SEQ ID NO: 22)
Residues 50-56 of 5F12 CDR-L2 (SEQ ID NO: 24)
Residues 50-56 of 5G9 CDR-L2 (SEQ ID NO: 26)
Residues 50-56 of 5F12 CDR-L2VL.V1 (SEQ ID NO: 32)
Residues 50-56 of 5F12 CDR-L2VL.1 (SEQ ID NO: 33)
Residues 50-56 of 5F12 CDR-L2VL.2 (SEQ ID NO: 34)
Residues 50-56 of 5F12 CDR-L2VL.3 (SEQ ID NO: 35)
Residues 50-56 of 5F12 CDR-L2VL.4 (SEQ ID NO: 36)
Residues 50-56 of 5F12 CDR-L2VL.5 (SEQ ID NO: 37)
Residues 50-56 of 5F12 CDR-L2VL.6 (SEQ ID NO: 38)
Residues 50-56 of 5G9 CDR-L2VL.V1 (SEQ ID NO: 45)
Residues 50-56 of 5G9 CDR-L2VL.1 (SEQ ID NO: 46)
Residues 50-56 of 5G9 CDR-L2VL.2 (SEQ ID NO: 47)
Residues 50-56 of 5G9 CDR-L2VL.3 (SEQ ID NO: 48)
Residues 50-56 of 5G9 CDR-L2VL.4 (SEQ ID NO: 49)
Residues 50-56 of 5G9 CDR-L2VL.5 (SEQ ID NO: 50)
Residues 50-56 of 5G9 CDR-L2VL.6 (SEQ ID NO: 51)
and
CDR-L3 is selected from the group consisting of:
$X_1$-$X_2$-$X_3$-$X_4$-$X_5$-$X_6$-$X_7$-$X_8$-$X_9$ (SEQ ID NO:16), wherein:
$X_1$ is L
$X_2$ is Q or N
$X_3$ is Y
$X_4$ is D
$X_5$ is N
$X_6$ is L
$X_7$ is L
$X_8$ is W
$X_9$ is T
Residues 89-97 of 4C9 CDR-L3 (SEQ ID NO: 18)
Residues 89-97 of 4H2 CDR-L3 (SEQ ID NO: 20)
Residues 89-97 of 4G6 CDR-L3 (SEQ ID NO: 22)
Residues 89-97 of 5F12 CDR-L3 (SEQ ID NO: 24)
Residues 89-97 of 5G9 CDR-L3 (SEQ ID NO: 26)
Residues 89-97 of 5F12 CDR-L3VL.V1 (SEQ ID NO: 32)
Residues 89-97 of 5F12 CDR-L3VL.1 (SEQ ID NO: 33)
Residues 89-97 of 5F12 CDR-L3VL.2 (SEQ ID NO: 34)
Residues 89-97 of 5F12 CDR-L3VL.3 (SEQ ID NO: 35)
Residues 89-97 of 5F12 CDR-L3VL.4 (SEQ ID NO: 36)
Residues 89-97 of 5F12 CDR-L3VL.5 (SEQ ID NO: 37)
Residues 89-97 of 5F12 CDR-L3VL.6 (SEQ ID NO: 38)
Residues 89-97 of 5G9 CDR-L3VL.V1 (SEQ ID NO: 45)
Residues 89-97 of 5G9 CDR-L3VL.1 (SEQ ID NO: 46)
Residues 89-97 of 5G9 CDR-L3VL.2 (SEQ ID NO: 47)
Residues 89-97 of 5G9 CDR-L3VL.3 (SEQ ID NO: 48)
Residues 89-97 of 5G9 CDR-L3VL.4 (SEQ ID NO: 49)
Residues 89-97 of 5G9 CDR-L3VL.5 (SEQ ID NO: 50)
Residues 89-97 of 5G9 CDR-L3VL.6 (SEQ ID NO: 51)
Preferably, an ErbB2 antibody comprises at least one CDR described above, more preferably any two CDRs described above, more preferably any three CDRs described above, even more preferably any four CDRs described above, still more preferably any five CDRs described above, and most preferably any six CDRs described above (i.e., CDR-H1, CDR-H2, CDR-H3, CDR-L1, CDR-L2, and CDR-L3 as described above). A particularly preferred ErbB2 antibody comprising three CDRs comprises CDR-H1, CDR-H2, and CDR-H3 as described above.

2. Anti-ErbB2 Chimeric Antibodies.

A chimeric antibody is a molecule in which different portions of the antibody are derived from different animal species, such as antibodies having a variable region derived from a murine monoclonal antibody and a human immunoglobulin constant region. See, e.g., Morrison, Science, 229 1202-1207 (1985); Oi et al., BioTechniques, 4: 214 (1986); Gillies et al., J. Immunol. Methods 125: 191-202 (1989) U.S. Pat. Nos. 5,807,715; 4,816,567; and 4,816,397. In addition, techniques developed for the production of "chimeric antibodies" by splicing genes from a mouse antibody molecule of appropriate antigen specificity together with genes from a human antibody molecule of appropriate biological activity can be used. See, for example, Morrison et al., Proc. Natl. Acad. Sci. USA, 81: 6851-6855 (1984); Neuberger et al., Nature, 312: 604-608 (1984); Takeda et al., Nature, 314: 452-454 (1985).

3. Anti-ErbB2 CDR Grafted Antibodies.

The isolated anti-ErbB2 antibody CDR sequences of this invention may be used to make CDR-grafted antibodies to modulate the properties of the original antibody. Such properties include but are not limited to binding kinetics, affinity, biological activities, species cross-reactivity, molecule cross reactivity, epitope, physicochemical properties, pharmacokinetic properties, pharmacodynamic properties, or pharmacological properties. CDR-grafted antibodies comprise heavy and light chain variable region sequences from a human antibody or a non-human primate antibody wherein one or more of the CDR regions of VH and/or VL are replaced with CDR sequences of the original anti-ErbB2 antibody. A framework sequence from any human or non-human primate antibody may serve as the template for CDR grafting. However, straight chain replacement onto such a framework often leads to some loss of binding affinity to the antigen. The more homologous a human, or other species, antibody is to the original human antibody, the less likely the possibility that combining the CDRs with the new human framework or non-human primate framework will introduce distortions in the CDRs that could reduce affinity or other properties. Therefore, it is preferable that the variable framework that is chosen to replace the human variable region framework apart from the CDRs has at least a 30% sequence identity with the human antibody variable region framework. It is more preferable that the variable region framework that is chosen to replace the human variable region framework apart from the CDRs has at least a 40% sequence identity with the human antibody variable region framework. It is more preferable that the variable region framework that is chosen to replace the human variable framework apart from the CDRs has at least a 50% sequence identity with the human antibody variable region framework. It is more preferable that the variable region framework that is chosen to replace the human variable region framework apart from the CDRs has at least a 60% sequence identity with the human antibody variable region framework. It is more preferable that the new human or non-human primate and the original human variable region framework apart from the CDRs has at least 70% sequence identity. It is even more preferable that the new human or non-human primate and the original human variable region framework apart from the CDRs has at least 75% sequence identity. It is most preferable that the new human or non-human primate and the original human variable region framework apart from the CDRs has at least 80% sequence identity. Even using a highly homologous human or non-human primate framework to graft CDRs of the original human anti-ErbB2 antibody, the resulting grafted antibody may still lose binding affinity to antigen to some degree. In this case, to regain the affinity it is necessary to include at least one or more key framework residue(s) substitution of the original antibody to the corresponding position of the newly grafted antibody. Such a key residue may be selected from the group consisting of:

a residue adjacent to a CDR;
a glycosylation site residue;
a rare residue;
a residue capable of interacting with human ErbB2
a canonical residue;
a contact residue between heavy chain variable region and light chain variable region;
a residue within a Vernier zone; and
a residue in a region that overlaps between a Chothia-defined variable heavy chain CDR1 and a Kabat-defined first heavy chain framework.

4. Anti-ErbB2 Humanized Antibodies.

While the compositions of the present invention eliminate the requirement to make humanized antibodies, humanized ErbB2 antibodies may be prepared using compositions of the present invention. Humanized antibodies are antibody molecules from non-human species antibody that binds the desired antigen having one or more complementarity determining regions (CDRs) from the non-human species and framework regions from a human immunoglobulin molecule. Known human Ig sequences are disclosed at web sites available via the world wide web (www.), e.g., ncbi.nlm-.nih.gov/entrez/query.fcgi; atcc.org/phage/hdb.html; sci-quest.com/; abcam.com/; antibodyresource.com/onlinecom-p.html; public.iastate.eduLabout.pedro-/research_tools.html; mgen.uniheidelberg.de/SD/IT/IT.html; whfreeman.com/immunology-/CH05/kuby05.htm; library-.thinkquest.org/12429/Immune/Antibody.html; hhmi.org/grants/lectures/1996/vlab/; path.-cam.ac.uk/.about.mrcV/mikeimages.html; antibodyresource.com/; mcb.harvard.edu/BioLinks-/Immunology.html; immunologylink.com/; pathbox.wustl.eduLabout.hcenter/index.html; bio-tech.u-fl.edu/.about.hcl/; pebio.com/pa/340913-/340913.html; nal.usda.gov/awic/pubs/antibody/; m.ehimeu.acjp/.about.yasuhito-/Elisa.html; biodesign.com/table.asp; icnet.uk/axp/facs/davies/lin-ks.html; biotech.ufl.edu-/.about.fccl/protocol.html; isac-net.org/sites_geo.html; aximtl.imt.uni-marburg.de/.about.rek/AEP-Start.html; baserv.uci.kun.nl/.about.jraats/linksl.html; recab.uni-hd.de/immuno.bme.nwu.edu/; mrc-cpe.cam.ac.uk/imt-doc/public/INTRO.html; ibt.unam.mx/-virN_mice.html; imgt.cnusc.fr:8104/; biochem.ucl.ac.uk/.about.martin/abs/index.html; anti-bodybath.ac.uk/; abgen.cvm.tamu.edu/lab/wwwab-gen.html; unizh.ch/.about.honegger/AHO-seminar/Slide01.html; cryst.bbk.ac.uk/about.ubcgOVs/; nimr.mrc.a-c.uk/CC/ccaewg/ccaewg.htm; path.cam.ac.uk/.about.mrcV/humanisation/TAHHP.html; ibt.unam.mx/vir/structure/stat_aim.-html; biosci.missouri.edu/smithgp/index.html; cryst.bioc.cam.ac.uk/.about.fmolina/Webpages-/Pept/spottech.html; jerini.de/frroducts.htm; patents.ibm.com/ibm.html. Kabat et al., Sequences of Proteins of Immunological Interest, U. S. Dept. Health (1983). Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089 (Queen et al.); Riechmann et al., Nature, 332: 323-327 (1988)). Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature, 321: 522-525 (1986); Verhoeyen et al., Science, 239: 1534-1536 (1988); Sims et al., J. Immunol., 151: 2296-2308 (1993); Chothia and Lesk, J. Mol. Biol., 196: 901-917 (1987); Carter et al., Proc. Natl. Acad. Sci. USA, 89: 4285-4289 (1992); Presta et al, J. Immunol, 151: 2623-2632 (1993); Padlan, Molecular Immunology, 28(4/5): 489-498 (1991); Studnicka et al. Protein Engineering, 7(6): 805-814 (1994); Roguska et al, Proc. Natl. Acad. Sci. USA, 91:969-973 (1994); PCT Publication Nos: WO 91/09967, WO 99/06834 (PCT/US98/16280), WO97/20032 (PCT/US96/18978), WO 92/11272 (PCT/US91/09630), WO 92/03461 (PCT/US91/05939), WO 94/18219 (PCT/US94/01234), WO 92/01047 (PCT/GB91/01134), WO93/06213 (PCT/GB92/01755), WO90/14443, WO90/14424 and WO90/14430; European Publication Nos. EP 0 592 106 EP 0 519 596, and EP 0 239 400; U.S. Pat. Nos. 5,565,332: 5,723,323; 5,976,862; 5,824,514; 5,817,483; 5,814,476: 5,763,192; 5,723,323; 5,766,886; 5,714,352; 6,204,023: 6,180,370; 5,693,762; 5,530,101; 5,585,089; 5,225,539; and 4,816,567.

C. Production of Antibodies and Antibody-Producing Cell Lines

Preferably, anti-ErbB2 antibodies of the present invention exhibit a high capacity to inhibit ErbB2-positive tumor growth activity when combined with Trastuzumab, e.g., as assessed by any one of several in vitro and in vivo assays known in the art. For example, IC50 of the combination of Trastuzumab plus any one of these antibodies of this invention is about 50% of that of each individual antibody in in vitro cell proliferation inhibition assay (Table 11) and/or in in vivo tumor model (Table 23), and in the same in vitro cell-based bioassay, the maximum inhibition capacity of the combination of Trastuzumab plus any one of these antibodies of this invention is in the range of 81% to 95%, in contrast, the maximum inhibition capacity of each individual antibody is in the range of 13% to 70%.

In certain embodiments, the antibody comprises a heavy chain constant region, such as an IgG1, IgG2, IgG3, IgG4, IgA, IgE, IgM, or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

One embodiment provides a labeled antibody wherein an antibody or antibody portion of this invention is derivatized or linked to another functional molecule (e.g., another peptide or protein). For example, a labeled antibody of this invention can be derived by functionally linking an antibody or antibody portion of this invention (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

Useful detectable agents with which an antibody or antibody portion of this invention may be derivatized include fluorescent compounds. Exemplary fluorescent detectable agents include fluorescein, fluorescein isothiocyanate, rhodamine, 5-dimethylamine-1-naphthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

D. Uses of ErbB2 Antibodies (i) Monoclonal Antibodies

Given their ability to bind human ErbB2, the ErbB2 antibodies described herein, including antibodies and portions thereof, can be used to detect or measure ErbB2 in a sample (e.g., in a mixture, solution, or biological sample, such as blood, serum, or plasma), using any of the conventional immunoassays known in the art, such as an enzyme linked immunosorbent assays (ELISA), a radioimmunoassay (RIA), or a tissue immunohistochemistry.

The present invention provides a method for detecting human ErbB2 in a sample comprising contacting a sample with an ErbB2 antibody and detecting either the ErbB2 antibody bound to human ErbB2 or the unbound antibody to thereby detect human ErbB2 in the sample. An ErbB2 antibody described herein can be directly or indirectly labeled with a detectable substance to facilitate detection of the bound or unbound ErbB2 antibody. Suitable detectable substances include various enzymes, prosthetic groups, fluorescent materials, luminescent materials and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm.

Biological samples that can be assayed for ErbB2 include urine, feces, blood, serum, plasma, perspiration, saliva, oral swab (cheek, tongue, throat), vaginal swab, rectal swab, dermal swab, dermal scrape, tissue biopsy, as well as any other tissue sample that can be obtained by methods available in the art.

Alternative to labeling the antibody, human ErbB2 can be assayed in biological fluids by a competition immunoassay utilizing recombinant human (rh) ErbB2 (rhErbB2) standards labeled with a detectable substance and an unlabeled ErbB2 antibody described herein. In this assay, the biological sample, the labeled (rhErbB2) standards, and the ErbB2 antibody are combined and the amount of labeled rhErbB2 standard bound to the unlabeled antibody is determined. The amount of human ErbB2 in the biological sample is inversely proportional to the amount of labeled rhERBB2 standard bound to the ErbB2 antibody. Similarly, human ErbB2 can also be assayed in biological fluids by a competition immunoassay utilizing rhErbB2 standards labeled with a detectable substance and an unlabeled ErbB2 antibody described herein.

The ErbB2 antibodies of this invention preferably are capable of neutralizing ErbB2 activity, in particularly human ErbB2 activity, both in vitro and in vivo. Accordingly, such antibodies of this invention can be used to inhibit ErbB2 activity, e.g., in a cell culture containing ErbB2, in human subjects, or in other mammalian subjects expressing an ErbB2 with which an antibody of this invention cross-reacts. In one embodiment, this invention provides a method for inhibiting ErbB2 activity comprising contacting an ErbB2 with an ErbB2 antibody or antibody portion of this invention such that ErbB2 activity is inhibited. For example, in a cell culture containing or suspected of containing ErbB2, an antibody or antibody portion of this invention can be added to the culture medium to inhibit ErbB2 activity in the culture.

In another embodiment, this invention provides a method for neutralizing ErbB2 activity in a subject, advantageously from a subject suffering from a disease or disorder in which ErbB2 or ErbB2 activity is detrimental. The present invention provides methods for neutralizing ErbB2 or ErbB2 activity in a subject suffering from such a disease or disorder, which method comprises administering to the subject an ErbB2 antibody of the present invention such that ErbB2 or ErbB2 activity in the subject is neutralized. Preferably, the ErbB2 is human ErbB2, and the subject is a human subject. Alternatively, the subject can be a mammal expressing an ErbB2 to which an ErbB2 antibody of the present invention is capable of binding. Still further, the subject can be a mammal into which ErbB2 has been introduced (e.g., by administration of ErbB2 or by expression of an ErbB2 transgene). An antibody or other ErbB2 antibody of the present invention can be administered to a human subject for therapeutic purposes. Moreover, an ErbB2 antibody of the present invention can be administered to a non-human mammal expressing an ErbB2 with which the antibody is capable of binding for veterinary purposes or as an animal model of human disease. Regarding the latter, such animal models may be useful for evaluating the therapeutic efficacy of antibodies and other ErbB2 antibodies of the present invention (e.g., testing of dosages and time courses of administration).

(ii) Bispecific Antibodies

Bispecific antibodies are antibodies that have binding specificities for at least two different epitopes. Exemplary bispecific antibodies may bind to two different epitopes of the ErbB2 protein. Other such antibodies may combine an ErbB2 binding site(s) for EGFR, ErbB3 and/or ErbB4. Alternatively, an anti-ErbB2 arm may be combined with an arm that binds to a triggering molecule on a leukocyte such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the ErbB2-expressing cell. Bispecific antibodies may also be used to localize cytotoxic agents to cells which express ErbB2. These antibodies possess an ErbB2-binding arm and an arm which binds the cytotoxic agent (e.g., saporin, anti-interferon-α, vinca alkaloid, ricin A chain, methotrexate or radioactive isotope hapten). Bispecific antibodies can be prepared as full-length antibodies or antibody fragments (e.g., F(ab')2 bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO 98/02463. U.S. Pat. No. 5,821,337 teaches a bispecific anti-ErbB2/anti-CD3 antibody.

Methods for making bispecific antibodies are known in the art. Traditional production of full-length bispecific antibodies is based on the co-expression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986). According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments for *E. coli*, which can be chemically coupled to form bispecific antibodies. Shalaby et al., *J. Exp. Med.*, 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147:60 (1991).

(iii) Immunoconjugates

Another option for therapeutic use of the antibodies and compositions of the present invention is in the form of immunoconjugates, i.e., antibodies conjugated to one or more anti-cancer agents. In particular in the case of compositions comprising two or more individual antibodies of the present invention that bind distinct ErbB2 epitopes, it is contemplated that this may generate a cross-linked antibody-receptor lattice on the cell surface, thereby potentially resulting in an increased level of receptor internalization as compared to the use of a single monoclonal antibody. Conjugation of one or more of the individual antibodies of such a composition to one or more anti-cancer agents therefore has the potential to specifically and effectively deliver the conjugated anti-cancer agents to the interior of tumor cells, thereby augmenting the effect of the anti-ErbB2 antibodies of the present invention to provide an improved tumor cell-killing activity.

Various types of anti-cancer agents may be conjugated to the antibodies of the present invention, including cytotoxic agents (including conventional chemotherapy agents and other small molecule anti-cancer drugs), cytokines (in which case the conjugate may be termed an "immunocytokine"), toxins (in which case the conjugate may be termed an "immunotoxin") and radionuclides, and a few immunoconjugates have already been approved for clinical use. These include ZEVALIN® (a murine anti-CD20 antibody conjugated to $^{90}$Y), BEXXAR® (a murine anti-CD20 antibody conjugated to $^{131}$I) and MYLOTARG® (a humanized anti-CD33 antibody conjugated to calicheamicin). Other immunoconjugates that have been tested in clinical trials include antibodies conjugated to e.g., doxorubicin or a maytansinoid compound. Immunotoxins that have been tested in clinical trials include several antibodies conjugated to a truncated *Pseudomonas* exotoxin A. An immunocytokine comprising a humanized EpCAM antibody conjugated to IL-2 has also been tested.

In the case of antibodies of the present invention conjugated to cytotoxic agents, these may, for example, belong to any of the major classes of chemotherapy drugs, including alkylating agents (e.g., carboplatin, cisplatin, oxaliplatin), antimetabolites (e.g., methotrexate, capecitabine, gemcitabine), anthracyclines (e.g., bleomycin, doxorubicin, mitomycin-C) and plant alkaloids (e.g., taxanes such as docetaxel and paclitaxel, and *vinca* alkaloids such as vinblastine, vincristine and vinorelbine). Since the use of immunoconjugates specifically directs the anti-cancer agent to the tumors, and in particular to the interior of the tumor cells subsequent to internalization, immunoconjugates based on the anti-ErbB2 antibodies of the present invention may advantageously be based on highly cytotoxic agents such as calicheamicin or maytansine derivatives, or on toxins such as bacterial toxins (e.g., *Pseudomonas* exotoxin A, diphtheria toxin) or plant toxins (e.g., ricin).

The conjugated anti-cancer agent in an immunoconjugate is generally linked to the antibody by means of a labile linker that is relatively stable in serum but which allows release of the agent when the immunoconjugate is internalized into the target cell. Suitable linkers include, for example, chemical linkers that are stable at neutral pH in serum but are subjected to acid hydrolysis in the mildly acidic conditions within the lysosomes subsequent to internalization, disulfide linkers that are cleaved by intracellular thiols, and peptide linkers that are stable in serum but which are subjected to enzymatic cleavage in intracellular compartments.

Various conjugation arrangements can be envisioned in compositions containing two or more antibodies of the present invention. For example, with two antibodies it would be possible to conjugate the antibodies to two or more different anti-cancer drugs or to conjugate one antibody to a prodrug which is activated by an agent such as an enzyme conjugated to the other antibody. The general concept of antibody-directed enzyme prodrug therapy (ADEPT) has been described for monoclonal antibodies, where a prodrug is activated by an enzyme targeted to the tumor by a mAB-enzyme conjugate, but the present invention may provide an opportunity for tailoring this approach to particular conditions. It may thus be possible to specifically increase tumor cell killing while sparing or reducing damage to normal tissues.

For further information on anti-cancer immunoconjugates, see Wu et al. (2005) *Nature Biotechnology* 23(9): 1137-1146; Schrama et al. (2006) *Nature Reviews/Drug Discovery* 5:147-159; and Rohrer (2009) *chimica oggi/ Chemistry Today* 27(5):56-60.

(ivi) Dose and Route of Administration

The antibodies and compositions of the present invention will be administered in an effective amount for treatment of the condition in question, i.e., at dosages and for periods of time necessary to achieve a desired result. A therapeutically effective amount may vary according to factors such as the particular condition being treated, the age, sex and weight of the patient, and whether the anti-ErbB2 antibodies are being administered as a stand-alone treatment or in combination with one or more additional anti-cancer treatments.

An effective amount for tumor therapy may be measured by its ability to stabilize disease progression and/or ameliorate symptoms in a patient, and preferably to reverse disease progression, e.g., by reducing tumor size. The ability of an antibody or composition of the present invention to inhibit cancer may be evaluated by in vitro assays, e.g., as described in the examples, as well as in suitable animal models that are predictive of the efficacy in human tumors. Suitable dosage regimens will be selected in order to provide an optimum therapeutic response in each particular situation, for example, administered as a single bolus or as a continuous infusion, and with possible adjustment of the dosage as indicated by the exigencies of each case.

While specific dosing for antibodies in accordance with the present invention has not yet been determined, certain dosing considerations can be determined through compari son with a similar product (an anti-ErbB2 monoclonal antibody) that has been approved for therapeutic use. It is thus contemplated that an appropriate dosage of an antibody composition of the present invention will be similar to the recommended dosage for the anti-ErbB2 monoclonal antibody Trastuzumab (HERCEPTIN®). Depending on the particular condition, Trastuzumab is administered (by way of infusion) for treatment of breast cancer at either an initial dose of 4 mg/kg and subsequent weekly doses of 2 mg/kg, or an initial dose of 8 mg/kg and subsequent doses of 6 mg/kg every three weeks.

It is contemplated that a suitable dose of an antibody composition of the present invention will be in the range of about 0.1-100 mg/kg, 0.5-50 mg/kg or 1-20 mg/kg. The antibody composition may be administered in a dosage of at least 0.25, 0.5, 1, 1.5, 2, 3, 4 or 5 mg/kg; and/or up to about 50, 30, 20 or 15 mg/kg. Administration will normally be repeated at suitable intervals, e.g., once every week, once every two weeks, once every three weeks, or once every four weeks, and for as long as deemed appropriate by the responsible doctor, who may optionally increase or decrease the dosage as necessary.

Three distinct delivery approaches are contemplated for delivery of the antibodies of the present invention. Conventional intravenous delivery will presumably be the standard delivery technique for the majority of tumors. However, in connection with tumors in the peritoneal cavity, such as tumors of the ovaries, biliary duct, other ducts, and the like, intraperitoneal administration may prove favorable for obtaining high dose of antibody at the tumor and to minimize antibody clearance. Similarly, certain solid tumors possess vasculature that is appropriate for regional perfusion. Regional perfusion may allow the obtainment of a high dose of the antibody at the site of a tumor and minimize short-term clearance of the antibody.

As with any protein or antibody infusion-based therapeutic product, safety concerns are related primarily to (i) cytokine release syndrome, i.e., hypotension, fever, shaking, chills, (ii) the development of an immunogenic response to the protein (i.e., development of human antibodies by the patient to the recombinant antibody product), and (iii) toxicity to normal cells that express the ErbB2 receptor, for example, many epithelial cells. Standard tests and follow-up procedures are utilized to monitor any such safety concerns.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

EXAMPLES

Example 1. Generation of Mouse Anti-ErbB2 Monoclonal Antibodies Using Hybridoma Technology Mice were immunized according to the methods known in the art (for example, E Harlow, D. Lane, *Antibody: A Laboratory Manual*, (Cold Spring Harbor Laboratory Press, Cold Spring Harbor, N.Y., 1998).

A human HER2-positive cell line BT474 as well as recombinant human ErbB2 extracellular domain (ErbB2-ECD) protein was used as an immunogen. Human cell lines expressing either high-level human ErbB2 (SK-BR3 cells)

or low-level human ErbB2 (MCF7) were used for determining anti-sera titer and for screening hybridomas secreting antigen-specific antibodies.

Immunizing dosages contained $1 \times 10^6$ BT474 cells/mouse/injection for both primary and boost immunizations. To increase immune response to mouse ErbB2, the mice were further boosted with recombinant mouse ErbB2-ECD in emulsion form with an incomplete Freud's adjuvant (Sigma, St. Louis, Mo., US). Briefly, adjuvant-antigen mixture was prepared by gently mixing the adjuvant in a vial using a vortex. The desired amount of adjuvant was removed from the vial and put into an autoclaved 1.5 mL microcentrifuge tube. The antigen was prepared in PBS or saline with concentration ranging from 0.5-1.0 mg/ml. The calculated amount of antigen was then added to the microcentrifuge tube with the adjuvant, and the solution was mixed by gently vortexing for 2 minutes to generate water-in-oil emulsion. The adjuvant-antigen solution was then drawn into the proper syringe for animal injection. A total of 50 μg of antigen was injected in a volume of 50-100 ul. Each animal was immunized, and then boosted for 2 to 3 times depending on their titer.

Animals with good titers (greater than 30,000 times dilution) were given a final subcutaneous boost with BT474 expressing human ErbB2 or with 25 ug of recombinant human ErbB2-ECD before fusion.

Hybridoma Fusion and ELISA Screening

SP2/0 cells (ATCC CRL-1581) were cultured to reach the log phase stage right before fusion. Immunized mouse spleen cells were prepared sterilely and fused with SP2/0 cells according to the methods known in the art (for example, Kohler G, and Milstein C, "Continuous cultures of fused cell secreting antibody of predefined specificity," Nature, 256: 495-497 (1975)). Fused "hybrid cells" were subsequently dispensed into 96-well plates in DMEM/20% FCS/HAT media. Surviving hybridoma colonies were observed under the microscope seven to ten days postfusion, and subsequently the supernatant from each well was subjected to hybridoma screening using ELISA format according the following procedure: <1> ELISA plates were coated with 50 ul of human ErbB2 (2.0 μg/ml in PBS) overnight at 4° C.; <2> Plates were washed 3 times with 250 ul PBS/0.5% Tween20 and blocked with 200 ul blocking buffer (2% BSA in PBS with 0.5% Tween20); <3> Diluted sera or hybridoma supernatant (100 ul) was added to each well, and incubated at room temperature for 1 hour; <4> Plates were then washed 3 times with PBS/0.5% Tween20, goat anti-mouse-IgG-HRP was used for detection, and binding ODs were observed at 450 nm. Positive hybridomas secreting antibody that binds to recombinant human ErbB2-ECD were then selected and transferred to new 96-well plates for subsequent cell-based binding screening. Fusions of this invention generated about 30000~40000 HAT-resistant surviving hybridomas, resulting 1415 positive hybridomas that specifically bind to recombinant human ErbB2-ECD protein. One plate of such hybridoma screening is illustrated as Table 4 below, with positive hybridomas are underlined and italicized.

Example 2. Cell-Based Screening for Antibodies with High-Ratio of Differential Binding Activity for Cell Membrane ErbB2

Upon the completion of ELISA screening in Example 1, ErbB-positive hybridomas were transferred to new 69-well plates and fed with fresh DMEM medium without HAT selection, three to five days later, the hybridoma medium were subjected to cell-binding screening. Briefly, SK-BR3 cells (ATCC #HTB-30, high-level ErbB2) or MCF7 cells (ATCC #HTB-30, low-level ErbB2) were dispensed into a 96-well (round bottom) plate at $1 \sim 5 \times 10^5$ cells/well and incubated with hybridoma supernatant (50 ul) at 4° C. for 1 hour. Cells were then washed 3 times with FACS buffer (PBS pH 7.2 with 2% FBS) and re-suspended in 100 ul goat anti-mouse IgG-F(ab)$_2$-Alexa (JIR #: 115-545-006). After incubation at 4° C. for 1 hour, cells were then washed 3 times with FACS buffer (PBS pH 7.2 with 2% FBS) and then re-suspended in FACS buffer followed binding signal collection and analysis by FACS instrument (FACSCalibur™ Flow Cytometer, BD Biosciences). The binding signal of the same hybridoma supernatant to SK-BR3 cells and to MCF7 cell was calculated and the ratio of SK-BR3-binding/MCF7-binding was further calculated. Among 1415 positive hybridomas from the above ELISA screening, the top 672 hybridomas with the higher ratio of SK-BR3-binding/MCF7-binding clones (such as clone A2, clone A7, clone A11, clone B2, clone B5, clone B7, clone B9 and so on) were isolated as positive clones for cell banking and subsequent functional screening. One plate of such cell-binding screening is illustrated as Table 5 below.

Upon the completion of cell-based screening, the top 672 hybridomas with high-ranking ratio of SK-BR3/MCF7 were transferred to new 96-well plates. After culturing for 3-5 days, the hybridoma medium of each well was collected for subsequent epitope grouping and cell-based functional screening and the corresponding cells were frozen in liquid nitrogen for long-term storage.

Example 3. Epitope Grouping of Hybridoma Supernatants Based on Competition with Trastuzumab Based on the positive hybridoma cells from cell-binding screening in Example 2, the hybridoma supernatant of each cell line was further evaluated with benchmark antibody (e.g., Trastuzumab and/or Pertuzumab) based epitope grouping to divided the antibodies of the present invention into two categories: benchmark competitive group and benchmark non-competitive group. Briefly, 96-well ELISA plates were coated with recombinant human ErbB2-ECD (0.1 ug/ml) and incubated at 4° C. for overnight. Remove the coating solution by discarding and tapping gently on a filter paper and add 200 ul/well blocking buffer, incubate 2h at 37° C. Add 50 ul antibody of interest, and incubate at 37° C. for 30 minutes followed by adding 50 ul 0.03 ug/ml biotin-labeled benchmark antibody (e.g., biotin-Trastuzumab, or biotin-Pertuzumab) and incubate at 37° C. for additional 30 minutes, then washing the plates with PBST 3 times. Add 100 ul/well of Streptavidin-HRP (1:5000), incubate at 37° C. for 30 minutes. Wash for 3 times with PB ST. Add 100 ul/well of TMB substrate and incubate at room temperature for 15 minutes. Add 50 ul/well of 1N HCl to terminate reaction. Read the plate with Microplate Reader at 450 nm wavelength. Table 6 below illustrates the Trastuzumab competitive ELISA results. In Table 6, F7 well is normal human IgG (as control), G7 well is normal mouse IgG (as control), H7 well is benchmark control (i.e., Trastuzumab, 5 ug/ml). As shown in the Table 6, Trastuzumab, but not human IgG or mouse IgG, block the ErbB2-ECD binding ability of biotin-Trastuzumab. Similarly, sample C6, C7, D2, D3, D4, and H1~H6 (bold, italic and underlined) show certain inhibitory activity, indicating they bind to the same or overlapping epitope as Trastuzumab-epitope. The rest samples (such as A1~A7) in this plate do not inhibit Trastuzumab binding activity to recombinant human ErbB2-ECD, indicating that these antibodies bind to epitopes distinct from Trastuzumab-epitope. Based on Trastuzumab-epitope competitive grouping, the present invention successfully identified ErbB2 antibodies that binds distinct epitopes from Trastuzumab-binding epitope.

Example 4. Trastuzumab-Based Screening of Antibodies with Synergistic Bioactivity Different from standard approach, the present invention undertook a large-scale Trastuzumab-based synergistic bioactivity screening in the early stage. For the antigen positive hybridomas isolated from Example 2, the cell culture supernatant of each hybridoma was further screened for its Trastuzumab-synergistic potency of inhibiting cell proliferation of BT474 breast cancer cells and/or MDA-MB-VII175 cells. Briefly, Seed cells into plates with 100 ul medium at 2000 cells/well. On the next day of cell seeding, aspirate 40 ul cell culture medium followed by adding 60 ul antibody samples including benchmark antibody (Trastuzumab, Pertuzumab, and the combination of Trastuzumab+Pertuzumab), individual hybridoma supernatants from Example 2, and the combination of Trastuzumab and each individual hybridoma supernatants from Example 2. Continue culturing cells for 120-144 hours. Add CellTiter Glo for 10 minutes. Testing cell culture plates were analyzed by SpectraMax M5 plate-reader. Preferably, to screen out hybridoma supernatants that synergistically promote Trastuzumab's inhibition of cell proliferation, a set of samples of interest includes: (a) Trastuzumab-Only Activity group (HOA); (b) Pertuzumab-Only Activity group (POA); (c) Trastuzumab/Pertuzumab (50% Trastuzumab/50% Pertuzumab) Combination group (HPC); (d) Mab Independent Activity group (MIA): Hybridoma supernatant sample in testing; (e) Trastuzumab-Synergistic Activity group (HSA): Trastuzumab+Hybridoma supernatant sample in testing; (f) Negative Control group (NC): human IgG+mouse IgG. The criteria for selecting Trastuzumab-synergistic candidates are based on the following: under the same condition, if the cell proliferation inhibitory activity of HSA is higher than that of HOA or MIA and higher than 50% of the sum of HOA+MIA, then the sample in testing contains Trastuzumab-synergistic bioactivity in cell proliferation inhibition assay. Preferably, under the same cell culture condition, if the cell proliferation inhibitory activity of HSA is higher than that of HPC (Trastuzumab/Pertuzumab group), then the sample in testing is considered exhibiting higher Trastuzumab-synergistic bioactivity than that of Pertuzumab. Following the above screening, the top 672 hybridoma supernatants from Example 2 were evaluated and ranked for their Trastuzumab-synergistic bioactivity of cell proliferation inhibition, and the top 15 candidates were subcloned by limiting dilution to ensure the clonality of each cell line. Among them, five hybridoma cell lines (4C9, 4H2, 4G6, 5F12, and 5G9) as examples were used for antibody production, and the corresponding purified IgGs were further confirmed for their Trastuzumab-synergistic bioactivity following the above protocol. The results are summarized in Example 5 Table 11.

Example 5. Biochemical Characteristics of Antibodies of this Invention

ErbB2-Binding Activity Confirmation of Purified IgGs of this Invention

The corresponding purified IgG of five antibodies of this invention were subjected to SDS-PAGE analysis and the results were shown in FIG. 1. All five antibodies are isotyped to be IgG1/κ that are capable to bind recombinant ErbB2-ECD and ErbB2-positive cells (see Table 7 below).

ErbB2-Binding EC50 of Antibodies of this Invention

The corresponding purified IgG of five antibodies of this invention were also evaluated for their binding activity to recombinant human ErbB2 by capture ELISA. The procedure is briefly described as following: The 96-well plates were coated with 0.5 µg/ml anti-ErbB2 antibody overnight, blocked by 1% BSA in PBST at 37° C. for one hour. Add serial diluted sample of biotin-human ErbB2-ECD started with 2 µg/ml with 1:5 serial dilution. Wash the plate 3 times with PBST and add 100 ul of HRP-streptavidin (1:5000) to each well. Incubate for another 40 min at 37° C. Wash the plate 3 times with PBST and add 100 ul/well of TMB to develop at RT for 15 min followed by quenching with 50 ul 1N HCl. Read the plates at 450 nm for OD's value. Calculate the binding EC50 by using Prism software and the results are in Table 8 below Binding Ability of Antibodies of this Invention to ErbB2 Derived from Different Species Using indirect ELISA described in Example 1, the binding activity of antibodies of this invention to recombinant ErbB2-ECD derived from different species such as mouse, rat, *Macaca mulatta, Macaca fascicularis* and human, was examined. Briefly, Coat 96-well ELISA plates with 1 ug/ml recombinant ErbB2-ECD of different species with 100 ul/well and incubate at 4° C. for overnight. Remove the coating solution by discarding and tapping gently on a filter paper. Add 200 ul/well blocking buffer, incubate at 37° C. for 1-2 hours. Add purified antibody of this invention and incubate at 37° C. for one hour. Wash the plate 3 times with PBST, add goat anti-mouse IgG-HRP 100 ul/well, incubate at 37° C. for one hour. Wash the plate 3 times with PBST, add 100 ul/well TMB after 15 min, add 50 ul/well 1N HCl. Read the plate with Microplate Reader at 450 nm wavelength. The results are summarized in Table 9 below indicating five antibodies of this invention are cross-reactive to recombinant ErbB2 derived from *Macaca mulatta, Macaca fascicularis*, but not to rat and mouse counterparts.

Epitope Grouping of Purified Antibodies of this Invention

Different from the method described in Example 3, epitope grouping of purified antibodies was evaluated by capture ELISA following competitive ELISA. <1> Capture ELISA was performed to determine the concentration of binding EC80 of biotin-labelled recombinant ErbB2-ECD. Briefly, 96-well plate was coated with 0.5 µg/ml anti-ErbB2 antibody overnight, blocked by 1% BSA in PBST for 1 hour at 37° C. Wash the plate 3 times with PBST and add 100 ul of HRP-streptavidin (1:5000) to each well. Incubate for another 40 minutes at 37° C. Wash the plate 3 times with PBST and add 100 ul/well of TMB to develop at RT for 15 min followed by quenching with 50 ul 1N HCl. Read the plates at 450 nm for OD's value to obtain EC80 concentration of biotin-labelled recombinant ErbB2-ECD to each test antibody; <2> Competitive ELISA was performed to determine whether two antibodies bind to the distinct epitope or same epitope. The higher of cross-competition capability of two antibodies binding to the antigen, the more same epitope of the two antibodies (or the less likely-hood of distinct epitope of two test antibodies). Briefly, 96-well plate was coated following the same procedure as above. Add pre-incubated mixture of ErbB2-ECD-biotin with concentration of EC80 and 10 µg/ml test antibodies into plates, incubate for 1 hour. Wash the plate 3 times with PB ST and add 100 µl of HRP-streptavidin (1:5000) to each well. Incubate for another 40 minutes at 37° C. Follow the same procedure as in capture ELISA above to obtain OD450 value and calculate cross-competition capability. Two antibodies are considered to bind the same epitope when their cross-competition capability is not less than 80%. Shown in Table 10, 4C9, 4H2, 4G6, 5F12, and 5G9 exhibit strong cross-competition capability among each other, but do not compete with either Trastuzumab or Pertuzumab in binding to ErbB2-ECD, indicating the antibodies of this invention bind to the same epitope or highly-overlapping epitopes, but distinct from Trastuzumab-epitope or Pertuzumab epitope.

Trastuzumab-Synergistic Bioactivity of Antibodies of this Invention

By using the method described in Example 4, the Trastuzumab-synergistic bioactivity of the purified antibodies (4C9, 4H2, 4G6, 5F12, and 5G9) isolated by this invention were evaluated by BT-474 cell proliferation inhibition assay. The results (See FIGS. 2A-2E and Table 11) demonstrated that antibodies of this invention exhibit certain inhibitory activity of cell proliferation, but exhibit strong synergistic inhibitory activity when combining with Trastuzumab. The cell proliferation inhibition activity of Trastuzumab plus antibodies of this invention is higher than that of Trastuzumab and Pertuzumab, a known combination used in clinics.

Example 6. Deduction of Variable Region Protein Sequences of Anti-ErbB2 Monoclonal Antibodies by DNA Cloning and Sequencing Total RNA was extracted from hybridoma cell pellets using Trizol reagent (Invitrogen, 15596), using the following protocol. 1 ml of Trizol reagent was added to disrupt cells (approximately 1×10$^7$ cells prepared in DPBS) and incubate at room temperature for 5 minutes. Add 200 ul of chloroform. Shake vigorously for 15 seconds. Incubate at room temperature for 3 minutes. Centrifuge at 12,000×g for 15 minutes at 4° C. Transfer aqueous phase to new 1.5 ml centrifuge tube. Add 500 ul of isopropyl alcohol. Incubate at room temperature for 10 minutes. Centrifuge at 12,000×g for 10 minutes at 4° C. Wash with 1 ml 75% ethanol. Centrifuge at 7500 rpm for 5 minutes at 4° C. Air dry for 10 minutes. Resuspend in 40 ul of DEPC-treated water. Incubate at 55° C. for 10 minutes. Measure A260 on Nanodrop.

Subsequently, 2 ug of total RNA were used to synthesize first-strand cDNA using SuperScript III First-Strand Synthesis SuperMix (Invitrogen, 18080-400) according to following protocol:

| Component | Amount (µl) |
| --- | --- |
| Total RNA | 1 |
| Oligo(dT)$_{20}$ | 1 |
| Annealing Buffer | 1 |
| RNase/DNase-free water | ~8 |

Incubate in a thermal cycler at 65° C. for 5 minutes, and then immediately place on ice for 2 minute. Add the following to the tube on ice: 10 µl 2× First-Strand Reaction Mix and 2 µl SuperScriptR III/RNase OUT™ Enzyme Mix. Mix the sample by vortex followed briefly centrifugation. Incubate 50 minutes at 50° C. Terminate the reactions at 85° C. for 5 minutes. Chill on ice. The resultant cDNA was then used as template for PCR amplification of variable regions of antibodies. PCR was performed using first-strand cDNA, primers from Mouse Ig-Primer Set (Novagen, catalog #69831-3) and PLATINUM® Taq DNA Polymerase High Fidelity (Invitrogen, 11304). To amplify heavy chain variable regions, PCR samples were assembled as follows: 27 µl PCR Super Mix+1 µl reverse primer MuIgG V$_H$3'-2+1 µl cDNA+1 µl MuIg-5' leader primer. To amplify light chain variable regions PCR samples were assembled as follows: 27 µl PCR Super Mix+0.25 µl reverse primer MuIgK V$_L$3'-1+1 µl cDNA+1 µl MuIg-5' leader primer.

For reactions with leader primers VH-A, VH-B, VL-A and VL-B use the following PCR cycles: Step 1—Denature 94° C. 2 min; Step 2—Denature 94° C. 30 sec; Step 3—Anneal 50° C. 30 sec.; Step 4—Extend 72° C. 1 min.; 35 cycles, steps 2 through 4; Step 5—Final extension 72° C. 5 min.; Step 6—Cool 4° C. forever.

For reactions with leader primers VH-C through VH-F, and VL-C through VL-G use the following PCR cycles: Step 1—Denature 94° C. 2 min.; Step 2—Denature 94° C. 30 sec.; Step 3—Anneal 60° C. 30 sec.; Step 4—Extend 72° C. 1 min.; 35 cycles, steps 2 through 4; Step 5—Final extension 72° C. 5 min.; Step 6—Cool 4° C. forever.

PCR products were run on 1.2% agarose gel, and bands migrating at the expected size (400-500 bp) were excised for DNA extraction. DNA was purified using QIAquick Gel Extraction Kit (Qiagen, catalog #28704) according to the following protocol: gel slices were weighed. 3 volumes of buffer QG to 1 volume of gel were added to each gel slice. Samples were incubated at 50° C. for 10 minutes until gel slices were completely dissolved, mixing every 2-3 minutes. One gel volume of isopropanol was then added to each sample and mixed. Samples were then applied to QIAquick column and centrifuged for 1 minute at 13000 rpm. To wash, 750 ul of buffer PE were added to samples and spun for 1 minute at 13000 rpm. Columns were then centrifuged for an additional minute at 13,000 rpm to completely remove residual ethanol. DNA was eluted by adding 30 µl of H2O to each column and by spinning 1 minute at 13,000 rpm. Purified PCR products were then sequenced to identify variable region sequences (Table 12, below).

Example 7. Generation and Characterization of Chimeric Antibodies

The variable domains of the heavy and light chain of the anti-ErbB2 monoclonal antibodies (Table 12, above) were cloned in-frame to human IgG1 heavy-chain and kappa light-chain constant regions, respectively. The activities of the resulting chimeric antibodies were confirmed in capture ELISA assays (Table 13, below), and were comparable to their parental mouse monoclonal antibodies.

Following the same method described in Example 5, the binding activity of the chimeric antibodies of this invention was examined for binding recombinant ErbB2-ECD derived from different species such as mouse, rat, *Macaca mulatta*, *Macaca fascicularis* and human. The results were shown in Table 14 below.

Confirmation of Trastuzumab-Synergistic Bioactivity of Chimeric Antibodies

Following the same procedure as described in Example 5, the corresponding chimeric antibodies were evaluated for their Trastuzumab-synergistic potency of inhibiting cell proliferation of BT474 breast cancer cells. The results are summarized in Table 15.

Example 8. Humanization of Anti-ErbB2 Mouse Monoclonal Antibody 5F12

5F12 mouse anti-ErbB2 antibody (Table 12, above) was humanized. Humanized variant amino acid sequences VH.v1, VH.1, VH.2, VH.3, VH.4, VL.v1, VL.1, VL.2, VL.3, VL.4, VL.5, VL.6 (Table 16, below) were converted to DNA sequence based on the most homologous human germlines and synthesized. For the heavy chain variants, human germline heavy chain acceptor sequences hIGHV1-46 FR1, hIGHV1-46 FR2, hIGHV1-46 FR3, and hIGHJ4 FR4 were used (see, Table 2, above). For light chain variants VL.1, VL.1a, and VL.1b, human germline light chain acceptor sequences hIGKV1-33 FR1, hIGKV1-33 FR2, hIGKV1-33 FR3, and hIGKJ1 FR4 were used (see, Table 3, above). Individual constructs were sequence verified to check for accuracy. Positive variants were then inoculated into 250 mls Luria broth plus ampicillin and cultured overnight at 37° C. DNA was extracted from variant cultures using the Qiagen maxi prep kit.

Humanized antibodies were generated by combining each heavy chain variant of VH.v1, VH.1, VH.2, VH.3 or VH.4 with each light chain variant of VL.v1, VL.1, VL.2, VL.3, VL.4, VL.5, and VL.6 for a total of 35 variants (Table 17, below).

Among them, 11 variants with minimum back mutation were selected for antibody production and purification, and were evaluated for their ErbB2 binding EC50 by capture ELISA. The results (See Table 18, below) indicate that 11 variants except one exhibit equivalent ErbB2 binding EC50 as compared with 5F12 chimeric antibody.

Example 9. Humanization of Anti-ErbB2 Mouse Monoclonal Antibody 5G9

5G9 mouse anti-ErbB2 antibody (Table 12, above) was humanized. Humanized variant amino acid sequences VH.v1, VH.1, VH.2, VH.3, VH.4, VL.v1, VL.1, VL.2, VL.3, VL.4, VL.5, VL.6 (Table 19, below) were converted to DNA sequence based on the most homologous human germlines and synthesized. For the heavy chain variants, human germline heavy chain acceptor sequences hIGHV1-69 FR1, hIGHV1-69 FR2, hIGHV1-69 FR3, and hIGHJ1 FR4 were used (see, Table 2, above). For light chain variant VL.v1, VL.1, VL.2, VL.3, VL.4, VL.5, VL.6, human germline light chain acceptor sequences hIGKV1-27 FR1, hIGKV1-27 FR2, hIGKV1-27 FR3, and hIGHJ1 FR4 were used (see, Table 3, above). Individual constructs were sequence verified to check for accuracy. Positive variants were then inoculated into 250 ml Luria broth plus ampicillin and cultured overnight at 37° C. DNA was extracted from variant cultures using the Qiagen maxi prep kit.

Humanized antibodies were generated by combining each heavy chain variant of VH.v1, VH.1, VH.2, VH.3, VH.4 and VH5 with each light chain variant of VL.v1, VL.1, VL.2, VL.3, VL.4, VL.5, and VL.6 for a total of 42 variants (Table 20, below).

Among them, 12 variants with minimum back mutation were selected for antibody production and purification, and were evaluated for their ErbB2 binding EC50 by capture ELISA. The results (See Table 21, below) indicate that 6/12 variants exhibit lower ErbB2 binding EC50 as compared with 5G9 chimeric antibody.

Example 10. In Vivo Efficacy of Anti-ErbB2 Antibody Mixtures in BT474 Xenograft Model The in vivo study of BT474 breast cancer xenograft tumor model commercially conducted by Crown Bioscience under the contract number E0627-T1401. The present study examined the antitumor activity of: (a) the treatment with Trastuzumab alone; (b) the combination of Trastuzumab and any one of antibodies isolated by the present invention; (c) the combination of Trastuzumab and Pertuzumab.

Female NOD/SCID mice, age 6-8 Weeks; body Weight 17.7-26.0 g (Beijing HFK Bioscience Co., Ltd. China) are maintained under specific-pathogen-free condition with daily cycles of 12-hour light/12-hour darkness, room temperature 21.9-23.8° C., humidity 40~45%. After arrival, animals are housed in the quarantine part of the animal facility for one week to get accustomed to new environment and for observation. Continuous health monitoring is carried out on regular basis. Diet food (irradiated by radioactive isotope $^{60}$Co) and water are provided ad libitum.

The human breast cancer cell line BT474 were cultured in DMEM with 10% FBS. Upon cell growth reaching log phase stage, cells were collected and washed with PBS and subsequently diluted into appropriate concentration. After mixing with reconstituted basement membrane (Matrigel; Collaborative Research, Bedford, Mass.) with 1:1 volume ratio, the cells ($1 \times 10^7$ cells/mouse) were inoculated at under mouse mammary pad. When the volume of implanted tumor reach to about 151 mm$^3$, mice were randomly divided into 8 groups (6 mice/group) including: (a) Group-1: PBS (vehicle control); (b) Group-2: PC (Trastuzumab only, 3 mg/kg); (c) Group-3: a combination of Trastuzumab+4C9 (1.5 mg/kg+1.5 mg/kg); (d) Group-4: a combination of Trastuzumab+4H2 (1.5 mg/kg+1.5 mg/kg); (e) Group-5: a combination of Trastuzumab+4G6 (1.5 mg/kg+1.5 mg/kg); (f) Group-6: a combination of Trastuzumab+5F12 (1.5 mg/kg+1.5 mg/kg); (g) Group-7: a combination of Trastuzumab+5G9 (1.5 mg/kg+1.5 mg/kg); (h) Group-8: a combination of Trastuzumab+Pertuzumab (1.5 mg/kg+1.5 mg/kg). The mice were treated weekly for first two week followed by twice weekly for the following two weeks with a total 7 dosages. The testing antibodies were administrated by tail vein injection.

Figure 3:
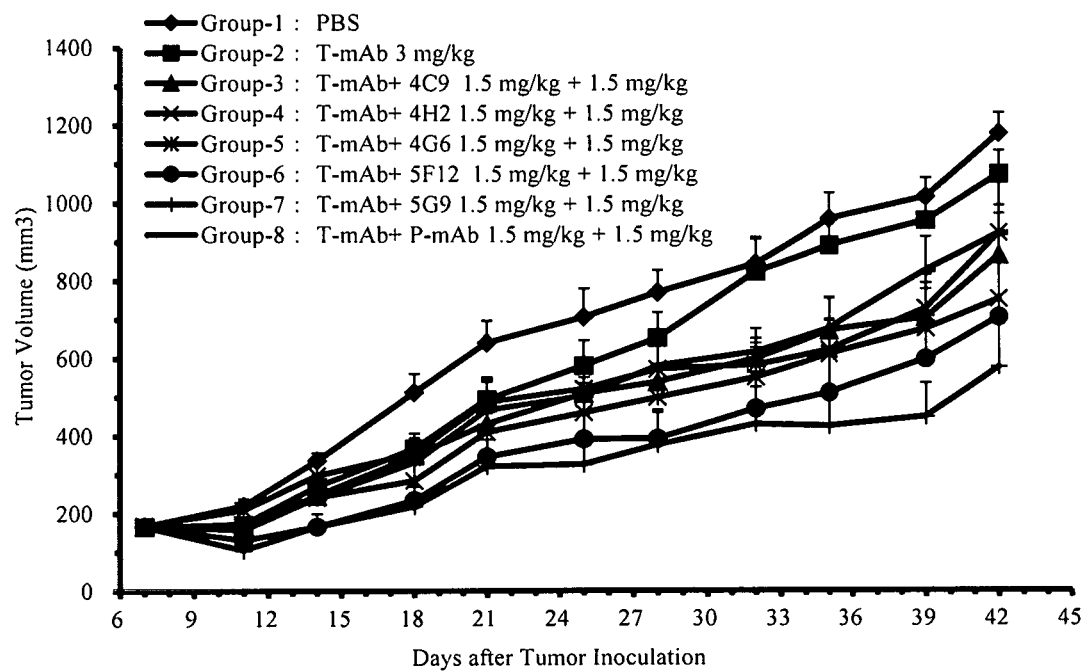
FIGS. 3A-3B depict response of the treatment of PBS (♦), Trastuzumab only (■), Trastuzumab/4C9 (▲), Trastuzumab/4H2 (x), Trastuzumab/4G (✱), Trastuzumab/5F12 (●), and Trastuzumab/5G9 (₁) and Trastuzumab/Pertuzumab (−) treatment in BT474 breast cancer xenograft model. Note: T-mAb represents Trastuzumab, P-mAb represents Pertuzumab.
Figure 3:
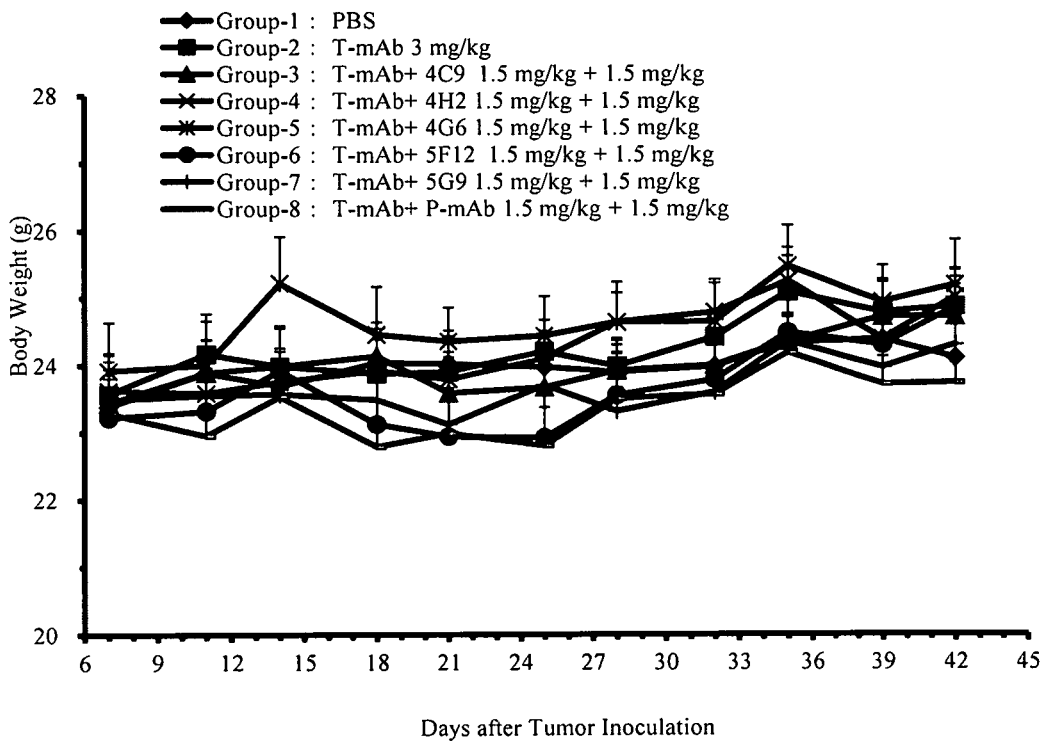

In this study, the mean tumor size of the vehicle treated mice reached 1064 mm$^3$ on day 32 post treatment initiation. PC group treatment (Trastuzumab alone, 3 mg/kg) exhibited residual anti-tumor activity, resulted in mean tumor size of 965 mm$^3$ on day 32 with a T/C value of 95%, smaller than whereas no significant difference was observed compare to the vehicle control (P=0.24) in terms of tumor volume, indicating that Trastuzumab has little anti-tumor activity at low dosage of 3 mg/kg. Conversely, under the same dosage schedule, the combinations of Trastuzumab with either one of antibodies isolated by this invention or with Pertuzumab show moderate to significantly strong anti-tumor activity compared with vehicle control. Preferably, under the same dosage treatment, the combination of Trastuzumab+5F12 or Trastuzumab+5G9 greatly inhibit tumor growth with T/C value of 47% or 53% (p<0.03 or p<0.001, respectively), demonstrating that 5F12 or 5G9 is able to significantly enhance the anti-tumor efficacy of Trastuzumab treatment. More preferably, 5F12 and 5G9 demonstrated significantly higher synergistic activity toward Trastuzumab-mediated anti-tumor efficacy than Pertuzumab, a known drug currently used in clinics (p<0.07 and p<0.006, respectively). The results of the anti-tumor efficacy of the combinations of Trastuzumab plus antibodies isolated by this invention were shown in FIGS. 3A-3B and Table 22.

Example 11. In Vivo Efficacy of Anti-ErbB2 Antibody Mixtures in NCI-N87 Gastric Model (5G9, 5F12)

NCI-N87 xenograft model was used to further evaluate the synergistic efficacy of antibodies of the present invention combined with Trastuzumab. The procedure for this study is briefly summarized as following: <1> NCI-N87 cell was cultured into log phase and collected; <2> Re-suspend NCI-N87 cells in PBS, adjust cell density to $8 \times 10^7$ cells/ml, and subcutaneously inject 100 μl or $8 \times 10^7$ cells in the left flank area of athymic nude female mice; <3> Allow tumors to grow to approximately 100~200 mm³ in size before mice were randomized into groups; <4> Animals received intraperitoneal administration of antibodies at the indicated doses twice weekly, and tumor size as well as body weight were measured twice a week. Tumor volumes (TV) were calculated using the formula $TV=\frac{1}{2} \times a \times b^2$, where "a" represents the larger tumor diameter and "b2" represents the smallest tumor diameter.

The study design of the in vivo efficacy of the combination of Trastuzumab with 5G9, 5F12 or pertuzumab on NCI-N87 tumor growth is shown in Table 23. The stage-one of this study is aimed to evaluate the efficacy of 5G9, 5E12, and their combination with Trastuzumab at different dosages (5 mg/kg, 10 mg/kg, and 15 mg/kg). The stage-2 of this study is specifically focusing on two aspects: <1> Start from day-26, whether the addition of Trastuzumab (5 mg/kg) to the single treatment of 5G9 and 5F12 at low dosage (5 mg/kg) is able to reconstitute synergistic efficacy, as compare to Trastuzumab high dosage group (15 mg/kg). <2> Start from day-26, under the same dosage (5 mg/kg+5 mg/kg) without further treatment, whether the combination of Trastuzumab with 5G9 or 5E12 is able to maintain its anti-tumor efficacy in comparing with that of Trastuzumab and Pertuzumab.

The stage-one results of this study are summarized in Table 24. The study conclusions are summarized as following: <1> Trastuzumab treatment at 5 mg/kg dosage exhibited strong anti-tumor activity, resulted in mean tumor size of 227 mm³ on day 22 with a TGI value (i.e., TGI=(1−mean volume of treated tumors/mean volume of control tumors)× 100%) of 43.59%, statistically significant difference was observed when comparing to the vehicle control in terms of tumor volume (Group 2 versus Group 1, P<0.01). However, the three-times increase of Trastuzumab treatment (15 mg/kg) is not able to significantly enhance its efficacy (Group 3 versus Group 2, P>0.05), demonstrating that the anti-tumor efficacy of Trastuzumab will not be improved after reaching a certain dosage such as 5 mg/kg; <2> However the combination of Trastuzumab with either 5G9 or 5F12 at lower dosage (5 mg/kg+5 mg/kg) shows much higher anti-tumor efficacy than the single treatment of 5G9, 5F12 or Trastuzumab at high dosage (15 mg/kg). Greatly significant difference was observed between the combination treatments (group 8, 10) and the single treatment (group 5, 7 and 3) on day 22 in terms of tumor volume (group 8 or 10 versus group 5, 7 or 3, P<0.01), providing the evidence that the combination of Trastuzumab with 5G9 or 5F12 exhibits strong synergistic anti-tumor efficacy; <3> Under the same dosage treatment (5 mg/kg+5 mg/kg or 15 mg/kg+ 15 mg/kg), the combination of Trastuzumab and 5G9 shows much higher anti-tumor activity than that of Trastuzumab and Pertuzumab, resulted in mean tumor size of 8.75 mm³ or 7.23 mm³ on day 22 with a TGI value of 98.31% or 98.61%. Greatly significant difference was observed when comparing to the combination of Trastuzumab and Pertuzumab control group (46.83 mm³ or 21.41 mm³ on day 22 with a TGI value of 90.97% or 95.87%, P<0.05 or P<0.01). These results show that, different from Pertuzumab, 5G9 has unique synergistic activity when combining with Trastuzumab; <3> Under the same dosage treatment (15+15 mg/kg), the combination of Trastuzumab and 5G12 shows greatly higher anti-tumor activity than that of Trastuzumab and Pertuzumab, resulted in mean tumor size of 1.45 mm³ on day 22 with a TGI value of 99.72%. Greatly significant difference was observed when comparing to the combination of Trastuzumab and Pertuzumab control group (21.41 mm³ on day 22 with a TGI value of 95.87%, P<0.01). This result demonstrates that, different from Pertuzumab, 5F12 has unique synergistic activity when combining with Trastuzumab.

To investigate whether the addition of Trastuzumab to the existing single treatment of 5G9 or 5F12 would reconstitute synergistic efficacy, the single treatment of 5G9 (5 mg/kg) or 5F12 (5 mg/kg) was further combined with 5 mg/kg of Trastuzumab dosage after stage-one study through the end of stage-two. Shown in Table 25, although the single treatment of 5G9 or 5F12 at 5 mg/kg dosage exhibited significantly lower anti-tumor activity than that of Trastuzumab at 15 mg/kg dosage with the mean tumor size of 424.57 mm³ or 386.92 mm³ on day-26 and TGI value of 54.23% or 25.41% respectively, whereas Trastuzumab treatment at 15 mg/kg dosage with the mean tumor size of 190.75 mm³ on day-26 and a TGI value of 63.23%, (Group 4 or 6 versus Group 3, P=0.003<0.01 or P=0.012<0.05). However, upon addition of Trastuzumab to the single treatment of 5G9 or 5F12 at even 5 mg/kg+5 mg/kg dosage beginning at Day-26, the combination treatment is able to re-constitute synergistic anti-tumor efficacy for catching up the efficacy of Trastuzumab high-dose alone treatment, resulting in the end mean tumor size of 1305.11 mm³ or 879.9 mm³ on day-57 with a TGI value of 39.11% or 58.95%, no statistically significant difference from that of Trastuzumab treatment at 15 mg/kg dosage with the mean tumor size of 888.57 mm³ on day-57 with a TGI value of 58.55%, (Group 4 or 6 versus Group 3, P=0.165>0.05 or P=0.491>0.05, respectively). Similarly, tumor volume progression rate of the combination treatment of 5G9+Trastuzumab or 5F12+Trastuzumab at 5 mg/kg+5 mg/kg dosage is much lower than that of Trastuzumab-treatment at high dosage of 15 mg/kg, resulting in 192.60% or 130.97% for 5G9/Trastuzumab combination or 5F12/Trastuzumab combination versus 292.92% for Trastuzumab only treatment, meanwhile, progression rate of TGI of the combination treatment of 5G9+Trastuzumab or 5F12+ Trastuzumab at 5 mg/kg+5 mg/kg dosage is much higher than that of Trastuzumab-treatment at high dosage of 15 mg/kg, resulting in 39.93% or 53.52% for 5G9/Trastuzumab combination or 5F12/Trastuzumab combination versus −7.71 for Trastuzumab only treatment. Taken together, the results indicate the combination of 5G9 or 5F12 with Trastuzumab exhibit strong synergistic anti-tumor efficacy.

To investigate whether the combination of Trastuzumab with 5G9 or 5E12 is able to maintain better anti-tumor efficacy than Trastuzumab/Pertuzumab combination, lower dosage (5 mg/kg+5 mg/kg) treatment was used for this evaluation since the high dosage treatment of all three combinations (Trastuzumab/5G9, Trastuzumab/5F12, and Trastuzumab/Pertuzumab) resulted in almost complete removal of tumor by day 22. Shown in Table 26, after stopping treatment, the tumor progression in either Trastuzumab/5G9 group or Trastuzumab/5F12 group is quite slow, the tumor progression rate is 93.55% or 125.81% for Trastuzumab/5G9 group or Trastuzumab/5F12 group, respectively, but 351.85% for Trastuzumab/Pertuzumab group. In terms of tumor volume on day 26 versus day 57, no statistically significant difference for either Trastuzumab/5G9 group (P=0.278>0.05) or Trastuzumab/5F12 group (P=0.064>0.05) were observed. In contrast, statistically significant difference was observed for Trastuzumab/Pertuzumab treatment group (P=0.03<0.05) in terms of tumor volume on day 26 versus day 57. In addition, TGI of either Trastuzumab/5G9 group or Trastuzumab/5F12 group highly maintained between day 26 and day 57, but slightly reduction in Trastuzumab/Pertuzumab group. Taken together, these results indicate the combination treatment of Trastuzumab/5G9 or Trastuzumab/5F12 has significantly better efficacy than Trastuzumab/Pertuzumab group.

Example 12. Cell-Based Internalization Rate of Antibodies of this Invention and their Combinations To exam the synergic effects of two-antibody combination on their internalization rate, cell-based endocytosis assay has been performed. The brief procedure is as following: <1> SKBR3 cells were washed with PBS, then digested with Trypsin at 37° C. for ~2 min. The cells were re-suspended in cold FACS buffer, and adjusted to $3 \times 10^6$ cell/ml; <2> 1 ml cell suspension was added to FACS tube, in which a final concentration of 2 ug/ml FITC-conjugated or APC-conjugated antibody (Trastuzumab, or Pertuzumab, or antibodies of this invention), or their combinations were added. The cells were incubated on ice for one hour. Then the cells were centrifuged at 1000 rpm, 5 min, 4° C.; and the supernatant was decanted. The cells were then washed twice with FACS buffer, and re-suspended in 1 ml FACS buffer. 2×200 ul of cell suspension were taken as control and sample at 0 min, respectively. The rest of cells were centrifuged at 1000 rpm, 4° C. for 5 min, to remove supernatant; <3> The cells were re-suspended in medium (DMEM+10% FBS+PS), and incubated at 37° C. for internalization. Then, 200 ul of samples were taken at 30 min and 2 hours respectively. The samples were cooled on ice for 5 min, and centrifuged at 1000 rpm, 4° C. for 5 min to remove supernatant, then washed once with FACS buffer; <4> 250 ul strip buffer was added to the cells, and incubated at RT for 7 min. Then the cells were centrifuged at 1000 rpm, 4° C. for 5 min to remove supernatant, and washed twice with FACS buffer; <5> 200 ul fixing buffer was added to the cells, and incubated at 4° C. for at least 30 min. The cells were then analyzed by flow cytometer; <6> For the control and sample at 0 min taken at step 2, one was directly fixed with fixing buffer (step 5), another was treated with step 4 and step 5 (using strip buffer and fixing buffer); <7> The internalization rate of antibody or antibody combination was calculated as: average percentage change=[internalization group (MFI−MFI blank)]/[binding affinity group (MFI−MFI blank)].

Shown in Table 27, all testing antibodies (Trastuzumab, Pertuzumab, 4C9, 4H2, 4G6, 5F12, and 5G9) show the antigen-antibody internalization phenomenon in SKBR3 cells. Different from Trastuzumab and Pertuzumab, each individual antibody of the present invention (4C9, 4H2, 4G6, 5F12, and 5G9) shows much higher internalization rate than Trastuzumab or Pertuzumab. Among them, 4C9 and 5F12 exhibit greatly significant higher internalization rate than Trastuzumab (P<0.05), supporting antibodies of this invention (especially 4C9, 5F12 and 5G9) are capable to be better candidates for antibody-drug conjugate application.

Shown in Table 28, when combined with antibodies of the present invention, the internalization rate of Trastuzumab is greatly significantly higher than Trastuzumab alone (P<0.01), demonstrating antibodies of the present invention are capable to significantly enhance the internalization rate of Trastuzumab and consequently may be capable to improve the efficacy of the treatment of Trastuzumab-drug conjugate (i.e., T-DM1).

Example 13. In Vivo Efficacy of Anti-ErbB2 Antibody Combination in PDX HERCEPTIN-Resistant Gastric Model—HUPRIME® Gastric Cancer Xenograft Model As an established and validated PDX model in Crown Bioscience (Beijing) Inc., HUPRIME® gastric cancer xenograft model GA0060 derived from a 69-year-old female Asian patient is selected for this efficacy study. In vivo efficacy study of anti-ErbB2 antibody combination in the treatment of HUPRIME® gastric cancer xenograft model GA0060 in Balb/c nude mice was performed by Crown Bioscience Inc. (Beijing) under the contract number E0627-T1501/T1502. Briefly, tumor fragments from stock mice inoculated with selected primary human gastric cancer tissues were harvested and used for inoculation into BALB/c nude mice. Each mouse was inoculated subcutaneously at the right flank with primary human gastric cancer model GA0060 fragment (P7, 2-4 mm in diameter) for tumor development. The treatment was started when the average tumor size reached about 200 $mm^3$. Mice were allocated randomly into 12 experimental groups according to their tumor sizes, 6 mice per group. The day was denoted as day 0. The test articles were administrated to the tumor-bearing mice from day 0 through day 28 according to predetermined regimen shown in the following Table 29.

Figure 4:
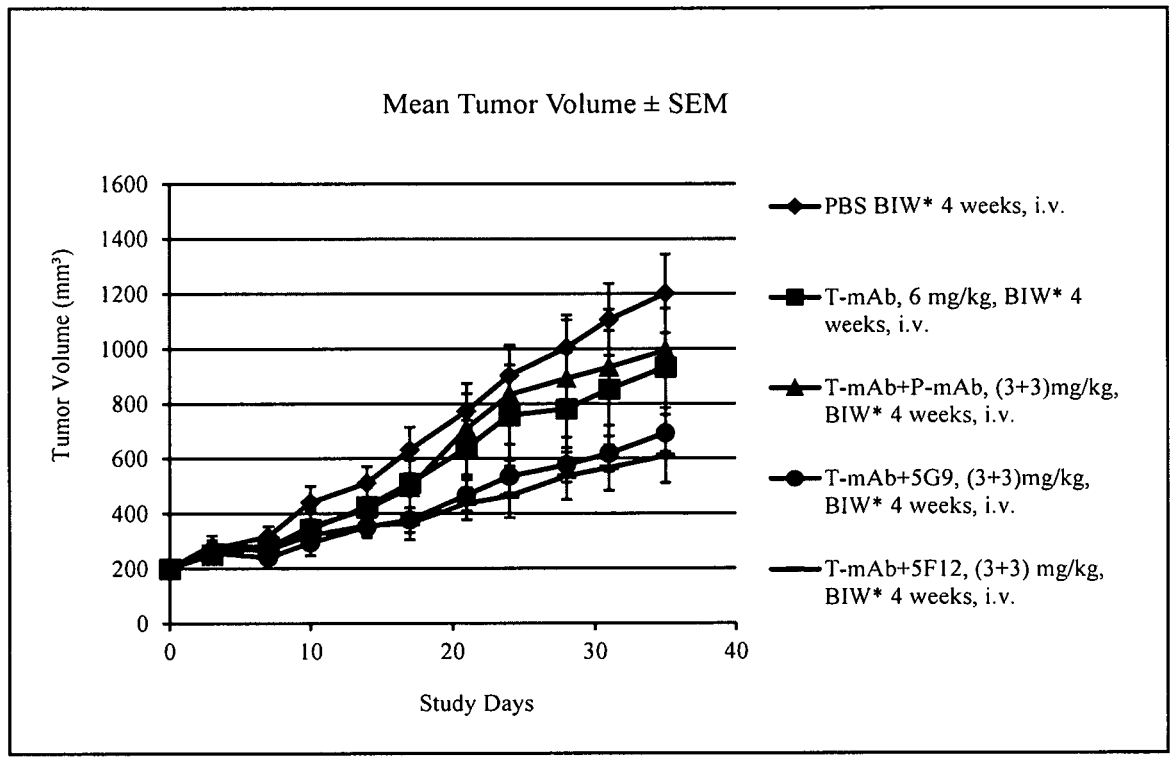
FIGS. 4A-4B depict response of the treatment of PBS (♦), Trastuzumab only (■), Trastuzumab+Pertuzumab (▲), Trastuzumab+5F12 (●), and Trastuzumab+5G9 (₁) and Trastuzumab/Pertuzumab (−) treatment in PDX Trastuzumab-resistant Gastric Model. Note: T-mAb represents Trastuzumab, P-mAb represents Pertuzumab.
Figure 4:
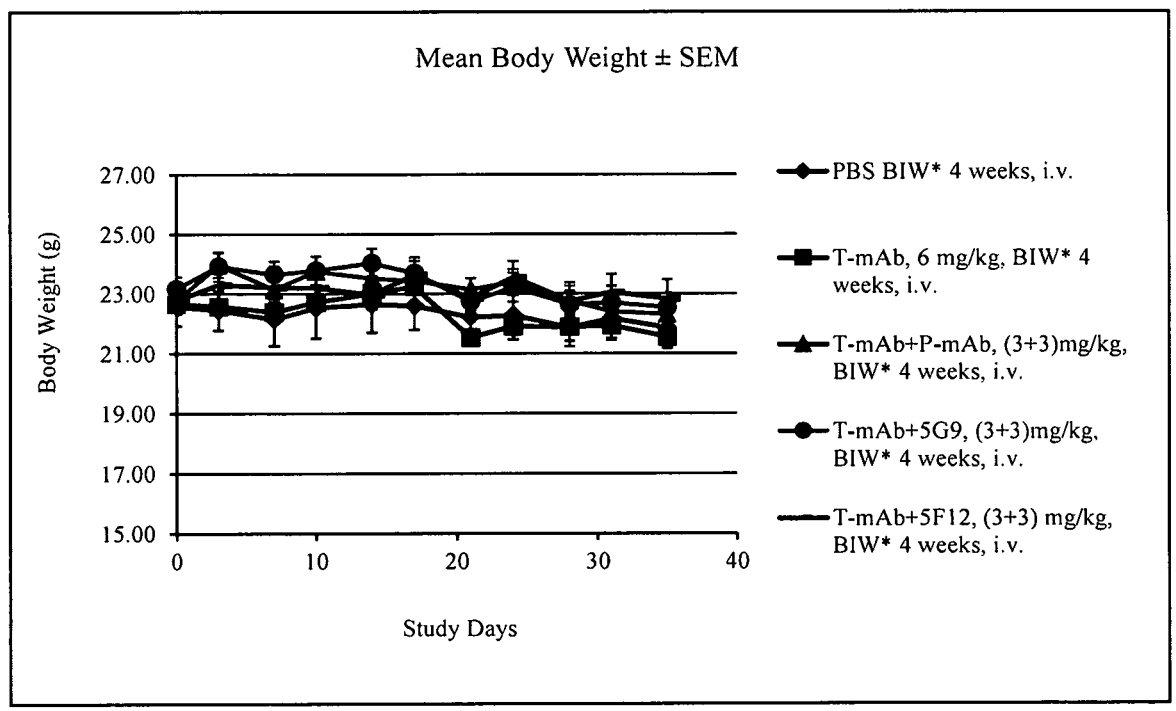

The result of this study is summarized in Table 30 and FIGS. 4A-4B. The mean tumor size of the vehicle treated mice reached 1201.1 $mm^3$ on day 35 post treatment initiation. Under the same test: <1> Trastuzumab only treatment exhibited minor anti-tumor activity, resulted in mean tumor size of 932.7 $mm^3$ on day 35 with a T/C value of 77.7%, no significant difference was observed compare to the vehicle control (P=0.161>0.05) in terms of tumor volume; <2> The combination of Trastuzumab and Pertuzumab treatment exhibited even less anti-tumor efficacy as compared to Trastuzumab-only treatment, resulted in mean tumor size of 994.6 $mm^3$ on day 35 with a T/C value of 82.8%, no significant difference was observed compare to the vehicle control (P=0.217>0.05); <3> The combination of Trastuzumab and 5F12 treatment showed more potent efficacy than Trastuzumab-only treatment, resulted in mean tumor size of 691.6 $mm^3$ on day 35 with a T/C value of 57.6%, greatly significant difference was observed compare to the vehicle control (P=0.004<0.01) in terms of tumor volume; <4> The combination of Trastuzumab and 5G9 treatment exhibited more potent efficacy than Trastuzumab-only treatment, resulted in mean tumor size of 608.8 $mm^3$ on day 35 with a T/C value of 50.7%, greatly significant difference was observed compare to the vehicle control (P=0.004<0.01) in terms of tumor volume.

All documents, books, manuals, papers, patents, published patent applications, guides, abstracts, and/or other references cited herein are incorporated by reference in their entirety. Other embodiments of the present invention will be apparent to those skilled in the art from consideration of the specification and practice of the present invention disclosed herein. It is intended that the specification and examples be considered as exemplary only, with the true scope and spirit of the present invention being indicated by the following claims.

TABLE 1

Sequences of human IgG heavy chain and light chain constant domain

| SEQ ID | Sequence Identifier Protein | Sequence<br>123456789012345678901234567890123456789012345678 90 |
|---|---|---|
| 1 | Ig gamma-1 constant region | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTC LVKGFYPSDIAVEWESNGQPENNYKTTPPVLDSDGSFFLYSKLTVDKSRW |
| 2 | Ig gamma-1 constant region | RTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTK SFNRGEC |

TABLE 2

Heavy Chain Acceptor Sequences

| SEQ ID | Protein region/ Closest Germline Family | Amino Acid Sequence<br>123456789012345678901234567890 |
|---|---|---|
| 3 | hIGHV1-46 FR1 | QVQLVQSGAEVKKPGASVKVSCKASGYTFT |
| 4 | hIGHV1-46 FR2 | WVRQAPGQGLEWMG |
| 5 | hIGHV1-46 FR3 | RVTMTRDTSTSTVYMELSSLRSEDTAVYYCAR |
| 6 | hIGHJ4 FR4 | WGQGTLVTVSS |
| 161 | hIGHV1-69 FR1 | QVQLVQSGAEVKKPGSSVKVSCKASGGTFS |
| 162 | hIGHV1-69 FR2 | WVRQAPGQGLEWMG |
| 163 | hIGHV1-69 FR3 | RVTITADESTSTAYMELSSLRSEDTAVYYCAR |

TABLE 3

Light Chain Acceptor Sequences

| SEQ ID | Protein region/ Closest Germline Family | Amino Acid Sequence<br>123456789012345678901234567890 |
|---|---|---|
| 7 | hIGKV1-33 FR1 | DIQMTQSPSSLSASVGDRVTITC |
| 8 | hIGKV1-33 FR2 | WYQQKPGKGPKLLIY |
| 9 | hIGKV1-33 FR3 | GVPSRFSGSGSGTDFTLTISSLQPEDFATYYC |
| 10 | hIGKJ1 FR4 | FGQGTKVEIK |
| 164 | hIGKV1-27 FR1 | DIQMTQSPSSLSASVGDRVTITC |
| 165 | hIGKV1-27 FR2 | WYQQKPGKGPKLLIY |
| 166 | hIGKV1-27 FR3 | GVPSRFSGSGSGTDFTLTISSLQPEDFATYYC |

TABLE 4

Anti-ErbB2 hybridoma screening (Indirect ELISA)—an example (in Example 1)

| P61 | 1 | 2 | 3 | 4 | 5 | 6 | 7 | 8 | 9 | 10 | 11 | 12 |
|---|---|---|---|---|---|---|---|---|---|---|---|---|
| A | 0.09 | 0.11 | 0.12 | 0.10 | 0.18 | 0.10 | 0.11 | 0.09 | 0.10 | 0.10 | 0.11 | 0.09 |
| B | 0.09 | 0.11 | 0.11 | 0.09 | 0.11 | 0.11 | 0.13 | _2.88_ | 0.10 | 0.12 | 0.08 | 0.08 |
| C | 0.09 | 0.08 | 0.10 | 0.10 | _2.43_ | 0.10 | 0.12 | 0.10 | _1.90_ | 0.09 | 0.12 | 0.10 |

TABLE 4-continued

Anti-ErbB2 hybridoma screening (Indirect ELISA)—an example (in Example 1)

| P61 | 1 | 2 | 3 | 4 | 5 | 6 | 7 | 8 | 9 | 10 | 11 | 12 |
|---|---|---|---|---|---|---|---|---|---|---|---|---|
| D | 0.10 | 0.08 | 0.10 | 0.83 | 0.12 | 1.25 | 0.12 | 0.10 | 0.19 | 0.10 | 0.12 | 0.15 |
| E | 0.10 | 0.13 | 1.07 | *2.82* | 0.11 | 0.10 | 0.09 | 0.10 | 0.12 | 0.11 | *2.73* | 0.12 |
| F | 0.12 | *1.55* | *1.98* | 0.13 | 0.11 | 0.10 | *2.49* | 0.95 | *2.48* | 0.12 | *2.71* | *1.46* |
| G | 0.80 | *2.40* | 0.13 | 0.13 | *2.03* | *2.34* | 0.10 | 0.11 | 0.15 | 0.14 | 0.14 | 0.13 |
| H | 0.14 | 0.13 | 0.13 | 0.12 | 0.26 | 0.18 | 0.14 | 0.15 | 0.12 | 0.16 | 0.11 | 2.60 |

Note:
H11: Negative control-PBS, H12: positive control (polyclonal serum)

TABLE 5

Cell-based binding screening for hybridoma supernatant—an example

| PLT 3 | 1 | 2 | 3 | 4 | 5 | 6 | 7 | 8 | 9 | 10 | 11 | 12 |
|---|---|---|---|---|---|---|---|---|---|---|---|---|
| A | 1 | 40 | 1 | 41 | 9 | 9 | 46 | 16 | 4 | 15 | 32 | 19 |
| B | 1 | 40 | 54 | 1 | 71 | 1 | 64 | 3 | 48 | 1 | 38 | 8 |
| C | 5 | 1 | 1 | 41 | 2 | 51 | 20 | 2 | 1 | 8 | 38 | 29 |
| D | 14 | 2 | 46 | 33 | 18 | 41 | 3 | 1 | 49 | 44 | 6 | 6 |
| E | 36 | 41 | 1 | 1 | 1 | 1 | 39 | 59 | 26 | 32 | 41 | 3 |
| F | 1 | 4 | 49 | 2 | 6 | 1 | 45 | 34 | 3 | 1 | 0 | 43 |
| G | 41 | 12 | 5 | 33 | 33 | 60 | 29 | 39 | 34 | 1 | 6 | 4 |
| H | 36 | 8 | 70 | 4 | 12 | 10 | 1 | 1 | 16 | 52 | 1 | 2 |

Note:
H11: normal mouse serum, H12: positive control (fusion serum), The rest wells: hybridoma supernatant. The sample with ratio value larger than 2 is considered as positive clone, the higher of ratio, the higher priority to be selected for further evaluation.

TABLE 6

Epitope grouping of hybridoma supernatant (Trastuzumab-competitive ELISA)

| | 1 | 2 | 3 | 4 | 5 | 6 | 7 |
|---|---|---|---|---|---|---|---|
| A | 2.9 | 2.89 | 2.85 | 2.81 | 2.9 | 2.9 | 2.71 |
| B | 2.82 | 2.67 | 2.87 | 2.82 | 2.85 | 2.95 | 2.79 |
| C | 2.86 | 2.74 | 2.78 | 1.54 | 2.45 | *0.49* | *0.35* |
| D | 2.91 | *0.36* | *0.24* | *0.38* | 1.51 | 1.08 | 1.13 |
| E | 2.81 | 2.78 | 2.78 | 2.81 | 2.7 | 2.63 | 2.85 |
| F | 2.77 | 2.87 | 2.92 | 2.81 | 1.99 | 2.07 | 2.91 |
| G | 2.82 | 2.82 | 2.83 | 2.76 | 2.57 | 2.8 | 2.8 |
| H | *0.83* | *0.8* | *0.86* | *0.74* | *0.76* | *0.73* | 0.13 |

Note:
F7: hIgG 5 ug/ml, G7: mIgG 5 ug/ml, H11: Trastuzumab 5 ug/ml, Other well: hybridoma supernatant

TABLE 7

Monoclonal antibodies isolated by this invention

| Clone ID | Isotype | ELISA HER2 Binding | FACS HER2⁺ Cell Binding |
|---|---|---|---|
| 4C9G3F5 | IgG1, κ | + | + |
| 4H2H2H9 | IgG1, κ | + | + |
| 4G6C9B8 | IgG1, κ | + | + |
| 5F12E5A8 | IgG1, κ | + | + |
| 5G91B42A3 | IgG1, κ | + | + |

TABLE 8

ErbB2-ECD Binding of antibodies of this invention

| | Antibody ID | Capture ELISA (EC$_{50}$ nM) |
|---|---|---|
| Mouse antibody | 4C9 | 0.142 |
| | 4H2 | 0.117 |
| | 4G6 | 0.021 |
| | 5F12 | 0.156 |
| | 5G9 | 0.499 |
| Control antibody | Trastuzumab | 0.013 |
| | Pertuzumab | 0.021 |

TABLE 9

Cross-species binding of antibodies isolated by this invention

| Antibody ID | Human ErbB2-ECD | *Macaca mulatta* ErbB2-ECD | *Macaca fascicularis* ErbB2-ECD | Rat ErbB2-ECD | Mouse ErbB2-ECD |
|---|---|---|---|---|---|
| 4C9 | + | + | + | − | − |
| 4H2 | + | + | + | − | − |
| 4G6 | + | + | + | − | − |
| 5F12 | + | + | + | − | − |
| 5G9 | + | + | + | − | − |
| Trastuzumab | + | + | + | − | − |
| Pertuzumab | + | + | + | − | − |
| PBS | − | − | − | − | − |

Note:
"+" indicates binding activity;
"−" indicate no binding activity

TABLE 10

Epitope grouping of purified antibodies of this invention

| | 4C9-Bio | 4H2-Bio | 4G6-Bio | 5F12-Bio | 5G9-Bio | Trastuzumab-Bio | Pertuzumab-Bio |
|---|---|---|---|---|---|---|---|
| 4C9 | − | − | − | − | − | + | + |
| 4H2 | − | − | − | − | − | + | + |
| 4G6 | − | − | − | − | − | + | + |
| 5F12 | − | − | − | − | − | + | + |
| 5G9 | − | − | − | − | − | + | + |

TABLE 10-continued

Epitope grouping of purified antibodies of this invention

| | 4C9-Bio | 4H2-Bio | 4G6-Bio | 5F12-Bio | 5G9-Bio | Trastuzumab-Bio | Pertuzumab-Bio |
|---|---|---|---|---|---|---|---|
| Trastuzumab | + | + | + | + | + | − | + |
| Pertuzumab | + | + | + | + | + | + | − |
| PBS | + | + | + | + | + | + | + |

Note:
"−" indicate competitive relationship due to binding the "same" epitope: "+" indicates non-competitive relationship due to binding the different epitopes.

TABLE 11

The efficacy of cell proliferation inhibition of antibodies of this invention

| | BT474 cell proliferation inhibition activity | |
|---|---|---|
| Treatment group | IC$_{50}$ (nM) | Max inhibition (%) |
| Trastuzumab + 4C9 | 0.879 | 80.91 |
| Trastuzumab + 4H2 | 0.631 | 89.81 |
| Trastuzumab + 4G6 | 0.801 | 94.36 |
| Trastuzumab + 5F12 | 0.635 | 92.32 |
| Trastuzumab + 5G9 | 0.5156 | 95.17 |
| Trastuzumab + Pertuzumab* | 1.067~1.236 | 65.29~68.67 |
| Trastuzumab + mIgG | 1.217 | 73.69 |
| higG + 4C9 | 0.471 | 27.34 |
| higG + 4H2 | ~1.165 | 44.77 |
| higG + 4G6 | ~1.236 | 38.46 |
| higG + 5F12 | 0.700 | 43.97 |
| higG + 5G9 | ~1.334 | 13.34 |
| higG + Pertuzumab* | 1.368~2.083 | 17.08~22.30 |
| higG + Trastuzumab* | 1.237~1.662 | 70.74~71.05 |

Note:
*indicates the range of at least two experiments

TABLE 12

VH and VL Amino Acid Sequences of Mouse Anti-ErbB2 Monoclonal Antibodies of This Invention

| SEQ ID NO | Protein name | Residue region | Sequence |
|---|---|---|---|
| 17 | VH 4C9 | | QVQLQQSGAELARPGASVKMSCKASGYTFTSYTMHWVKQRPGQGLDWIGYINPSSGYTTYNQKFKDKATLTADKSSSTAYMQLSSLASADSAVYYCARASAYSLDYWGQGTTLVTVSS |
| 56 | VH 4C9 CDR-H1 | residues 31-35 of SEQ ID NO: 17 | SYTMH |
| 57 | VH 4C9 CDR-H2 | residues 50-66 of SEQ ID NO: 17 | YINPSSGYTTYNQKFKD |
| 58 | CH 4C9 CDR-H3 | residues 99-106 of SEQ ID NO: 17 | ASAYSLDY |
| 18 | VL 4C9 | | DIQMTQSPSSLSASLGGRVTITCKASHDIDRYIAWYQHKPGKGPRLLIHYTSTLQPGIPSRFSGSGSGRDYSFSISNLEPEDIATYYCLKYDNLLWTFGGGTKLEIT |
| 59 | VL 4C9 CDR-L1 | residues 24-34 of SEQ ID NO: 18 | KASHDIDRYIA |
| 60 | VL 4C9 CDR-L2 | residues 50-56 of SEQ ID NO: 18 | YTSTLQP |
| 61 | VL 4C9 CDR-L3 | residues 89-97 of SEQ ID NO: 18 | LKYDNLLWT |
| 19 | VH 4H2 | | QVQLQQSGAELARPGASVKMSCKASGFTFTSYTIHWVKQRPGQGLDWIGYINPSSGYTTYNQRFKDKATLTADKSSSTAYMQLSSLTSADSAVYYCARASAYSLDYWGQGTTLVTVSS |
| 62 | VH 4H2 CDR-H1 | residues 31-35 of SEQ ID NO: 19 | SYTIH |
| 63 | VH 4H2 CDR-H2 | residues 50-66 of SEQ ID NO: 19 | YINPSSGYTTYNQRFKD |
| 64 | VH 4H2 CDR-H3 | residues 99-106 of SEQ ID NO: 19 | ASAYSLDY |
| 20 | VL 4H2 | | DIQMTQSPSSLSASLGGKVTITCKASQDIDRYIAWYQHKPGKGPRLLIHYTSTLQPGIPSRFSGSGSGRNYSFSISNLEPEDIATYYCLKYDNLLWTFGGGTKLEIK |
| 65 | VL 4H2 CDR-L1 | residues 24-34 of SEQ ID NO: 20 | KASQDIDRYIA |
| 66 | VL 4H2 CDR-L2 | residues 50-56 of SEQ ID NO: 20 | YTSTLQP |

TABLE 12-continued

VH and VL Amino Acid Sequences of Mouse Anti-ErbB2
Monoclonal Antibodies of This Invention

| SEQ ID NO | Protein name | Residue region | Sequence 1234567890123456789012345678901234567890 |
|---|---|---|---|
| 67 | VL 4H2 CDR-L3 | residues 89-97 of SEQ ID NO: 20 | LKYDNLLWT |
| 21 | VH 4G6 | | QVQLQQSGAELARPGASVKMSCKASGYTFTSYTMHWVKQR PGQGLEWIGYINPSSAYTNYNQKFKDKATLTADKSSSTAN MQLNSLTSEDSAVYYCARASAYSLDYWGQGTALTVSS |
| 68 | VH 4G6 CDR-H1 | residues 31-35 of SEQ ID NO: 21 | SYTMH |
| 69 | VH 4G6 CDR-H2 | residues 50-66 of SEQ ID NO: 21 | YINPSSAYTNYNQKFKD |
| 70 | VH 4G6 CDR-H3 | residues 99-106 of SEQ ID NO: 21 | ASAYSLDY |
| 22 | VL 4G6 | | DIQMTQSPSSLSASLGGKVTITCKASQDINKYLAWYQHKP GKGPRLLIHSTSTLYPGIPSRFSGSGSGRDYSFRITNLEP EDIATYYCLQYDNLLWTFGGGTKVGIR |
| 71 | VL 4G6 CDR-L1 | residues 24-34 of SEQ ID NO: 22 | KASQDINKYIA |
| 72 | VL 4G6 CDR-L2 | residues 50-56 of SEQ ID NO: 22 | STSTLYP |
| 73 | VL 4G6 CDR-L3 | residues 89-97 of SEQ ID NO: 22 | LQYDNLLWT |
| 23 | VH 5F12 | | QVQLQQSGAELARPGASVKMSCKASGYTFTSYTMHWIKQR PGQGLEWIGYINPSSYTNYNQNFKDKATLTADKSSSTAN MQLNSLTSEDSAVYYCARASSYSLDYWGQGTALTVSS |
| 74 | VH 5F12 CDR-H1 | residues 31-35 of SEQ ID NO: 23 | SYTMH |
| 75 | VH 5F12 CDR-H2 | residues 50-66 of SEQ ID NO: 23 | YINPSSYTNYNQKFKD |
| 76 | VH 5F12 CDR-H3 | residues 99-106 of SEQ ID NO: 23 | ASSYSLDY |
| 24 | VL 4F12 | | DIQMTQSPSSLSTSLGGKVTITCKASQDINKYIAWYQHKP GKGPRLLIHSTSTLYPGIPSRFSGSGSGKDYSFRITNLEP EDIATYYCLQYDNLLWTFGGGTKLGIR |
| 77 | VL 5F12 CDR-L1 | residues 24-34 of SEQ ID NO: 24 | KASQDINKYIA |
| 78 | VL 5F12 CDR-L2 | residues 50-56 of SEQ ID NO: 24 | STSTLYP |
| 79 | VL 5F12 CDR-L3 | residues 89-97 of SEQ ID NO: 24 | LQYDNLLWT |
| 25 | VH 5G9 | | QVQLQQSGAELARPGASVKMSCKTSGYTFSSYTIHWVKQR PGQGLDWIGYINPSSDYTAYNQKFRDKATLTADQSSNTAY MQLSSLASADSAVYYCARASAFSLDFWGQGTTLTVSS |
| 80 | VH 5G9 CDR-H1 | residues 31-35 of SEQ ID NO: 25 | SYTIH |
| 81 | VH 5G9 CDR-H2 | residues 50-66 of SEQ ID NO: 25 | YINPSSDYTAYNQKFRD |
| 82 | VH 5G9 CDR-H3 | residues 99-016 of SEQ ID NO: 25 | ASAFSLDF |
| 26 | VL 5G9 | | DIQMTQSPSSLSASLGGKVTISCKASHDIDRYIAWYQHKP GKGPRLLIHYTSTLQPGIPSRFSGSGSGRDYSFSISNLEP EDVATYYCLNYDNLLWTFGGGTKLEIT |
| 83 | VL 5G9 CDR-L1 | residues 24-34 of SEQ ID NO: 26 | KASHDIDRYIA |
| 84 | VL 5G9 CDR-L2 | residues 50-56 of SEQ ID NO: 26 | YTSTLQP |
| 85 | VL 5G9 CDR-L3 | residues 89-97 of SEQ ID NO: 26 | LNYDNLLWT |

TABLE 13

Recombinant ErbB2-ECD binding EC50 of chimeric antibodies

| Chimeric Antibody | ELISA EC50 (nM) |
|---|---|
| 4C9 chimera | 0.114 |
| 4H2 chimera | 0.118 |
| 4G6 chimera | 0.020 |
| 5F12 chimera | 0.024 |
| 5G9 chimera | 0.049 |
| Trastuzumab | 0.013 |
| Pertuzumab | 0.021 |

TABLE 14

Cross-species binding of chemic antibodies isolated by this invention

| Antibody ID | Human ErbB2-ECD | *Macaca mulatta* ErbB2-ECD | *Macaca fascicularis* ErbB2-ECD | Rat ErbB2-ECD | Mouse ErbB2-ECD |
|---|---|---|---|---|---|
| 4C9c | + | + | + | − | − |
| 4H2c | + | + | + | − | − |
| 4G6c | + | + | + | − | − |
| 5F12c | + | + | + | − | − |
| 5G9c | + | + | + | − | − |
| Trastuzumab | + | + | + | − | − |
| Pertuzumab | + | + | + | − | − |
| PBS | − | − | − | − | − |

Note:
"+" indicates binding activity;
"−" indicate no binding activity

TABLE 15

The efficacy of BT474 cell proliferation inhibition of chimeric antibodies

| Treatment group | BT474 cell proliferation inhibition activity | |
|---|---|---|
| | $IC_{50}$ (nM) | Max inhibition (%) |
| Trastuzumab + 4C9c* | 2.847 | 82.73 |
| Trastuzumab + 4H2c | 2.493 | 76.64 |
| Trastuzumab + 4G6c | 4.274 | 84.96 |
| Trastuzumab + 5F12c | 4.818 | 93.17 |
| Trastuzumab + 5G9c | 3.249 | 92.7 |
| Trastuzumab + Pertuzumab | 2.511 | 70.27 |
| hIgG + 4C9c | not converged | |
| hIgG + 4H2c | 19.29 | 62.34 |
| hIgG + 4G6c | 36.28 | 59.25 |
| hIgG + 5F12c | not converged | |
| hIgG + 5G9c | 43.41 | 66.94 |
| hIgG + Trastuzumab | 3.377 | 69.21 |
| hIgG + Pertuzumab | 10.99 | 48.79 |

Note:
*"c": indicates chimeric antibody

TABLE 16

VH and VL Amino Acid Sequences of Humanized Versions of Mouse Anti-ERBB2 Monoclonal Antibody 5F12

| SEQ ID NO | Protein region | Residue region | Sequence 123456789012345678901234567890123456789 0 |
|---|---|---|---|
| 27 | 5F12.VH.V1 | | EVQLVQSGAEVKKPGSSVKVSCKASGYTFTSYTMHWIRQA PGQGLEWIGYINPSSSYTNYNQNFKDRATLTADKSTSTAY MELSSLRSEDTAVYYCARASSYSLDYWGQGTLVTVSS |
| 86 | 5F12.VH.V1 CDR-H1 | residues 31-35 of SEQ ID NO: 27 | SYTMH |
| 87 | 5F12.VH.V1 CDR-H2 | residues 50-66 of SEQ ID NO: 27 | YINPSSSYTNYNQNFKD |
| 88 | 5F12.VH.V1 CDR-H3 | residues 99-106 of SEQ ID NO: 27 | ASSYSLDY |
| 28 | 5F12.VH.1 | | EVQLVQSGAEVKKPGSSVKVSCKASGYTFTSYTMHWVRQA PGQGLEWIGYINPSSSYTNYNQNFKDRATLTADKSTSTAY MELSSLRSEDTAVYYCARASSYSLDYWGQGTLVTVSS |
| 89 | 5F12.VH.1 CDR-H1 | residues 31-35 of SEQ ID NO: 28 | SYTMH |
| 90 | 5F12.VH.1 CDR-H2 | residues 50-66 of SEQ ID NO: 28 | YINPSSSYTNYNQNFKD |
| 91 | 5F12.VH.1 CDR-H3 | residues 99-106 of SEQ ID NO: 28 | ASSYSLDY |
| 29 | 5F12.VH.2 | | EVQLVQSGAEVKKPGSSVKVSCKASGYTFTSYTMHWIRQA PGQGLEWMGYINPSSSYTNYNQNFKDRATLTADKSTSTAY MELSSLRSEDTAVYYCARASSYSLDYWGQGTLVTVSS |
| 92 | 5F12.VH.2 CDR-H1 | residues 31-35 of SEQ ID NO: 29 | SYTMH |
| 93 | 5F12.VH.2 CDR-H2 | residues 50-66 of SEQ ID NO: 29 | YINPSSSYTNYNQNFKD |
| 94 | 5F12.VH.2 CDR-H3 | residues 99-106 of SEQ ID NO: 29 | ASSYSLDY |
| 30 | 5F12.VH.3 | | EVQLVQSGAEVKKPGSSVKVSCKASGYTFTSYTMHWIRQA PGQGLEWIGYINPSSSYTNYNQNFKDRVTLTADKSTSTAY MELSSLRSEDTAVYYCARASSYSLDYWGQGTLVTVSS |

TABLE 16-continued

VH and VL Amino Acid Sequences of Humanized Versions
of Mouse Anti-ERBB2 Monoclonal Antibody 5F12

| SEQ ID NO | Protein region | Residue region | Sequence<br>123456789012345678901234567890123456789 0 |
|---|---|---|---|
| 95 | 5F12.VH.3 CDR-H1 | residues 31-35 of SEQ ID NO: 30 | SYTMH |
| 96 | 5F12.VH.3 CDR-H2 | residues 50-66 of SEQ ID NO: 30 | YINPSSSYTNYNQNFKD |
| 97 | 5F12.VH.3 CDR-H3 | residues 99-106 of SEQ ID NO: 30 | ASSYSLDY |
| 31 | 5F12.VH.4 | | EVQLVQSGAEVKKPGSSVKVSCKASGYTFTSYTMHWIRQA<br>PGQGLEWIGYINPSSSYTNYNQNFKDRATITADKSTSTAY<br>MELSSLRSEDTAVYYCARASSYSLDYWGQGTLVTVSS |
| 98 | 5F12.VH.4 CDR-H1 | residues 31-35 of SEQ ID NO: 31 | SYTMH |
| 99 | 5F12.VH.4 CDR-H2 | residues 50-66 of SEQ ID NO: 31 | YINPSSSYTNYNQNFKD |
| 100 | 5F12.VH.4 CDR-H3 | residues 99-106 of SEQ ID NO: 31 | ASSYSLDY |
| 32 | 5F12.VL.V1 | | DIQMTQSPSSLSASVGDRVTITCKASQDINKYIAWYQHKP<br>GKGPKLLIHSTSTLYPGIPSRFSGSGSGKDYTFTISSLQP<br>EDIATYYCLQYDNLLWTFGQGTKVEIK |
| 101 | 5F12.VL.V1 CDR-L1 | residues 24-34 of SEQ ID NO: 32 | KASQDINKYIA |
| 102 | 5F12.VL.V1 CDR-L2 | residues 50-56 of SEQ ID NO: 32 | STSTLYP |
| 103 | 5F12.VL.V1 CDR-L3 | residues 89-97 of SEQ ID NO: 32 | LQYDNLLWT |
| 33 | 5F12.VL.1 | | DIQMTQSPSSLSASVGDRVTITCKASQDINKYIAWYQQKP<br>GKGPKLLIHSTSTLYPGIPSRFSGSGSGKDYTFTISSLQP<br>EDIATYYCLQYDNLLWTFGQGTKVEIK |
| 104 | 5F12.VL.1 CDR-L1 | residues 24-34 of SEQ ID NO: 33 | KASQDINKYIA |
| 104 | 5F12.VL.1 CDR-L2 | residues 50-56 of SEQ ID NO: 33 | STSTLYP |
| 106 | 5F12.VL.1 CDR-L3 | residues 89-97 of SEQ ID NO: 33 | LQYDNLLWT |
| 34 | 5F12.VL.2 | | DIQMTQSPSSLSASVGDRVTITCKASQDINKYIAWYQHKP<br>GKAPKLLIHSTSTLYPGIPSRFSGSGSGKDYTFTISSLQP<br>EDIATYYCLQYDNLLWTFGQGTKVEIK |
| 107 | 5F12.VL.2 CDR-L1 | residues 24-34 of SEQ ID NO: 34 | KASQDINKYIA |
| 108 | 5F12.VL.2 CDR-L2 | residues 50-56 of SEQ ID NO: 34 | STSTLYP |
| 109 | 5F12.VL.2 CDR-L3 | residues 89-97 of SEQ ID NO: 34 | LQYDNLLWT |
| 35 | 5F12.VL.3 | | DIQMTQSPSSLSASVGDRVTITCKASQDINKYIAWYQHKP<br>GKGPKLLIYSTSTLYPGIPSRFSGSGSGKDTYFTISSLQP<br>EDIATYYCLQYDNLLWTFGQGTKVEIK |
| 110 | 5F12.VL.3 CDR-L1 | residues 24-34 of SEQ ID NO: 35 | KASQDINKYIA |
| 111 | 5F12.VL.3 CDR-L2 | residues 50-56 of SEQ ID NO: 35 | STSTLYP |
| 112 | 5F12.VL.3 CDR-L3 | residues 89-97 of SEQ ID NO: 35 | LQYDNLLWT |
| 36 | 5F12.VL.4 | | DIQMTQSPSSLSASVGDRVTITCKASQDINKYIAWYQHKP<br>GKGPKLLIHSTSTLYPGVPSRFSGSGSGKDYTFTISSLQP<br>EDIATYYCLQYDNLLWTFGQGTKVEIK |
| 113 | 5F12.VL.4 CDR-L1 | residues 24-34 of SEQ ID NO: 36 | KASQDINKYIA |
| 114 | 5F12.VL.4 CDR-L2 | residues 50-56 of SEQ ID NO: 36 | STSTLYP |
| 115 | 5F12.VL.4 CDR-L3 | residues 89-97 of SEQ ID NO: 36 | LQYDNLLWT |
| 37 | 5F12.VL.5 | | DIQMTQSPSSLSASVGDRVTITCKASQDINKYIAWYQHKP<br>GKGPKLLIHSTSTLYPGIPSRFSGSGSGTDYTFTISSLQP<br>EDIATYYCLQYDNLLWTFGQGTKVEIK |
| 116 | 5F12.VL.5 CDR-L1 | residues 24-34 of SEQ ID NO: 37 | KASQDINKYIA |
| 117 | 5F12.VL.5 CDR-L2 | residues 50-56 of SEQ ID NO: 37 | STSTLYP |

TABLE 16-continued

VH and VL Amino Acid Sequences of Humanized Versions
of Mouse Anti-ERBB2 Monoclonal Antibody 5F12

| SEQ ID NO | Protein region | Residue region | Sequence 12345678901234567890123456789012345678 90 |
|---|---|---|---|
| 118 | 5F12.VL.5 CDR-L3 | residues 89-97 of SEQ ID NO: 37 | LQYDNLLWT |
| 38 | 5F12.VL.6 | | DIQMTQSPSSLSASVGDRVTITCKASQDINKYIAWYQHKP GKGPKLLIHSTSTLYPGIPSRFSGSGSGKDFTFTISSLQP EDIATYYCLQYDNLLWTFGQGTKVEIK |
| 119 | 5F12.VL.6 CDR-L1 | residues 24-34 of SEQ ID NO: 38 | KASQDINKYIA |
| 120 | 5F12.VL.6 CDR-L2 | residues 50-56 of SEQ ID NO: 38 | STSTLYP |
| 121 | 5F12.VL.6 CDR-L3 | residues 89-97 of SEQ ID NO: 38 | LQYDNLLWT |

TABLE 17

Summary of humanized 5F12 antibodies generated and back mutations

| No | Name | VH/VL Combination | Back Mutations in VH/VL |
|---|---|---|---|
| 1 | 5F12.v1 | VH.v1/VL.v1 | 0/0 |
| 2 | 5F12.v2 | VH.v1/VL.1 | 0/H38Q |
| 3 | 5F12.v3 | VH.v1/VL.2 | 0/G43A |
| 4 | 5F12.v4 | VH.v1/VL.3 | 0/H49Y |
| 5 | 5F12.v5 | VH.v1/VL.4 | 0/I58V |
| 6 | 5F12.v6 | VH.v1/VL.5 | 0/K69T |
| 7 | 5F12.v7 | VH.v1/VL.6 | 0/Y71F |
| 8 | 5F12.v8 | VH.1/VL.v1 | I37V/0 |
| 9 | 5F12.v9 | VH.2/VL.v1 | I48M/0 |
| 10 | 5F12.v10 | VH.3/VL.v1 | A67V/0 |
| 11 | 5F12.v11 | VH.4/VL.v1 | L69I/0 |
| 12 | 5F12.v12 | VH.1/VL.1 | I37V/H38Q |
| 13 | 5F12.v13 | VH.1/VL.2 | I37V/G43A |
| 14 | 5F12.v14 | VH.1/VL.3 | I37V/H49Y |
| 15 | 5F12.v15 | VH.1/VL.4 | I37V/I58V |
| 16 | 5F12.v16 | VH.1/VL.5 | I37V/K69T |
| 17 | 5FJ2.v17 | VH.1/VL.6 | I37V/Y71F |
| 18 | 5F12.v18 | VH.2/VL.1 | I48M/H38Q |
| 19 | 5F12.v19 | VH.2/VL.2 | I48M/G43A |
| 20 | 5F12.v20 | VH.2/VL.3 | I48M/H49Y |
| 21 | 5F12.v21 | VH.2/VL.4 | I48M/I58V |
| 22 | 5F12.v22 | VH.2/VL.5 | I48M/K69T |
| 23 | 5F12.v23 | VH.2/VL.6 | I48M/Y71F |
| 24 | 5F12.v24 | VH.3/VL.1 | A67V/H38Q |
| 25 | 5F12.v25 | VH.3/VL.2 | A67V/G43A |
| 26 | 5F12.v26 | VH.3/VL.3 | A67V/H49Y |
| 27 | 5F12.v27 | VH.3/VL.4 | A67V/I58V |
| 28 | 5F12.v28 | VH.3/VL.5 | A67V/K69T |
| 29 | 5F12.v29 | VH.3/VL.6 | A67V/Y71F |
| 30 | 5F12.v30 | VH.4/VL.1 | L69I/H38Q |
| 31 | 5F12.v31 | VH.4/VL.2 | L69I/G43A |
| 32 | 5F12.v32 | VH.4/VL.3 | L69I/H49Y |
| 33 | 5F12.v33 | VH.4/VL.4 | L69I/I58V |
| 34 | 5F12.v34 | VH.4/VL.5 | L69I/K69T |
| 35 | 5F12.v35 | VH.4/VL.6 | L69I/Y71F |

TABLE 18

Recombinant ErbB2-ECD binding activity of humanized 5F12 variants

| Name | Binding ELISA (EC50, nM) |
|---|---|
| 5F12.v1 | 0.031 |
| 5F12.v2 | 0.034 |
| 5F12.v3 | 0.026 |
| 5F12.v4 | — * |
| 5F12.v5 | 0.028 |
| 5F12.v6 | 0.032 |
| 5F12.v7 | 0.152 |
| 5F12.v8 | 0.018 |
| 5F12.v9 | 0.023 |
| 5F12.v10 | 0.032 |
| 5F12.v11 | 0.028 |
| 5F12 chimeric | 0.043 |
| Trastuzumab | 0.030 |
| Pertuzumab | 0.039 |

* "—": indicates no binding activity

TABLE 19

VH and VL amino acid sequences of humanized versions of mouse anti-ErbB2 antibody 5G9

| SEQ ID NO | Protein region | Residue region | Sequence 12345678901234567890123456789012345678 90 |
|---|---|---|---|
| 39 | 5G9.VH.V1 | | EVQLVQSGAEVKKPGSSVKVSCKTSGYTFSSYTIHWVRQA PGQGLEWIGYINPSSDYTAYNQKFRDRATLTADQSTNTAY MELSSLRSEDTAVYYCARASAFSLDFWGQGTLVTVSS |
| 122 | 5G9.VH.V1 CDR-H1 | residues 31-35 of SEQ ID NO: 39 | SYTIH |
| 123 | 5G9.VH.V1 CDR-H2 | residues 50-66 of SEQ ID NO: 39 | YINPSSDYTAYNQKFRD |
| 124 | 5G9.VH.V1 CDR-H3 | resideus 99-106 of SEQ ID NO: 39 | ASAFSLDF |

TABLE 19-continued

VH and VL amino acid sequences of humanized versions of mouse anti-ErbB2 antibody 5G9

| SEQ ID NO | Protein region | Residue region | Sequence<br>1234567890123456789012345678901234567890 |
|---|---|---|---|
| 40 | 5G9.VH.1 | | EVQLVQSGAEVKKPGSSVKVSCKTSGYTFSSYTIHWVRQA<br>PGQGLEWIGYINPSSDYTAYNQKFRDRVTLTADQSTNTAY<br>MELSSLRSEDTAVYYCARASAFSLDFWGQGTLVTSS |
| 125 | 5G9.VH.1 CDR-H1 | residues 31-35 of SEQ ID NO: 39 | SYTIH |
| 126 | 5G9.VH.1 CDR-H2 | residues 50-66 of SEQ ID NO: 39 | YINPSSDYTAYNQKFRD |
| 127 | 5G9.VH.1 CDR-H3 | residues 99-106 of SEQ ID NO: 39 | ASAFSLDF |
| 41 | 5G9.VH.2 | | EVQLVQSGAEVKKPGSSVKVSCKTSGYTFSSYTIHWVRQA<br>PGQGLEWIGYINPSSDYTAYNQKFRDRATITADQSTNTAY<br>MELSSLRSEDTAVYYCARASAFSLDFWGQGTLVTSS |
| 128 | 5G9.VH.2 CDR-H1 | residues 31-35 of SEQ ID NO: 40 | SYTIH |
| 129 | 5G9.VH.2 CDR-H2 | residues 50-66 of SEQ ID NO: 40 | YINPSSDYTAYNQKFRF |
| 130 | 5G9.VH.2 CDR-H3 | residues 99-106 of SEQ ID NO: 40 | ASAFSLDF |
| 42 | 5G9.VH.3 | | EVQLVQSGAEVKKPGSSVKVSCKTSGYTFSSYTIHWVRQA<br>PGQGLEWIGYINPSSDYTAYNQKFRDRATLTADKSTNTAY<br>MELSSLRSEDTAVYYCARASAFSLDFWGQGTLVTSS |
| 131 | 5G9.VH.3 CDR-H1 | residues 31-35 of SEQ ID NO: 42 | SYTIH |
| 132 | 5G9.VH.3 CDR-H2 | residues 50-66 of SEQ ID NO: 42 | YINPSSDYTAYNQKFRD |
| 133 | 5G9.VH.3 CDR-H3 | residues 99-106 of SEQ ID NO: 42 | ASAFSLDF |
| 43 | 5G9.VH.4 | | EVQLVQSGAEVKKPGSSVKVSCKTSGYTFSSYTIHWVRQA<br>PGQGLEWIGYINPSSDYTAYNQKFRDRATLTADQSTSTAY<br>MELSSLRSEDTAVYYCARASAFSLDFWGQGTLVTSS |
| 134 | 5G9.VH.4 CDR-H1 | residues 31-35 of SEQ ID NO: 43 | SYTIH |
| 135 | 5G9.VH.4 CDR-H2 | residues 50-66 of SEQ ID NO: 43 | YINPSSDYTAYNQKFRD |
| 136 | 5G9.VH.4 CDR-H3 | residues 99-106 of SEQ ID NO: 43 | ASAFSLDF |
| 44 | 5G9.VH.5 | | EVQLVQSGAEVKKPGSSVKVSCKTSGYTFSSYTIHWVRQA<br>PGQGLEWMGYINPSSDYTAYNQKFRDRATLTADQSTNTAY<br>MELSSLRSEDTAVYYCARASAFSLDFWGQGTLVTSS |
| 137 | 5G9.VH.5 CDR-H1 | residues 31-35 of SEQ ID NO: 44 | SYTIH |
| 138 | 5G9.VH.5 CDR-H2 | residues 50-66 of SEQ ID NO: 44 | YINPSSDYTAYNQKFRD |
| 139 | 5G9.VH.5 CDR-H3 | residues 99-106 of SEQ ID NO: 44 | ASAFSLDF |
| 45 | 5G9.VL.V1 | | DIQMTQSPSSLSASVGDRVTITCKASHDIDRYIAWYQHKP<br>GKGPKLLIHYTSTLQPGIPSRFSGSGSGRDYTLTISSLQP<br>EDVATYYCLNYDNLLWTFGQGTKVEIK |
| 140 | 5G9.VL.V1 CDR-L1 | residues 24-34 of SEQ ID NO: 45 | KASHDIDRYIA |
| 141 | 5G9.VL.V1 CDR-L2 | residues 50-56 of SEQ ID NO: 45 | YTSTLQP |
| 142 | 5G9.VL.V1 CDR-L3 | residues 89-97 of SEQ ID NO: 45 | LNYDNLLWT |
| 46 | 5G9.VL.1 | | DIQMTQSPSSLSASVGDRVTITCKASHDIDRYIAWYQQKP<br>GKGPKLLIHYTSTLQPGIPSRFSGSGSGRDYTLTISSLQP<br>EDVATYYCLNYDNLLWTFGQGTKVEIK |
| 143 | 5G9.VL.1 CDR-L1 | residues 24-34 of SEQ ID NO: 46 | KASHDIDRYIA |
| 144 | 5G9.VL.1 CDR-L2 | residues 50-56 of SEQ ID NO: 46 | YTSTLQP |
| 145 | 5G9.VL.1 CDR-L3 | residues 89-97 of SEQ ID NO: 46 | LNYDNLLWT |
| 47 | 5G9.VL.2 | | DIQMTQSPSSLSASVGDRVTITCKASHDIDRYIAWYQHKP<br>GKVPKLLIHYTSTLQPGIPSRFSGSGSGRVYTLTISSLQP<br>EDVATYYCLNYDNLLWTFGQGTKVEIK |

TABLE 19-continued

VH and VL amino acid sequences of humanized versions of mouse anti-ErbB2 antibody 5G9

| SEQ ID NO | Protein region | Residue region | Sequence<br>12345678901234567890123456789012345678890 |
|---|---|---|---|
| 146 | 5G9.VL.2 CDR-L1 | residues 24-34 of SEQ ID NO: 47 | KASHDIDRYIA |
| 147 | 5G9.VL.2 CDR-L2 | residues 50-56 of SEQ ID NO: 47 | YTSTLQP |
| 148 | 5G9.VL.2 CDR-L3 | residues 89-97 of SEQ ID NO: 47 | LNYDNLLWT |
| 48 | 5G9.VL.3 | | DIQMTQSPSSLSASVGDRVTITCKASHDIDRYIAWYQHKP<br>GKGPKLLIYYTSTLQPGIPSRFSGSGSGRDYTLTISSLQP<br>EDVATYYCLNYDNLLWTFGQGTKVEIK |
| 149 | 5G9.VL.3 CDR-L1 | residues 24-34 of SEQ ID NO: 48 | KASHDIDRYIA |
| 150 | 5G9.VL.3 CDR-L2 | residues 50-56 of SEQ ID NO: 48 | YTSTLQP |
| 151 | 5G9.VL.3 CDR-L3 | residues 89-97 of SEQ ID NO: 48 | LNYDNLLWT |
| 49 | 5G9.VL.4 | | DIQMTQSPSSLSASVGDRVTITCKASHDIDRYIAWYQHKP<br>GKGPKLLIHYTSTLQPGVPSRFSGSGSGRDYTLTISSLQP<br>EDVATYYCLNYDNLLWTFGQGTKVEIK |
| 152 | 5G9.VL.4 CDR-L1 | residues 24-34 of SEQ ID NO: 49 | KASHDIDRYIA |
| 153 | 5G9.VL.4 CDR-L2 | residues 50-56 of SEQ ID NO: 49 | YTSTLQP |
| 154 | 5G9.VL.4 CDR-L3 | residues 89-97 of SEQ ID NO: 49 | LNYDNLLWT |
| 50 | 5G9.VL.5 | | DIQMTQSPSSLSASVGDRVTITCKASHDIDRYIAWYQHKP<br>GKGPKLLIHYTSTLQPGIPSRFSGSGSGTDYTLTISSLQP<br>EDVATYYCLNYDNLLWTFGQGTKVEIK |
| 155 | 5G9.VL.5 CDR-L1 | residues 24-34 of SEQ ID NO: 50 | KASHDIDRYIA |
| 156 | 5G9.VL.5 CDR-L2 | residues 50-56 of SEQ ID NO: 50 | YTSTLQP |
| 157 | 5G9.VL.5 CDR-L3 | residues 89-97 of SEQ ID NO: 50 | LNYDNLLWT |
| 51 | 5G9.VL.6 | | DIQMTQSPSSLSASVGDRVTITCKASHDIDRYIAWYQHKP<br>GKGPKLLIHYTSTLQPGIPSRFSGSGSGRDFTLTISSLQP<br>EDVATYYCLNYDNLLWTFGQGTKVEIK |
| 158 | 5G9.VL.6 CDR-L1 | residues 24-34 of SEQ ID NO: 51 | KASHDIDRYIA |
| 159 | 5G9.VL.6 CDR-L2 | residues 50-56 of SEQ ID NO: 51 | YTSTLQP |
| 160 | 5G9.VL.6 CDR-L3 | residues 89-97 of SEQ ID NO: 51 | LNYDNLLWT |

TABLE 20

Summary of humanized 5G9 antibodies generated and back mutations

| | Name | VH/VL Combination | Back Mutations in VH/VL |
|---|---|---|---|
| 1 | 5G9.v1 | VH.v1/VL.v1 | 0/0 |
| 2 | 5G9.v2 | VH.v1/VL.1 | 0/H38Q |
| 3 | 5G9.v3 | VH.v1/VL.2 | 0/G43V |
| 4 | 5G9.v4 | VH.v1/VL.3 | 0/H49Y |
| 5 | 5G9.v5 | VH.v1/VL.4 | 0/I58V |
| 6 | 5G9.v6 | VH.v1/VL.5 | 0/R69T |
| 7 | 5G9.v7 | VH.v1/VL.6 | 0/Y71F |
| 8 | 5G9.v8 | VH.1/VL.v1 | A67V/0 |
| 9 | 5G9.v9 | VH.2/VL.v1 | L69I/0 |
| 10 | 5G9.v10 | VH.3/VL.v1 | Q73K/0 |
| 11 | 5G9.v11 | VH.4/VL.v1 | N76S/0 |
| 12 | 5G9.v12 | VH.5/VL.v1 | I48M/0 |
| 13 | 5G9.v13 | VH.1/VL.1 | A67V/H38Q |
| 14 | 5G9.v14 | VH.1/VL.2 | A67V/G43V |
| 15 | 5G9.v15 | VH.1/VL.3 | A67V/H49Y |
| 16 | 5G9.v16 | VH.1/VL.4 | A67V/I58V |
| 17 | 5G9.v17 | VH.1/VL.5 | A67V/R69T |
| 18 | 5G9.v18 | VH.1/VL.6 | A67V/Y71F |
| 19 | 5G9.v19 | VH.2/VL.1 | L69I/H38Q |
| 20 | 5G9.v20 | VH.2/VL.2 | L69I/G43V |
| 21 | 5G9.v21 | VH.2/VL.3 | L69I/H49Y |
| 22 | 5G9.v22 | VH.2/VL.4 | L69I/I58V |
| 23 | 5G9.v23 | VH.2/VL.5 | L69I/R69T |
| 24 | 5G9.v24 | VH.2/VL.6 | C69I/Y71F |
| 25 | 5G9.v25 | VH.3/VL.1 | Q73K/H38Q |
| 26 | 5G9.v26 | VH.3/VL.2 | Q73K/G43V |
| 27 | 5G9.v27 | VH.3/VL.3 | Q73K/H49Y |
| 28 | 5G9.v28 | VH.3/VL.4 | Q73K/I58V |
| 29 | 5G9.v29 | VH.3/VL.5 | Q73K/R69T |
| 30 | 5G9.v30 | VH.3/VL.6 | Q73K/Y71F |
| 31 | 5G9.v31 | VH.4/VL.1 | N76S/H38Q |
| 32 | 5G9.v32 | VH.4/VL.2 | N76S/G43V |
| 33 | 5G9.v33 | VH.4/VL.3 | N76S/H49Y |
| 34 | 5G9.v34 | VH.4/VL.4 | N76S/I58V |
| 35 | 5G9.v35 | VH.4/VL.5 | N76S/R69T |
| 36 | 5G9.v36 | VH.4/VL.6 | N76S/Y71F |
| 37 | 5G9.v37 | VH.5/VL.1 | I48M/H38Q |
| 38 | 5G9.v38 | VH.5/VL.2 | I48M/G43V |

TABLE 20-continued

Summary of humanized 5G9 antibodies generated and back mutations

| | Name | VH/VL Combination | Back Mutations in VH/VL |
|---|---|---|---|
| 39 | 5G9.v39 | VH.5/VL.3 | I48M/H49Y |
| 40 | 5G9.v40 | VH.5/VL.4 | I48M/I58V |
| 41 | 5G9.v41 | VH.5/VL.5 | I48M/R69T |
| 42 | 5G9.v42 | VH.5/VL.6 | I48M/Y71F |

TABLE 21

Recombinant ErbB2-ECD binding activity of humanized 5G9 variants

| Name | Binding ELISA (EC50, nM) |
|---|---|
| 5G9.v1 | 0.031 |
| 5G9.v2 | 0.062 |
| 5G9.v3 | 0.023 |
| 5G9.v4 | 0.072 |
| 5G9.v5 | 0.013 |
| 5G9.v6 | 0.044 |
| 5G9.v7 | 0.053 |
| 5G9.v8 | 0.165 |
| 5G9.v9 | 0.054 |
| 5G9.v10 | 0.029 |
| 5G9.v11 | 0.081 |
| 5G9.v12 | 0.029 |
| 5G9 chimeric | 0.044 |
| Trastuzumab | 0.030 |
| Pertuzumab | 0.039 |

TABLE 22

Anti-tumor activity of the combinations in BT474 breast cancer xenograft model

| Treatment Group | T – C (Day) Tumor Volume 400 mm$^3$ | Day 4 post last dosage (Day 32 post treatment Tumor Volume Mean | T/C (%)$^a$ | P Value |
|---|---|---|---|---|
| Group 1 vehicle | — | 1064 | — | — |
| Group 2 Trastuzumab alone 3 mg/kg | 3.5 | 965 | 95 | 1 |
| Group 3 Trastuzumab + 4C9 (1.5 + 1.5) mg/kg | 4.5 | 743 | 67 | 0.232 |
| Group 4 Trastuzumab + 4H2 (1.5 + 1.5) mg/kg | 3.5 | 671 | 71 | 0.322 |
| Group 5 Trastuzumab + 4G6 (1.5 + 1.5) mg/kg | 5.5 | 647 | 62 | 0.148 |
| Group 6 Trastuzumab + 5F12 (1.5 + 1.5) mg/kg | 13 | 526 | 47 | 0.035* |
| Group 7 Trastuzumab + 5G9 (1.5 + 1.5) mg/kg | 14.5 | 525 | 53 | 0.001** |
| Group 8 Trastuzumab + Pertuzumab (1.5 + 1.5) mg/kg | 4 | 790 | 76 | 0.797 |

Note:
$^a$T/C % = T/C × 100%, where T and C are the mean tumor volume of the treated and control groups on day 35, respectively;
b. compared with the tumor volume of vehicle control by one-way ANOVA followed by multiple comparison procedures with Games-Howell method;
*P < 0.05 and
**P < 0.01 compared with vehicle control.

TABLE 23

Study design of Anti-Tumor Efficacy in NCI-N87 Gastric Xenograft Model

| Group ID | Treatment | Animal Number | Stage One (Day 0-Day 22) Dosage (mg/kg) | Route | Stage Two (Day 23-Day 57) Group | Dosage (mg/kg) | Route |
|---|---|---|---|---|---|---|---|
| 1 | Control | 14 | — | i.p./BIWx3W | Control | — | i.p./QWx4W |
| 2 | T-mAb | 7 | 5 | i.p./BIWx3W | T-mAb | 5 | i.p./QWx4W |
| 3 | T-mAb | 7 | 15 | i.p./BIWx3W | T-mAb | 15 | i.p./QWx4W |
| 4 | 5G9 | 7 | 5 | i.p./BIWx3W | 5G9 + T-mAb | 5 + 5 | i.p./QWx4W |
| 5 | 5G9 | 7 | 15 | i.p./BIWx3W | 5G9 | 15 | i.p./QWx4W |
| 6 | 5F12 | 7 | 5 | i.p./BIWx3W | 5F12+ T-mAb | 5 + 5 | i.p./QWx4W |
| 7 | 5F12 | 7 | 15 | i.p./BIWx3W | 5F12 | 15 | i.p./QWx4W |
| 8 | T-mAb + 5G9 | 7 | 5 + 5 | i.p./BIWx3W | T-mAb + 5G9 | — | No treatment |
| 9 | T-mAb + 5G9 | 7 | 15 + 15 | i.p./BIWx3W | T-mAb + 5G9 | — | No treatment |
| 10 | T-mAb + 5F12 | 7 | 5 + 5 | i.p./BIWx3W | T-mAb + 5F12 | — | No treatment |
| 11 | T-mAb + 5F12 | 7 | 15 + 15 | i.p./BIWx3W | T-mAb + 5F12 | — | No treatment |
| 12 | T-mAb + P-mAb | 7 | 5 + 5 | i.p./BIWx3W | T-mAb + P-mAb | — | No treatment |
| 13 | T-mAb + P-mAb | 7 | 15 + 15 | i.p./BIWx3W | T-mAb + P-mAb | — | No treatment |

Note:
T-mAb represents Trastuzumab; P-mAb represents Pertuzumab.

TABLE 24

The Result Summary of NCI-N87 Gastric Xenograft Model (Stage-one)

| Group ID | Treatment | Statistics | Day 0 | Day 5 | Day 8 | Day 12 | Day 15 | Day 19 | Day 22 |
|---|---|---|---|---|---|---|---|---|---|
| G1 | Vehicle | Mean ± | 115.52 ± | 168.23 ± | 218.18 ± | 290.91 ± | 365.7 ± | 442.5 ± | 518.75 ± |
|  |  | SEM | 10.55 | 18.01 | 21.69 | 29.16 | 40.48 | 47.47 | 53.71 |
| G2 | T-mAb | Mean ± | 118.4 ± | 122.03 ± | 123.58 ± | 149.79 ± | 174.71 ± | 192.37 ± | 227.71 ± |
|  | 5 mg/kg | SEM | 18.65 | 17.97 | 20.79 | 25.42 | 27.36 | 36.07 | 43.59 |
|  |  | TGI % |  | 27.46 | 43.36 | 48.51 | 52.23 | 56.53 | 56.10 |
| G3 | T-mAb | Mean ± | 117.92 ± | 140.91 ± | 114.46 ± | 127.98 ± | 143.31 ± | 164.12 ± | 190.75 ± |
|  | 15 mg/kg | SEM | 18.6 | 22.83 | 29.58 | 25.19 | 28.96 | 36.69 | 44.4 |
|  |  | TGI % |  | 16.24 | 47.54 | 56.01 | 60.81 | 62.91 | 63.23 |
| G4 | 5G9 | Mean ± | 115.3 ± | 165.67 ± | 196.08 ± | 248.86 ± | 301.27 ± | 373.8 ± | 424.57 ± |
|  | 5 mg/kg | SEM | 13.98 | 17.86 | 18.25 | 14.3 | 34.26 | 41.13 | 54.23 |
|  |  | TGI % |  | 1.52 | 10.13 | 14.45 | 17.62 | 15 53 | 18.16 |
| G5 | 5G9 | Mean ± | 116.22 ± | 158.54 ± | 182.88 ± | 211.15 ± | 250.05 ± | 277.41 ± | 376.81 ± |
|  | 15 mg/kg | SEM | 13.17 | 16.28 | 26.19 | 38.13 | 50.17 | 61.38 | 74.48 |
|  |  | TGI % |  | 5.76 | 16.18 | 27.42 | 31.62 | 37.31 | 27.36 |
| G6 | 5F12 | Mean ± | 114.37 ± | 175.71 ± | 185.17 ± | 272.23 ± | 333.27 ± | 358.09 ± | 386.92 ± |
|  | 5 mg/kg | SEM | 17.64 | 25.35 | 28.06 | 43.88 | 52.07 | 56.08 | 60.82 |
|  |  | TGI % |  | −4.45 | 15.13 | 6.42 | 8.87 | 19.08 | 25.41 |
| G7 | 5F12 | Mean ± | 116.96 ± | 155.32 ± | 165.47 ± | 222.08 ± | 233.97 ± | 305.65 ± | 319.15 ± |
|  | 15 mg/kg | SEM | 14.23 | 17.92 | 25.68 | 32.48 | 33.24 | 49.43 | 59.16 |
|  |  | TGI % |  | 7.67 | 24.16 | 23.66 | 36.02 | 30.93 | 38.48 |
| G8 | T-mAb 5 mg/kg + 5G9 5 mg/kg | Mean ± | 114.07 ± | 79.59 ± | 59.12 ± | 40.75 ± | 19.18 ± | 20 ± | 8.75 ± |
|  |  | SEM | 13.95 | 12.42 | 7.92 | 10.11 | 7.4 | 8.5 | 4.25 |
|  |  | TGI % |  | 52.69 | 72.90 | 85.99 | 94.76 | 95.48 | 98.31 |
| G9 | T-mAb 15 mg/kg + 5G9 5 mg/kg | Mean ± | 120.44 ± | 60.74 ± | 36.1 ± | 20.91 ± | 12.87 ± | 10.86 ± | 7.23 ± |
|  |  | SEM | 17.74 | 9.24 | 5.92 | 4.2 | 5.77 | 3.27 | 2.83 |
|  |  | TGI % |  | 63.89 | 83.45 | 92.81 | 96.48 | 97.55 | 98.61 |
| G10 | T-mAb 5 mg/kg + 5F12 5 mg/kg | Mean ± | 112.42 ± | 102.28 ± | 93.81 ± | 63.85 ± | 59.98 ± | 38.6 ± | 35.32 ± |
|  |  | SEM | 13.87 | 20.65 | 37.05 | 22.89 | 29.92 | 18.25 | 17.7 |
|  |  | TGI % |  | 39.20 | 57.00 | 78.05 | 83.60 | 91.28 | 93.19 |
| G11 | T-mAb 15 mg/kg + 5F12 15 mg/kg | Mean ± | 118.52 ± | 70.92 ± | 33.88 ± | 13.46 ± | 10.34 ± | 3.61 ± | 1.45 ± |
|  |  | SEM | 18.24 | 20.04 | 9.04 | 1.78 | 3.2 | 1.38 | 1.45 |
|  |  | TGI % |  | 57.84 | 84.47 | 95.37 | 97.17 | 99.18 | 99.72 |
| G12 | T-mAb 5 mg/kg + P-mAb 5 mg/kg | Mean ± | 111.59 ± | 115.29 ± | 100.32 ± | 81.6 ± | 72.16 ± | 58.78 ± | 46.83 ± |
|  |  | SEM | 13.88 | 21.87 | 22.35 | 26.15 | 23.46 | 17.13 | 14.48 |
|  |  | TGI % |  | 31.47 | 54.02 | 71.95 | 80.27 | 86.72 | 90.97 |
| G13 | T-mAb 15 mg/kg + P-mAb 15 mg/kg | Mean ± | 120.01 ± | 93.51 ± | 52.66 ± | 35.47 ± | 22.32 ± | 25.76 ± | 21.41 ± |
|  |  | SEM | 14.98 | 13.84 | 8.42 | 8.01 | 2.75 | 5.66 | 1.83 |
|  |  | TGI % |  | 44.42 | 75.86 | 87.81 | 93.90 | 94.18 | 95.87 |
| T-Test | G2 vs G1 | Mean ± | 0.45 | 0.04 | 0.00 | 0.00 | 0.00 | 0.00 | 0.00 |
|  | G3 vs G2 | SEM | 0.49 | 0.26 | 0.40 | 0.28 | 0.22 | 0.30 | 0.28 |
|  | G12 vs G3 |  | 0.395 | 0.217 | 0.355 | 0.113 | 0.040 | 0.012 | 0.005 |
|  | G8 vs G3 |  | 0.436 | 0.018 | 0.048 | 0.004 | 0.001 | 0.001 | 0.001 |
|  | G10 vs G3 |  | 0.408 | 0.117 | 0.335 | 0.042 | 0.034 | 0.005 | 0.003 |
|  | G8 vs G12 |  | 0.451 | 0.091 | 0.054 | 0.085 | 0.026 | 0.033 | 0.013 |
|  | G10 vs G12 |  | 0.484 | 0.337 | 0.441 | 0.309 | 0.377 | 0.218 | 0.312 |
|  | G11 vs G13 |  | 0.475 | 0.186 | 0.077 | 0.010 | 0.007 | 0.001 | 0.000 |
|  | G9 vs G13 |  | 0.493 | 0.036 | 0.067 | 0.067 | 0.082 | 0.021 | 0.001 |

Note:
Tumor Growth Inhibition (TGI) index = (1 − mean volume of treated tumors/mean volume of control tumors) × 100%

TABLE 25

The Result Summary of NCI-N87 Gastric Xenograft Model (Stage-Two)

| Group ID | Treatment | Statistics | Stage-1 Day 22 | Stage-2 Day 26 | Day 29 | Day 33 | Day 36 | Day 40 | Day 43 | Day 50 | Day 57 | Progression rate (%) |
|---|---|---|---|---|---|---|---|---|---|---|---|---|
| G1 | Vehicle | Mean ± | 518.75 ± | 618.36 ± | 696.17 ± | 822.21 ± | 1009.65 ± | 1189.92 ± | 1321.09 ± | 1653.8 ± | 2143.52 ± | 246.93 |
|  |  | SEM | 53.71 | 63.98 | 76.01 | 91.64 | 99.52 | 128.25 | 139.61 | 164.8 | 213.43 |  |

TABLE 25-continued

The Result Summary of NCI-N87 Gastric Xenograft Model (Stage-Two)

| | | | Stage-1 | Stage-2 | | | | | | | | |
|---|---|---|---|---|---|---|---|---|---|---|---|---|
| Group ID | Treatment | Statistics | Day 22 | Day 26 | Day 29 | Day 33 | Day 36 | Day 40 | Day 43 | Day 50 | Day 57 | Progression rate (%) |
| G3 | T-mAb 15 mg/kg | Mean ± SEM TGI % | 190.75 ± 44.4 63.23 | 226.09 ± 62.84 63.44 | 220.27 ± 55.69 68.36 | 257.53 ± 66.4 68.68 | 327.48 ± 79.98 67.56 | 378.17 ± 101.66 68.22 | 436.3 ± 118.49 66.97 | 571.26 ± 156.93 65.46 | 888.57 ± 256.13 58.55 | 292.92<br><br>−7.71 |
| G4 | 5G9 5 mg/kg + T-mAb 5 mg/kg | Mean ± SEM TGI % | 424.57 ± 54.23 18.16 | 445.5 ± 65.8 27.95 | 461.01 ± 64.42 33.78 | 517.31 ± 72.59 37.08 | 581.56 ± 94.54 42.40 | 677.45 ± 112.14 43.07 | 715.12 ± 146.27 43.52 | 934.94 ± 207.36 43.47 | 1305.11 ± 319.49 39.11 | 192.60<br><br>39.93 |
| G6 | 5F12 5 mg/kg + T-mAb 5 mg/kg | Mean ± SEM TGI % | 386.92 ± 60.82 25.41 | 380.94 ± 66.26 38.40 | 416.08 ± 87.39 40.23 | 411.83 ± 94.48 49.91 | 502.99 ± 114.18 50.18 | 507.83 ± 134.17 57.32 | 523.35 ± 143.98 60.38 | 675.67 ± 191.35 59.14 | 879.9 ± 257.65 58.95 | 130.97<br><br>53.52 |
| T-Test | G4 vs G3 G6 vs G3 | Mean ± SEM | 0.003 0.012 | 0.016 0.058 | 0.008 0.042 | 0.011 0.103 | 0.031 0.116 | 0.036 0.228 | 0.063 0.324 | 0.094 0.340 | 0.165 0.491 | |

Note:
T-mAb: Trastuzumab; Progression rate = (Day57 − Day26)/Day26 × 100.

TABLE 26

Cancer Progression Rate of NCI-N87 Gastric Xenograft Model (Stage-Two)

| Group ID | Treatment (mg/kg) | Statistics | Day 26 | Day 57 | Progression rate (%) | TV D26 vs TV D57 P value (T-Test) |
|---|---|---|---|---|---|---|
| G8 | T-mAb 5 + 5G9 5 | Mean ± SEM<br>TGI % | 6.19 ± 2.29<br>99.00 | 11.82 ± 9.93<br>99.45 | 93.55<br>0.45 | 0.278 |
| | T-mAb 5 + 5F12 5 | Mean ± SEM<br>TGI % | 18.63 ± 7.87<br>96.99 | 42.01 ± 19.98<br>98.04 | 125.81<br>1.08 | P = 0.064 |
| | T-mAb 5 + P-mAb 5 | Mean ± SEM<br>TGI % | 54.16 ± 21.53<br>91.24 | 243.91 ± 102.41<br>88.62 | 351.85<br>−2.87 | P = 0.030 |

Note:
Recovery rate = (Day57 − Day26)/Day26 × 100; TV: Tumor Volume

TABLE 27

Internalization rate of ErbB2 antibodies of this invention

| FITC Signal | 2-hour | p value |
|---|---|---|
| Trastuzumab FITC | 12.20 ± 2.32 | |
| Pertuzumab FITC | 8.87 ± 0.51 | 0.105 |
| 4C9 FITC | 23.79 ± 2.20 | *0.0055 |
| 4H2 FITC | 17.72 ± 3.20 | 0.105 |
| 4G6 FITC | 18.51 ± 3.51 | 0.089 |
| 5F12 FITC | 22.55 ± 2.39 | *0.0104 |
| 5G9 FITC | 20.61 ± 2.38 | *0.022 |

TABLE 28

Internalization rate of ErbB2 antibody combinations of this invention

| APC Signal | 2-hour | p value |
|---|---|---|
| Trastuzumab APC | 13.54 ± 1.38 | |
| Trastuzumab APC + Pertuzumab FITC | 15.30 ± 1.30 | 0.22 |
| Trastuzumab APC + 4C9 FITC | 39.34 ± 5.08 | *0.0043 |
| Trastuzumab APC + 4H2 FITC | 37.71 ± 3.82 | *0.002 |
| Trastuzumab APC + 4G6 FITC | 44.41 ± 11.84 | *0.03 |
| Trastuzumab APC + 5F12 FITC | 35.53 ± 1.17 | *0.00013 |
| Trastuzumab APC + 5G9 FITC | 39.40 ± 2.97 | *0.00069 |

TABLE 29

Study Design of HuPrime® Gastric Cancer Xenograft Model

| Group ID | N | Compound | Dose (mg/kg) | Dosing Route | Dosing Volume (ml/kg) | Dosing schedule* |
|---|---|---|---|---|---|---|
| 1 | 6 | PBS | — | i.v. | 10 | BIW × 4 weeks |
| 2 | 6 | T-mab | 6 | i.v. | 10 | BIW × 4 weeks |
| 3 | 6 | T-mab + P-mAb | 3 + 3 | i.v. | 10 | BIW × 4 weeks |

TABLE 29-continued

Study Design of HuPrime ® Gastric Cancer Xenograft Model

| Group ID | N | Compound | Dose (mg/kg) | Dosing Route | Dosing Volume (ml/kg) | Dosing schedule* |
|---|---|---|---|---|---|---|
| 4 | 6 | T-mab + 5G9 | 3 + 3 | i.v. | 10 | BIW × 4 weeks |
| 5 | 6 | T-mab + 5F12 | 3 + 3 | i.v. | 10 | BIW × 4 weeks |

Note:
N: animal number per group; Dosing frequency of all test compounds was adjusted from BIW to QW per week through day 14(day 0, 3, 7, 14), and dosage of them was cut in half since day 21(day 21, 28); T-mAb represents Trastuzumab; P-mAb represents Pertuzumab.

TABLE 30

Anti-Tumor Efficacy of Antibody Combination of This Invention in Trastuzumab-Resistant Gastric Model - HuPrime ® Gastric Cancer Xenograft Model

| Treatment | Tumor size (mm³)[a] on Day 0 of treatment | Tumor size (mm³)[a] on Day 35 of treatment | T/C (%)[b] | T – C (days) at 500 mm³ | P value[c] |
|---|---|---|---|---|---|
| PBS, BIW | 200.6 ± 17.4 | 1201.1 ± 142.6 | — | — | — |
| T-mab, 6/3 mg/kg, BIW/QW | 199.9 ± 18.6 | 932.7 ± 215.1 | 77.7 | 3 | 0.161 |
| (T-mab + P-mAb) 6/3 mg/kg, BIW/QW | 200.0 ± 18.3 | 994.6 ± 209.9 | 82.8 | 3 | 0.217 |
| (T-mab + 5F12) 6/3 mg/kg, BIW/QW | 200.0 ± 17.9 | 691.6 ± 67.3 | 57.6 | 8 | 0.004** |
| (T-mab + 5G9) 6/3 mg/kg, BIW/QW | 200.2 ± 17.8 | 608.8 ± 97.2 | 50.7 | 12 | 0.003** |

Note:
[a] Mean ± SEM;
[b] T/C % = T/C × 100%, where T and C are the mean tumor volume of the treated and control groups on day 35, respectively;
[c] compared with the tumor volume of vehicle control by T-test
(*P < 0.05 and **P < 0.01)
T-mAb represents Trastuzumab; P-mAb represents Pertuzumab.

TABLE 31

Amino acid sequences

| SEQ ID NO | Description | Sequence | CDR Set |
|---|---|---|---|
| 17 | VH 4C9 | QVQLQQSGAELARPGASVKMSCKASGYTFTSYT MHWVKQRPGQGLDWIGYINPSSGYTTYNQKFKD KATLTADKSSSTAYMQLSSLASADSAVYYCARA SAYSLDYWGQGTTLTVSS | |
| 18 | VL 4C9 | DIQMTQSPSSLSASLGGRVTITCKASHDIDRYI AWYQHKPGKGPRLLIHYTSTLQPGIPSRFSGSG SGRDYSFSISNLEPEDIATYYCLKYDNLLWTFG GGTKLEIT | |
| 19 | VH 4H2 | QVQLQQSGAELARPGASVKMSCKASGFTFTSYT IHWVKQRPGQGLDWIGYINPSSGYTTYNQRFKD KATLTADKSSSTAYMQLSSLTSADSAVYYCARA SAYSLDYWGQGTTLTVSS | |
| 20 | VL 4H2 | DIQMTQSPSSLSASLGGKVTITCKASQDIDRYI AWYQHIPGKGPRLLIHYTSTLQPGIPSRFSGSG SGRNYSFSISNLEPEDIATYYCLKYDNLLSTFG GGTKLEIK | |
| 21 | VH 4G6 | QVQLQQSGAELARPGASVKMSCKASGYTFTSYT MHWVKQRPGQGLEWIGYINPSSAYTNYNQKFKD KATLTADKSSSTANMQLNLTSEDSAVYYCARAS AYSLDYWGQGTALTVSS | |
| 22 | VL 4G6 | DIQMTQSPSSLSASLGGKVTITCKASQDINKYI AWYQHKPGKGPRLLIHSTSTLYPGIPSRFSGSG SGRDYSFRITNLEPEDIATYYCLQYDNLLWTFG GGTKVGIR | |
| 23 | VH 5F12 | QVQLQQSGAELARPGASVKMSCKASGYTFTSYT MHWIKQRPGQGLEWIGYINPSSSYTNYNQNFKD ATLTADKSSSTANMQLNSLTSEDSAVYYCARAS SYSLDYWGQGTALTVSS | |
| 24 | VL 5F12 | DIQMTQSPSSLSTSLGGKVTITCKASQDINKYI AWYQHKPGKGPRLLIHSTSTLYPGIPSRFSGSG SGKDYSFRITNLEPEDIATYYCLQYDNLLWTFG GGTKLGIR | |

TABLE 31-continued

Amino acid sequences

| SEQ ID NO | Description | Sequence | CDR Set |
|---|---|---|---|
| 25 | VH 5G9 | QVQLQQSGAELARPGASVKMSCKTSGYTFSSYT IHWVKQRPGQGLDWIGYINPSSDYTAYNQKFRD KATLTADQSSNTAYMQLSSLASADSAVYYCARA SAFSLDFWGQGTTLTVSS | |
| 26 | VL 5G9 | DIQMTQSPSSLSASLGGKVTISCKASHDIDRYI AWYQHKPGKGPRLLIHYTSTLQPGIPSRFSGSG SGRDYSFSISNLEPEDVATYYCLNYDNLLSTFG GGTKLEIT | |
| 27 | 5F12.VH.V1 | EVQLVQSGAEVKKPGSSVKVSCKASGYTFTSYT MHWIRQAPGQGLEWIGYINPSSSYTNYNQNFKD RATLTADKSTSTAYMELSSLRSEDTAVYYCARA SSYSLDYWGQGTLVTVSS | |
| 28 | 5F12.VH.1 | EVQLVQSGAEVKKPGSSVKVSCKASGYTFTSYT MHWVRQAPGQGLEWIGYINPSSSYTNYNQNFKD RATLTADKSTSTAYMELSSLRSEDTAVYYCARA SSYSLDYWGQGTLVTVSS | |
| 29 | 5F12.VH.2 | EVQLVQSGAEVKKPGSSVKVSCKASGYTFTSYT MHWIRQAPGQGLEWMHGINPSSSYTNYNQNFKD RATLTADKSTSTAYMELSSLRSEDTAVYYCARA SSYSLDYWGQGTLVTVSS | |
| 30 | 5F12.VH.3 | EVQLVQSGAEVKKPGSSVKVSCKASGYTFTSYT MHWIRQAPGQGLEWIGYINPSSSYTNYNQNFKD RVTLTADKSTSTAYMELSSLRSEDTAVYYCARA SSYSLDYWGQGTLVTVSS | |
| 31 | 5F12.VH.4 | EVQLVQSGAEVKKPGSSVKVSCKASGYTFTSTY MHWIRQAPGQGLEWIGYINPSSSYTNYNQNFKD RATITADKSTSTAYMELSSLRSEDTAVYYCARA SSYSLDYWGQGTLVTVSS | |
| 32 | 5F12.VL.V1 | DIQMTQSPSSLSASVGDRVTITCKASQDINKYI AWYQHIPGKGPKLLIHSTSTLYPGIPSRFSGSG SGKDYTFTISSLQPEDIATYYCLQYDNLLWTFG QGTKVEIK | |
| 33 | 5F12.VL.1 | DIQMTQSPSSLSASVGDRVTITCKASQDINKYI AWYQQKPGKGPKLLIHSTSTLYPGIPSRFSGSG SGKDYTFTISSLQPEDIATYYCLQYDNLLSTFG QGTKVEIK | |
| 34 | 5F12.VL.2 | DIQMTQSPSSLSASVGDRVTITCKASQDINKYI AWYQHKPGKAPKLLIHSTSTLYPGIPSRFSGSG SGKDYTFTISSLQPEDIATYYCLQYDNLLSTFG QGTKVEIK | |
| 35 | 5F12 VH.3 | DIQMTQSPSSLSASVGDRVTITCKASQDINKYI AWYQHKPGKGPKLLIYSTSTLYPGIPSRFSGSG SGKDYTFTISSLQPEDIATYYCLQYDNLLWTFG QGTKVEIK | |
| 36 | 5F12 VH.4 | DIQMTQSPSSLSASVGDRVTITCKASQDINKYI AWYQHKPGKGPKLLIHSTSTLYPGVPSRFSGSG SGKDYTFTISSLQPEDIATYYCLQYDNLLWTFG QGTKVEIK | |
| 37 | 5F12.VL.5 | DIQMTQSPSSLSASVGDRVTITCKASQDINKYI AWYQHKPGKGPKLLIHSTSTLYPGIPSRFSGSG SGTDYTFTISSLQPEDIATYYCLQYDNLLSTFG QGTKVEIK | |
| 38 | 5F12.VL.6 | DIQMTQSPSSLSASVGDRVTITCKASQDINKYI AWYQHKPGKGPKLLIHSTSTLYPGIPSRFSGSG SGKDFTFTISSLQPEDIATYYCLQYDNLLWTFG QGTKVEIK | |
| 39 | 59G.VH.V1 | EVQLVQSGAEVKKPGSSVKVSCKTSGYTFSSYT IHWVRQAPGQGLEWIGYINPSSDYTAYNQKFRD RATLTADQSTNTAYMELSSLRSEDTAVYYCARA SAFSLDFWGQGTLVTVSS | |

TABLE 31-continued

Amino acid sequences

| SEQ ID NO | Description | Sequence | CDR Set |
|---|---|---|---|
| 40 | 5G9.VH.1 | EVQLVQSGAEVKKPGSSVKVSCKTSGYTFSSYT IHWVRQAPGQGLEWIGYINPSSDYTAYNQKFRD RVTLTADQSTNTAYMELSSLRSEDTAVYYCARA SAFSLDFWGQGTLVTVSS | |
| 41 | 5G9.VH.2 | EVQLVQSGAEVKKPGSSVKVSCKTSGYTFSSYT IHWVRQAPGQGLEWIGYINPSSDYTAYNQKFRD RATITADQSTNTAYMELSSLRSEDTAVYYCARA SAFSLDFWGQGTLVTVSS | |
| 42 | 5G9.VH.3 | EVQLVQSGAEVKKPGSSVKVSCKTSGYTFSSYT IHWVRQAPGQGLEWIGYINPSSDYTAYNQKFRD RATLTADKSTNTAYMELSSLRSEDTAVYYCARA SAFSLDFWGQGTLVTVSS | |
| 43 | 5G9.VH.4 | EVQLVQSGAEVKKPGSSVKVSCKTSGYTFSSYT IHWVRQAPGQGLEWIGYINPSSDYTAYNQKFRD RATLTADQSTSTAYMELSSLRSEDTAVYYCARA SAFSLDFWGQGTLVTVSS | |
| 44 | 5G9.VH.6 | EVQLVQSGAEVKKPGSSVKVSCKTSGYTFSSYT IHWVRQAPGQGLEWMHRINPSSDYTAYNQKFRD RATLTADQSTNTAYMELSSLRSEDTAVYYCARA SAFSLDFWGQGTLVTVSS | |
| 45 | 5G9.VL.V1 | DIQMTQSPSSLSASVGDRVTITCKASHDIDRYI AWYQHKPGKGPKLLIHYTSTLQPGIPSRFSGSG SGRDYTLTISSLQPEDVATYYCLNYDNLLWTFG QGTKVEIK | |
| 46 | 5G9.VL.1 | DIQMTQSPSSLSASVGDRVTITCKASHDIDRYI AWYQQKPGKGPKLLIHYTSTLQPGIPSRFSGSG SGRDYTLTISSLQPEDVATYYCLNYDNLLWTFG QGTKVEIK | |
| 47 | 5G9.VL.2 | DIQMTQSPSSLSASVGDRVTITCKASHDIDRYI AWYQHKPGKVPKLLIHYTSTLQPGIPSRFSGSG SGRDYTLTISSLQPEDVATYYCLNYDNLLWTFG QGTKVEIK | |
| 48 | 5G9.VL.3 | DIQMTQSPSSLSASVGDRVTITCKASHDIDRYI AWYQHKPGKGPKLLIYYTSTLQPGIPSRFSGSG SGRDYTLTISSLQPEDVATYYCLNYDNLLWTFG QGTKVEIK | |
| 49 | 5G9.VL.4 | DIQMTQSPSSLSASVGDRVTITCKASHDIDRYI AWYQHKPGKGPKLLIHYTSTLQPGVPSRFSGSG SGRDYTLTISSLQPEDVATYYCLNYDNLLWTFG QGTKVEIK | |
| 50 | 5G9.VL.5 | DIQMTQSPSSLSASVGDRVTITCKASHDIDRYI AWYQHKPGKGPKLLIHYTSTLQPGIPSRFSGSG SGTDYTLTISSLQPEDVATYYCLNYDNLLWTFG QGTKVEIK | |
| 51 | 5G9.VL.6 | DIQMTQSPSSLSASVGDRVTITCKASHDIDRYI AWYQHKPGKGPKLLIHYTSTLQPGIPSRFSGSG SGRDFTLTISSLQPEDVATYYCLNYDNLLWTFG QGTKVEIK | |
| 56 | VH 4C9 CDR-H1 | SYTMH | 4C9 VH |
| 57 | VH 4C9 CDR-H2 | YINPSSGYTTYNQKFKD | |
| 58 | VH 4C9 CDR-H3 | ASAYSLDY | |
| 59 | VL 4C9 CDR-L1 | KASHDIDRYIA | 4C9 VL |
| 60 | VL 4C9 CDR-L2 | YTSTLQP | |
| 61 | VL 4C9 CDR-L3 | LKYDNLLWT | |
| 62 | VH 4H2 CDR-H1 | SYTIH | 4H2 VH |
| 63 | VH 4H2 CDR-H2 | YINPSSGYTTYNQRFKD | |
| 64 | VH 4H2 CDR-H3 | ASAYSLDY | |
| 65 | VL 4H2 CDR-L1 | KASQDIDRYIA | 4H2 VL |
| 66 | VL 4H2 CDR-L2 | YTSTLQP | |
| 67 | VL 4H2 CDR-L3 | LKYDNLLWT | |

TABLE 31-continued

Amino acid sequences

| SEQ ID NO | Description | Sequence | CDR Set |
|---|---|---|---|
| 68 | VH 4G6 CDR-H1 | SYTMH | 4G6 VH |
| 69 | VH 4G6 CDR-H2 | YINPSSAYTNYNQKFKD | |
| 70 | VH 4G6 CDR-H3 | ASAYSLDY | |
| 71 | VL 4G6 CDR-L1 | KASQDINKYIA | 4G6 VL |
| 72 | VL 4G6 CDR-L2 | STSTLYP | |
| 73 | VL 4G6 CDR-L3 | LQYDNLLWT | |
| 74 | VH 5F12 CDR-H1 | SYTMH | 5F12 VH |
| 75 | VH 5F12 CDR-H2 | YINPSSYTNYNQNFKD | |
| 76 | VH 5F12 CDR-H3 | ASSYSLDY | |
| 77 | VL 5F12 CDR-L1 | KASQDINKYIA | 5F12 VL |
| 78 | VL 5F12 CDR-L2 | STSTLYP | |
| 79 | VL 5F12 CDR-L3 | LQYDNLLWT | |
| 80 | VH 5G9 CDR-H1 | SYTIH | 5G9 VH |
| 81 | VH 5G9 CDR-H2 | YINPSSDYTAYNQKFRD | |
| 82 | VH 5G9 CDR-H3 | ASAFSLDF | |
| 83 | VL 5G9 CDR-L1 | KASHDIDRYIA | 5G9 VL |
| 84 | VL 5G9 CDR-L2 | YTSTLQP | |
| 85 | VL 5G9 CDR-L3 | LNYDNLLWT | |
| 86 | 5F12.VH.V1 CDR-H1 | SYTMH | 5F12.VH.V1 |
| 87 | 5F12.VH.V1 CDR-H2 | YINPSSSYTNYNQNFKD | |
| 88 | 5F12.VH.V1 CDR-H3 | ASSYSLDY | |
| 89 | 5F12.VH.1 CDR-H1 | SYTMH | 5F12.VH.1 |
| 90 | 5F12.VH.1 CDR-H1 | YINPSSSYTNYNQNFKD | |
| 91 | 5F12.VH.1 CDR-H1 | ASSYSLDY | |
| 92 | 5F12.VH.2 CDR-H1 | SYTMH | 5F12.VH.2 |
| 93 | 5F12.VH.2 CDR-H1 | YINPSSYTNYNQNFKD | |
| 94 | 5F12.VH.2 CDR-H1 | ASSYSLDY | |
| 95 | 5F12.VH.3 CDR-H1 | SYTMH | 5F12.VH.3 |
| 96 | 5F12.VH.3 CDR-H1 | YINPSSSYTNYNQNFKD | |
| 97 | 5F12.VH.3 CDR-H1 | ASSYSLDY | |
| 98 | 5F12.VH.4 CDR-H1 | SYTMH | 5F12.VH.4 |
| 99 | 5F12.VH.4 CDR-H1 | YINPSSSYTNYNQNFKD | |
| 100 | 5F12.VH 4 CDR-H1 | ASSYSLDY | |
| 101 | 5F12.VL.V1 CDR-L1 | KASQDINKYIA | 5F12.VL.V1 |
| 102 | 5F12.VL.V1 CDR-L2 | STSTLYP | |
| 103 | 5F12.VL.V1 CDR-L3 | LQYDNLLWT | |
| 104 | 5F12.VL.1 CDR-L1 | KASQDINKYIA | 5F12.VL.1 |
| 105 | 5F12.VL.1 CDR-L2 | STSTLYP | |
| 106 | 5F12.VL.1 CDR-L3 | LQYDNLLWT | |
| 107 | 5F12.VL.2 CDR-L1 | KASQDINKYIA | 5F12.VL.2 |
| 108 | 5F12.VL.2 CDR-L2 | STSTLYP | |
| 109 | 5F12.VL.2 CDR-L3 | LQYDNLLWT | |
| 110 | 5F12.VL.3 CDR-L1 | KASQDINKYIA | 5F12.VL.3 |
| 111 | 5F12.VL.3 CDR-L2 | STSTLYP | |
| 112 | 5F12.VL.3 CDR-L3 | LQYDNLLWT | |
| 113 | 5F12.VL.4 CDR-L1 | KASQDINKYIA | 5F12.VL.4 |
| 114 | 5F12.VL.4 CDR-L2 | STSTLYP | |
| 115 | 5F12.VL.4 CDR-L3 | LQYDNLLWT | |
| 116 | 5F12.VL.5 CDR-L1 | KASQDINKYIA | 5F12.VL.5 |
| 117 | 5F12.VL.5 CDR-L2 | STSTLYP | |
| 118 | 5F12.VL.5 CDR-L3 | LQYDNLLWT | |
| 119 | 5F12.VL.6 CDR-L1 | KASQDINKYIA | 5F12.VL.6 |
| 120 | 5F12.VL.6 CDR-L2 | STSTLYP | |
| 121 | 5F12.VL.6 CDR-L3 | LQYDNLLWT | |
| 122 | 5G9.VH.V1 CDR-H1 | SYTIH | 5G9.VH.V1 |
| 123 | 5G9.VH.V1 CDR-H2 | YINPSSDYTAYNQKFRD | |
| 124 | 5G9.VH.V1 CDR-H3 | ASAFSLDF | |

TABLE 31-continued

Amino acid sequences

| SEQ ID NO | Description | Sequence | CDR Set |
|---|---|---|---|
| 125 | 5G9.VH.1 CDR-H1 | SYTIH | 5G9.VH.1 |
| 126 | 5G9.VH.1 CDR-H2 | YINPSSDYTAYNQKFRD | |
| 127 | 5G9.VH.1 CDR-H3 | ASAFSLDF | |
| 128 | 5G9.VH.2 CDR-H1 | SYTIH | 5G9.VH.2 |
| 129 | 5G9.VH.2 CDR-H2 | YINPSSDYTAYNQKFRD | |
| 130 | 5G9.VH.2 CDR-H3 | ASAFSLDF | |
| 131 | 5G9.VH.3 CDR-H1 | SYTIH | 5G9.VH.3 |
| 132 | 5G9.VH.3 CDR-H2 | YINPSSDYTAYNQKFRD | |
| 133 | 5G9.VH.3 CDR-H3 | ASAFSLDF | |
| 134 | 5G9.VH.4 CDR-H1 | SYTIH | 5G9.VH.4 |
| 135 | 5G9.VH.4 CDR-H2 | YINPSSDYTAYNQKFRD | |
| 136 | 5G9.VH.4 CDR-H3 | ASAFSLDF | |
| 137 | 5G9.VH.5 CDR-H1 | SYTIH | 5G9.VH.5 |
| 138 | 5G9.VH.5 CDR-H2 | YINPSSDYTAYNQKFRD | |
| 139 | 5G9.VH.5 CDR-H3 | ASAFSLDF | |
| 140 | 5G9.VL.V1 CDR-L1 | KASHDIDRYIA | 5G9.VL.V1 |
| 141 | 5G9.VL.V1 CDR-L2 | YTSTLQP | |
| 142 | 5G9.VL.V1 CDR-L3 | LNYDNLLWT | |
| 143 | 5G9.VL.1 CDR-L1 | KASHDIDRYIA | 5G9.VL.1 |
| 144 | 5G9.VL.1 CDR-L2 | YTSTLQP | |
| 145 | 5G9.VL.1 CDR-L3 | LNYDNLLWT | |
| 146 | 5G9.VL.2 CDR-L1 | KASHDIDRYIA | 5G9.VL.2 |
| 147 | 5G9.VL.2 CDR-L2 | YTSTLQP | |
| 148 | 5G9.VL.2 CDR-L3 | LNYDNLLWT | |
| 149 | 5G9.VL.3 CDR-L1 | KASHDIDRYIA | 5G9.VL.3 |
| 150 | 5G9.VL.3 CDR-L2 | YTSTLQP | |
| 151 | 5G9.VL.3 CDR-L3 | LNYDNLLWT | |
| 152 | 5G9.VL.4 CDR-L1 | KASHDIDRYIA | 5G9.VL.4 |
| 153 | 5G9.VL.4 CDR-L2 | YTSTLQP | |
| 154 | 5G9.VL.4 CDR-L3 | LNYDNLLWT | |
| 155 | 5G9.VL.5 CDR-L1 | KASHDIDRYIA | 5G9.VL.5 |
| 156 | 5G9.VL.5 CDR-L2 | YTSTLQP | |
| 157 | 5G9.VL.5 CDR-L3 | LNYDNLLWT | |
| 158 | 5G9.VL.6 CDR-L1 | KASHDIDRYIA | 5G9.VL.6 |
| 159 | 5G9.VL.6 CDR-L2 | YTSTLQP | |
| 160 | 5G9.VL.6 CDR-L3 | LNYDNLLWT | |

I claim:

1. An isolated antibody or an antigen binding portion thereof that specifically binds Receptor tyrosine-protein kinase ErbB-2 (ErbB2), comprising a heavy chain variable region which comprises CDR-H1, CDR-H2, CDR-H3, and a light chain variable region which comprises CDR-L1, CDR-L2 and CDR-L3, wherein the CDR-H1, CDR-H2, CDR-H3, CDR-L1, CDR-L2 and CDR-L3 comprise amino acid sequences of:
   a) SEQ ID NOs: 80, 81, 82, 83, 84 and 85, respectively;
   b) SEQ ID NOs: 74, 75, 76, 77, 78 and 79, respectively;
   c) SEQ ID NOs: 56, 57, 58, 59, 60 and 61, respectively;
   d) SEQ ID NOs: 62, 63, 64, 65, 66 and 67, respectively; or
   e) SEQ ID NOs: 68, 69, 70, 71, 72 and 73, respectively.

2. The isolated antibody or antigen binding portion thereof of claim 1, wherein the heavy chain variable region and the light chain variable region respectively comprise amino acid sequences having at least 95% sequence identity to SEQ ID NOs: 17 and 18; SEQ ID NOs: 19 and 20; SEQ ID NOs: 21 and 22; SEQ ID NOs: 23 and 24; SEQ ID NOs: 25 and 26; SEQ ID NOs: 27 and 32; SEQ ID NOs: 27 and 33; SEQ ID NOs: 27 and 34; SEQ ID NOs: 27 and 35; SEQ ID NOs: 27 and 36; SEQ ID NOs: 27 and 37; SEQ ID NOs: 27 and 38; SEQ ID NOs: 28 and 32; SEQ ID NOs: 28 and 33; SEQ ID NOs: 28 and 34; SEQ ID NOs: 28 and 35; SEQ ID NOs: 28 and 36; SEQ ID NOs: 28 and 37; SEQ ID NOs: 28 and 38; SEQ ID NOs: 29 and 32; SEQ ID NOs: 29 and 33; SEQ ID NOs: 29 and 34; SEQ ID NOs: 29 and 35; SEQ ID NOs: 29 and 36; SEQ ID NOs: 29 and 37; SEQ ID NOs: 29 and 38; SEQ ID NOs: 30 and 32; SEQ ID NOs: 30 and 33; SEQ ID NOs: 30 and 34; SEQ ID NOs: 30 and 35; SEQ ID NOs: 30 and 36; SEQ ID NOs: 30 and 37; SEQ ID NOs: 30 and 38; SEQ ID NOs: 31 and 32; SEQ ID NOs: 31 and 33; SEQ ID NOs: 31 and 34; SEQ ID NOs: 31 and 35; SEQ ID NOs: 31 and 36; SEQ ID NOs: 31 and 37; SEQ ID NOs: 31 and 38; SEQ ID NOs: 39 and 45; SEQ ID NOs: 39 and 46; SEQ ID NOs: 39 and 47; SEQ ID NOs: 39 and 48; SEQ ID NOs: 39 and 49; SEQ ID NOs: 39 and 50; SEQ ID NOs: 39 and 51; SEQ ID NOs: 40 and 45; SEQ ID NOs: 40 and 46; SEQ ID NOs: 40 and 47; SEQ ID NOs: 40 and 48; SEQ ID NOs: 40 and 49; SEQ ID NOs: 40 and 50; SEQ ID NOs: 40 and 51; SEQ ID NOs: 41 and 45; SEQ ID NOs: 41 and 46; SEQ ID NOs: 41 and 47; SEQ ID NOs: 41 and 48; SEQ ID NOs: 41 and 49; SEQ ID NOs: 41 and 50; SEQ ID NOs: 41 and 51; SEQ ID NOs: 42 and 45; SEQ ID NOs: 42 and 46; SEQ ID NOs: 42 and 47; SEQ ID NOs: 42 and 48; SEQ ID NOs: 42 and 49; SEQ ID NOs: 42 and 50; SEQ ID NOs: 42 and 51; SEQ ID NOs: 43 and 45; SEQ ID NOs: 43 and 46; SEQ ID NOs: 43 and 47; SEQ ID NOs: 43 and 48; SEQ ID NOs: 43 and 49; SEQ ID NOs: 43 and 50; SEQ ID NOs: 43 and 51; SEQ ID NOs: 44 and 45; SEQ ID NOs: 44 and 46; SEQ ID NOs: 44 and 47; SEQ ID NOs: 44 and 48; SEQ ID NOs: 44 and 49; SEQ ID NOs: 44 and 50; or SEQ ID NOs: 44 and 51.

3. The isolated antibody or antigen binding portion thereof of claim 1, wherein the heavy chain variable region comprises an amino acid sequence having at least 95% sequence identity to any one of SEQ ID NOs: 17, 19, 21, 23, 25, 27, 28, 29, 30, 31, 39, 40, 41, 42, 43, or 44.

4. The isolated antibody or antigen binding portion thereof of claim 1, wherein the light chain variable region comprises an amino acid sequence having at least 95% sequence identity to any one of SEQ ID NOs:18, 20, 22, 24, 26, 32, 33, 34, 35, 36, 37, 38, 45, 46, 47, 48, 49, 50 or 51.

5. A binding protein conjugate comprising the isolated antibody or antigen binding portion thereof of claim 1, a linker polypeptide or an immunoglobulin constant domain, and an agent, wherein the agent is selected from the group consisting of an imaging agent, a therapeutic agent, a cytotoxic agent, and an immunoadhesion molecule.

6. A pharmaceutical composition comprising the isolated antibody or antigen binding portion thereof of claim 1 and a pharmaceutically acceptable carrier.

7. A method for treating a disease or disorder in a subject, wherein ErbB2 activity is detrimental in the disease or disorder, comprising administering to the subject an effective amount of the isolated antibody or antigen binding portion thereof of claim 1, whereby the ErbB2 activity is modulated in the subject.

8. The method of claim 7, wherein the disease or disorder is selected from the group consisting of breast cancer, gastric cancer, colon cancer, rectal cancer, lung cancer, oropharynx cancer, hypopharynx cancer, esophageal cancer, stomach cancer, pancreas cancer, liver cancer, gallbladder cancer, bile duct cancer, small intestine cancer, urinary tract cancer, female genital tract cancer, male genital tract cancer, endocrine gland cancer, skin cancer, hemangioma, melanoma, sarcoma, brain tumor, nerve cancer, eye tumor, meninges cancer, solid tumors from hematopoietic malignancy, tumor metastases, ocular neovascularization, edema, rheumatoid arthritis, atherosclerotic plaques, Crohn's disease, inflammatory bowel disease, refractory ascites, psoriasis, sarcoidosis, arterial arteriosclerosis, sepsis, peptic ulcers, burns, pancreatitis, polycystic ovarian disease (POD), endometriosis, uterine fibroid, benign prostate hypertrophy, T-cell acute lymphoblastic leukemia (T-ALL), cerebral autosomal dominant arteriopathy with subcortical infarcts and leukoencephalopathy (CADA-SIL), multiple sclerosis (MS), tetralogy of Fallot (TOF), Alagille syndrome (AS), macular degeneration and age-related macular degeneration diseases, and other angiogenesis independent and dependent diseases characterized by aberrant ErbB2 activity.

9. The method of claim 7, wherein the disease or disorder is a primary and metastatic cancer.

10. The method of claim 7, wherein the disease or disorder is an ErbB2-positive tumor, further comprising inhibiting growth of the tumor in the subject.

11. The method of claim 7, further comprising administering to the subject one or more additional agents, wherein each of the one or more additional agents is an antibody or antigen binding fragment thereof capable of binding ErbB2, and wherein each of the one or more additional agents is different from the binding protein.

12. The method of claim 11, wherein the one or more additional agents comprise Trastuzumab, Pertuzumab or a combination thereof.

13. The method of claim 11, further comprising modulating the ErbB2 activity in the subject synergistically with the one or more additional agents.

14. A method for inhibiting growth of ErbB2-positive cells, comprising contacting the cells with an effective amount of the isolated antibody or antigen binding portion thereof of claim 1.

15. The method of claim 14, further comprising contacting the cells with one or more additional agents, and inhibiting the growth of the ErbB2-positive cells with the one or more additional agents synergistically, wherein each of the one or more additional agents is an antibody or antigen binding fragment thereof capable of binding ErbB2, and wherein each of the one or more additional agents is different from the binding protein.

16. The method of claim 15, wherein the one or more additional agents comprise Trastuzumab, Pertuzumab or a combination thereof.

17. The method of claim 14, wherein the cells are in a subject.

18. The method of claim 17, wherein the subject suffers from a disease or disorder in which ErbB2 activity is detrimental.

* * * * *

SEQUENCE LISTING

<160> NUMBER OF SEQ ID NOS: 166

<210> SEQ ID NO 1
<211> LENGTH: 330
<212> TYPE: PRT
<213> ORGANISM: Homo sapiens

<400> SEQUENCE: 1

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 107
<212> TYPE: PRT
<213> ORGANISM: Homo sapiens

<400> SEQUENCE: 2

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 3
<211> LENGTH: 30
<212> TYPE: PRT
<213> ORGANISM: Homo sapiens

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 4
<211> LENGTH: 14
<212> TYPE: PRT
<213> ORGANISM: Homo sapiens

<400> SEQUENCE: 4

Trp Val Arg Gln Ala Pro Gly Gln Gly Leu Glu Trp Met Gly
1               5                   10

<210> SEQ ID NO 5
<211> LENGTH: 32
<212> TYPE: PRT
<213> ORGANISM: Homo sapiens

<400> SEQUENCE: 5

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 6
<211> LENGTH: 11
<212> TYPE: PRT
<213> ORGANISM: Homo sapiens

<400> SEQUENCE: 6

Trp Gly Gln Gly Thr Leu Val Thr Val Ser Ser
1               5                   10

<210> SEQ ID NO 7
<211> LENGTH: 23
<212> TYPE: PRT
<213> ORGANISM: Homo sapiens

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 8
<211> LENGTH: 15
<212> TYPE: PRT
<213> ORGANISM: Homo sapiens

<400> SEQUENCE: 8

Trp Tyr Gln Gln Lys Pro Gly Lys Gly Pro Lys Leu Leu Ile Tyr
1               5                   10                  15

<210> SEQ ID NO 9
<211> LENGTH: 32

<212> TYPE: PRT
<213> ORGANISM: Homo sapiens

<400> SEQUENCE: 9

Gly Val Pro Ser Arg Phe Ser Gly Ser Gly Thr Asp Phe Thr
1               5                   10                  15
Leu Thr Ile Ser Ser Leu Gln Pro Glu Asp Phe Ala Thr Tyr Tyr Cys
            20                  25                  30

<210> SEQ ID NO 10
<211> LENGTH: 10
<212> TYPE: PRT
<213> ORGANISM: Homo sapiens

<400> SEQUENCE: 10

Phe Gly Gln Gly Thr Lys Val Glu Ile Lys
1               5                   10

<210> SEQ ID NO 11
<211> LENGTH: 5
<212> TYPE: PRT
<213> ORGANISM: Artificial Sequence
<220> FEATURE:
<223> OTHER INFORMATION: CDR-H1
<220> FEATURE:
<221> NAME/KEY: misc_feature
<222> LOCATION: (1)..(1)
<223> OTHER INFORMATION: Xaa can be Ser
<220> FEATURE:
<221> NAME/KEY: misc_feature
<222> LOCATION: (2)..(2)
<223> OTHER INFORMATION: Xaa can be Tyr
<220> FEATURE:
<221> NAME/KEY: misc_feature
<222> LOCATION: (3)..(3)
<223> OTHER INFORMATION: Xaa can be Thr or Tyr
<220> FEATURE:
<221> NAME/KEY: misc_feature
<222> LOCATION: (4)..(4)
<223> OTHER INFORMATION: Xaa can be Met or Ile
<220> FEATURE:
<221> NAME/KEY: misc_feature
<222> LOCATION: (5)..(5)
<223> OTHER INFORMATION: Xaa can be His

<400> SEQUENCE: 11

Xaa Xaa Xaa Xaa Xaa
1               5

<210> SEQ ID NO 12
<211> LENGTH: 17
<212> TYPE: PRT
<213> ORGANISM: Artificial Sequence
<220> FEATURE:
<223> OTHER INFORMATION: CDR-H2
<220> FEATURE:
<221> NAME/KEY: misc_feature
<222> LOCATION: (1)..(1)
<223> OTHER INFORMATION: Xaa can be Thr
<220> FEATURE:
<221> NAME/KEY: misc_feature
<222> LOCATION: (2)..(2)
<223> OTHER INFORMATION: Xaa can be Ile
<220> FEATURE:
<221> NAME/KEY: misc_feature
<222> LOCATION: (3)..(3)
<223> OTHER INFORMATION: Xaa can be Asn
<220> FEATURE:
<221> NAME/KEY: misc_feature
<222> LOCATION: (4)..(4)
<223> OTHER INFORMATION: Xaa can be Pro
<220> FEATURE:

```
<221> NAME/KEY: misc_feature
<222> LOCATION: (5)..(5)
<223> OTHER INFORMATION: Xaa can be Ser
<220> FEATURE:
<221> NAME/KEY: misc_feature
<222> LOCATION: (6)..(6)
<223> OTHER INFORMATION: Xaa can be Ser
<220> FEATURE:
<221> NAME/KEY: misc_feature
<222> LOCATION: (7)..(7)
<223> OTHER INFORMATION: Xaa can be Ser or Asp
<220> FEATURE:
<221> NAME/KEY: misc_feature
<222> LOCATION: (8)..(8)
<223> OTHER INFORMATION: Xaa can be Tyr
<220> FEATURE:
<221> NAME/KEY: misc_feature
<222> LOCATION: (9)..(9)
<223> OTHER INFORMATION: Xaa can be Thr
<220> FEATURE:
<221> NAME/KEY: misc_feature
<222> LOCATION: (10)..(10)
<223> OTHER INFORMATION: Xaa can be Ala or Asn
<220> FEATURE:
<221> NAME/KEY: misc_feature
<222> LOCATION: (11)..(11)
<223> OTHER INFORMATION: Xaa can be Tyr
<220> FEATURE:
<221> NAME/KEY: misc_feature
<222> LOCATION: (12)..(12)
<223> OTHER INFORMATION: Xaa can be Asn
<220> FEATURE:
<221> NAME/KEY: misc_feature
<222> LOCATION: (13)..(13)
<223> OTHER INFORMATION: Xaa can be Gln
<220> FEATURE:
<221> NAME/KEY: misc_feature
<222> LOCATION: (14)..(14)
<223> OTHER INFORMATION: Xaa can be Lys or Asn
<220> FEATURE:
<221> NAME/KEY: misc_feature
<222> LOCATION: (15)..(15)
<223> OTHER INFORMATION: Xaa can be Phe
<220> FEATURE:
<221> NAME/KEY: misc_feature
<222> LOCATION: (16)..(16)
<223> OTHER INFORMATION: Xaa can be Lys or Arg
<220> FEATURE:
<221> NAME/KEY: misc_feature
<222> LOCATION: (17)..(17)
<223> OTHER INFORMATION: Xaa can be Asp

<400> SEQUENCE: 12

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 13
<211> LENGTH: 9
<212> TYPE: PRT
<213> ORGANISM: Artificial Sequence
<220> FEATURE:
<223> OTHER INFORMATION: CDR-H3
<220> FEATURE:
<221> NAME/KEY: misc_feature
<222> LOCATION: (1)..(1)
<223> OTHER INFORMATION: Xaa can be Ala
<220> FEATURE:
<221> NAME/KEY: misc_feature
<222> LOCATION: (2)..(2)
<223> OTHER INFORMATION: Xaa can be Ser
<220> FEATURE:
<221> NAME/KEY: misc_feature
<222> LOCATION: (3)..(3)
<223> OTHER INFORMATION: Xaa can be Ala or Ser
<220> FEATURE:
```

```
<221> NAME/KEY: misc_feature
<222> LOCATION: (4)..(4)
<223> OTHER INFORMATION: Xaa can be Phe
<220> FEATURE:
<221> NAME/KEY: misc_feature
<222> LOCATION: (5)..(5)
<223> OTHER INFORMATION: Xaa can be Ser
<220> FEATURE:
<221> NAME/KEY: misc_feature
<222> LOCATION: (6)..(6)
<223> OTHER INFORMATION: Xaa can be Leu
<220> FEATURE:
<221> NAME/KEY: misc_feature
<222> LOCATION: (7)..(7)
<223> OTHER INFORMATION: Xaa can be Asp
<220> FEATURE:
<221> NAME/KEY: misc_feature
<222> LOCATION: (8)..(8)
<223> OTHER INFORMATION: Xaa can be Phe
<220> FEATURE:
<221> NAME/KEY: misc_feature
<222> LOCATION: (9)..(9)
<223> OTHER INFORMATION: Xaa can be Trp

<400> SEQUENCE: 13

Xaa Xaa Xaa Xaa Xaa Xaa Xaa Xaa Xaa
1               5

<210> SEQ ID NO 14
<211> LENGTH: 11
<212> TYPE: PRT
<213> ORGANISM: Artificial Sequence
<220> FEATURE:
<223> OTHER INFORMATION: CDR-L1
<220> FEATURE:
<221> NAME/KEY: misc_feature
<222> LOCATION: (1)..(1)
<223> OTHER INFORMATION: Xaa can be Lys
<220> FEATURE:
<221> NAME/KEY: misc_feature
<222> LOCATION: (2)..(2)
<223> OTHER INFORMATION: Xaa can be Ala
<220> FEATURE:
<221> NAME/KEY: misc_feature
<222> LOCATION: (3)..(3)
<223> OTHER INFORMATION: Xaa can be Ser
<220> FEATURE:
<221> NAME/KEY: misc_feature
<222> LOCATION: (4)..(4)
<223> OTHER INFORMATION: Xaa can be His or Gln
<220> FEATURE:
<221> NAME/KEY: misc_feature
<222> LOCATION: (5)..(5)
<223> OTHER INFORMATION: Xaa can be Asp
<220> FEATURE:
<221> NAME/KEY: misc_feature
<222> LOCATION: (6)..(6)
<223> OTHER INFORMATION: Xaa can be Ile
<220> FEATURE:
<221> NAME/KEY: misc_feature
<222> LOCATION: (7)..(7)
<223> OTHER INFORMATION: Xaa can be Asn
<220> FEATURE:
<221> NAME/KEY: misc_feature
<222> LOCATION: (8)..(8)
<223> OTHER INFORMATION: Xaa can be Lys
<220> FEATURE:
<221> NAME/KEY: misc_feature
<222> LOCATION: (9)..(9)
<223> OTHER INFORMATION: Xaa can be Tyr
<220> FEATURE:
<221> NAME/KEY: misc_feature
<222> LOCATION: (10)..(10)
<223> OTHER INFORMATION: Xaa can be Ile
<220> FEATURE:
<221> NAME/KEY: misc_feature
<222> LOCATION: (11)..(11)
```

<223> OTHER INFORMATION: Xaa can be Ala

<400> SEQUENCE: 14

Xaa Xaa Xaa Xaa Xaa Xaa Xaa Xaa Xaa Xaa
1               5                   10

<210> SEQ ID NO 15
<211> LENGTH: 7
<212> TYPE: PRT
<213> ORGANISM: Artificial Sequence
<220> FEATURE:
<223> OTHER INFORMATION: CDR-L2
<220> FEATURE:
<221> NAME/KEY: misc_feature
<222> LOCATION: (1)..(1)
<223> OTHER INFORMATION: Xaa can be Thr or Ser
<220> FEATURE:
<221> NAME/KEY: misc_feature
<222> LOCATION: (2)..(2)
<223> OTHER INFORMATION: Xaa can be Thr
<220> FEATURE:
<221> NAME/KEY: misc_feature
<222> LOCATION: (3)..(3)
<223> OTHER INFORMATION: Xaa can be Ser
<220> FEATURE:
<221> NAME/KEY: misc_feature
<222> LOCATION: (4)..(4)
<223> OTHER INFORMATION: Xaa can be Thr
<220> FEATURE:
<221> NAME/KEY: misc_feature
<222> LOCATION: (5)..(5)
<223> OTHER INFORMATION: Xaa can be Leu
<220> FEATURE:
<221> NAME/KEY: misc_feature
<222> LOCATION: (6)..(6)
<223> OTHER INFORMATION: Xaa can be Gln or Tyr
<220> FEATURE:
<221> NAME/KEY: misc_feature
<222> LOCATION: (7)..(7)
<223> OTHER INFORMATION: Xaa can be Pro

<400> SEQUENCE: 15

Xaa Xaa Xaa Xaa Xaa Xaa Xaa
1               5

<210> SEQ ID NO 16
<211> LENGTH: 9
<212> TYPE: PRT
<213> ORGANISM: Artificial Sequence
<220> FEATURE:
<223> OTHER INFORMATION: CDR-L3
<220> FEATURE:
<221> NAME/KEY: misc_feature
<222> LOCATION: (1)..(1)
<223> OTHER INFORMATION: Xaa can be Leu
<220> FEATURE:
<221> NAME/KEY: misc_feature
<222> LOCATION: (2)..(2)
<223> OTHER INFORMATION: Xaa can be Gln or Asn
<220> FEATURE:
<221> NAME/KEY: misc_feature
<222> LOCATION: (3)..(3)
<223> OTHER INFORMATION: Xaa can be Tyr
<220> FEATURE:
<221> NAME/KEY: misc_feature
<222> LOCATION: (4)..(4)
<223> OTHER INFORMATION: Xaa can be Asp
<220> FEATURE:
<221> NAME/KEY: misc_feature
<222> LOCATION: (5)..(5)
<223> OTHER INFORMATION: Xaa can be Asn
<220> FEATURE:
<221> NAME/KEY: misc_feature
<222> LOCATION: (6)..(6)
<223> OTHER INFORMATION: Xaa can be Leu
<220> FEATURE:
<221> NAME/KEY: misc_feature
<222> LOCATION: (7)..(7)
<223> OTHER INFORMATION: Xaa can be Leu
<220> FEATURE:
<221> NAME/KEY: misc_feature
<222> LOCATION: (8)..(8)
<223> OTHER INFORMATION: Xaa can be Trp
<220> FEATURE:
<221> NAME/KEY: misc_feature
<222> LOCATION: (9)..(9)
<223> OTHER INFORMATION: Xaa can be Thr

<400> SEQUENCE: 16

Xaa Xaa Xaa Xaa Xaa Xaa Xaa Xaa Xaa
1               5

<210> SEQ ID NO 17
<211> LENGTH: 117
<212> TYPE: PRT
<213> ORGANISM: Mus musculus

<400> SEQUENCE: 17

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
                20                  25                  30

Thr Met His Trp Val Lys Gln Arg Pro Gly Gln Gly Leu Asp Trp Ile
            35                  40                  45

Gly Tyr Ile Asn Pro Ser Ser Gly Tyr Thr Tyr Asn Gln Lys Phe
        50                  55                  60

Lys Asp Lys Ala Thr Leu Thr Ala Asp Lys Ser Ser Thr Ala Tyr
65                  70                  75                  80

Met Gln Leu Ser Ser Leu Ala Ser Ala Asp Ser Ala Val Tyr Tyr Cys
                85                  90                  95

Ala Arg Ala Ser Ala Tyr Ser Leu Asp Tyr Trp Gly Gln Gly Thr Thr
            100                 105                 110

Leu Thr Val Ser Ser
        115

<210> SEQ ID NO 18
<211> LENGTH: 107
<212> TYPE: PRT
<213> ORGANISM: Mus musculus

<400> SEQUENCE: 18

Asp Ile Gln Met Thr Gln Ser Pro Ser Ser Leu Ser Ala Ser Leu Gly
1               5                   10                  15

Gly Arg Val Thr Ile Thr Cys Lys Ala Ser His Asp Ile Asp Arg Tyr
                20                  25                  30

Ile Ala Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
        50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Lys Tyr Asp Asn Leu Leu Trp
                85                  90                  95

Thr Phe Gly Gly Gly Thr Lys Leu Glu Ile Thr
            100                 105

<210> SEQ ID NO 19
<211> LENGTH: 117
<212> TYPE: PRT
<213> ORGANISM: Mus musculus

<400> SEQUENCE: 19

Gln Val Gln Leu Gln Gln Ser Gly Ala Glu Leu Ala Arg Pro Gly Ala
1               5                   10                  15

Ser Val Lys Met Ser Cys Lys Ala Ser Gly Phe Thr Phe Thr Ser Tyr
            20                  25                  30

Thr Ile His Trp Val Lys Gln Arg Pro Gly Gln Gly Leu Asp Trp Ile
        35                  40                  45

Gly Tyr Ile Asn Pro Ser Ser Gly Tyr Thr Thr Tyr Asn Gln Arg Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Ala Asp Ser Ala Val Tyr Tyr Cys
                85                  90                  95

Ala Arg Ala Ser Ala Tyr Ser Leu Asp Tyr Trp Gly Gln Gly Thr Thr
            100                 105                 110

Leu Thr Val Ser Ser
        115

<210> SEQ ID NO 20
<211> LENGTH: 107
<212> TYPE: PRT
<213> ORGANISM: Mus musculus

<400> SEQUENCE: 20

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asp Arg Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asn Tyr Ser Phe Ser Ile Ser Asn Leu Glu Pro
65                  70                  75                  80

Glu Asp Ile Ala Thr Tyr Tyr Cys Leu Lys Tyr Asp Asn Leu Leu Trp
                85                  90                  95

Thr Phe Gly Gly Gly Thr Lys Leu Glu Ile Lys
            100                 105

<210> SEQ ID NO 21
<211> LENGTH: 117
<212> TYPE: PRT
<213> ORGANISM: Mus musculus

<400> SEQUENCE: 21

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Ala Tyr Thr Asn Tyr Asn Gln Lys Phe

Lys Asp Lys Ala Thr Leu Thr Ala Asp Lys Ser Ser Ser Thr Ala Asn
65                  70                  75                  80

Met Gln Leu Asn Ser Leu Thr Ser Glu Asp Ser Ala Val Tyr Tyr Cys
                85                  90                  95

Ala Arg Ala Ser Ala Tyr Ser Leu Asp Tyr Trp Gly Gln Gly Thr Ala
                100                 105                 110

Leu Thr Val Ser Ser
        115

<210> SEQ ID NO 22
<211> LENGTH: 107
<212> TYPE: PRT
<213> ORGANISM: Mus musculus

<400> SEQUENCE: 22

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
                20                  25                  30

Ile Ala Trp Tyr Gln His Lys Pro Gly Lys Pro Arg Leu Leu Ile
                35                  40                  45

His Ser Thr Ser Thr Leu Tyr Pro Gly Ile Pro Ser Arg Phe Ser Gly
        50                  55                  60

Ser Gly Ser Gly Arg Asp Tyr Ser Phe Arg Ile Thr Asn Leu Glu Pro
65                  70                  75                  80

Glu Asp Ile Ala Thr Tyr Tyr Cys Leu Gln Tyr Asp Asn Leu Leu Trp
                85                  90                  95

Thr Phe Gly Gly Gly Thr Lys Val Gly Ile Arg
                100                 105

<210> SEQ ID NO 23
<211> LENGTH: 117
<212> TYPE: PRT
<213> ORGANISM: Mus musculus

<400> SEQUENCE: 23

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
                20                  25                  30

Thr Met His Trp Ile Lys Gln Arg Pro Gly Gln Gly Leu Glu Trp Ile
                35                  40                  45

Gly Tyr Ile Asn Pro Ser Ser Ser Tyr Thr Asn Tyr Asn Gln Asn Phe
        50                  55                  60

Lys Asp Lys Ala Thr Leu Thr Ala Asp Lys Ser Ser Ser Thr Ala Asn
65                  70                  75                  80

Met Gln Leu Asn Ser Leu Thr Ser Glu Asp Ser Ala Val Tyr Tyr Cys
                85                  90                  95

Ala Arg Ala Ser Ser Tyr Ser Leu Asp Tyr Trp Gly Gln Gly Thr Ala
                100                 105                 110

Leu Thr Val Ser Ser
        115

<210> SEQ ID NO 24
<211> LENGTH: 107
<212> TYPE: PRT

<213> ORGANISM: Mus musculus

<400> SEQUENCE: 24

Asp Ile Gln Met Thr Gln Ser Pro Ser Ser Leu Ser Thr Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Ser Thr Ser Thr Leu Tyr Pro Gly Ile Pro Ser Arg Phe Ser Gly
    50                  55                  60

Ser Gly Ser Gly Lys Asp Tyr Ser Phe Arg Ile Thr Asn Leu Glu Pro
65                  70                  75                  80

Glu Asp Ile Ala Thr Tyr Tyr Cys Leu Gln Tyr Asp Asn Leu Leu Trp
                85                  90                  95

Thr Phe Gly Gly Gly Thr Lys Leu Gly Ile Arg
            100                 105

<210> SEQ ID NO 25
<211> LENGTH: 117
<212> TYPE: PRT
<213> ORGANISM: Mus musculus

<400> SEQUENCE: 25

Gln Val Gln Leu Gln Gln Ser Gly Ala Glu Leu Ala Arg Pro Gly Ala
1               5                   10                  15

Ser Val Lys Met Ser Cys Lys Thr Ser Gly Tyr Thr Phe Ser Ser Tyr
            20                  25                  30

Thr Ile His Trp Val Lys Gln Arg Pro Gly Gln Gly Leu Asp Trp Ile
        35                  40                  45

Gly Tyr Ile Asn Pro Ser Ser Asp Tyr Thr Ala Tyr Asn Gln Lys Phe
    50                  55                  60

Arg Asp Lys Ala Thr Leu Thr Ala Asp Gln Ser Ser Asn Thr Ala Tyr
65                  70                  75                  80

Met Gln Leu Ser Ser Leu Ala Ser Ala Asp Ser Ala Val Tyr Tyr Cys
                85                  90                  95

Ala Arg Ala Ser Ala Phe Ser Leu Asp Phe Trp Gly Gln Gly Thr Thr
            100                 105                 110

Leu Thr Val Ser Ser
        115

<210> SEQ ID NO 26
<211> LENGTH: 107
<212> TYPE: PRT
<213> ORGANISM: Mus musculus

<400> SEQUENCE: 26

Asp Ile Gln Met Thr Gln Ser Pro Ser Ser Leu Ser Ala Ser Leu Gly
1               5                   10                  15

Gly Lys Val Thr Ile Ser Cys Lys Ala Ser His Asp Ile Asp Arg Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Val Ala Thr Tyr Tyr Cys Leu Asn Tyr Asp Asn Leu Leu Trp
                85                  90                  95

Thr Phe Gly Gly Gly Thr Lys Leu Glu Ile Thr
            100                 105

<210> SEQ ID NO 27
<211> LENGTH: 117
<212> TYPE: PRT
<213> ORGANISM: Artificial Sequence
<220> FEATURE:
<223> OTHER INFORMATION: 5F12.VH.V1

<400> SEQUENCE: 27

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Thr Met His Trp Ile Arg Gln Ala Pro Gly Gln Gly Leu Glu Trp Ile
            35                  40                  45

Gly Tyr Ile Asn Pro Ser Ser Ser Tyr Thr Asn Tyr Asn Gln Asn Phe
    50                  55                  60

Lys Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Ser Tyr Ser Leu Asp Tyr Trp Gly Gln Gly Thr Leu
            100                 105                 110

Val Thr Val Ser Ser
        115

<210> SEQ ID NO 28
<211> LENGTH: 117
<212> TYPE: PRT
<213> ORGANISM: Artificial Sequence
<220> FEATURE:
<223> OTHER INFORMATION: 5F12.VH.1

<400> SEQUENCE: 28

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Thr Met His Trp Val Arg Gln Ala Pro Gly Gln Gly Leu Glu Trp Ile
            35                  40                  45

Gly Tyr Ile Asn Pro Ser Ser Ser Tyr Thr Asn Tyr Asn Gln Asn Phe
    50                  55                  60

Lys Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Ser Tyr Ser Leu Asp Tyr Trp Gly Gln Gly Thr Leu
            100                 105                 110

Val Thr Val Ser Ser
        115

<210> SEQ ID NO 29
<211> LENGTH: 117
<212> TYPE: PRT

```
<213> ORGANISM: Artificial Sequence
<220> FEATURE:
<223> OTHER INFORMATION: 5F12.VH.2

<400> SEQUENCE: 29

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Thr Met His Trp Ile Arg Gln Ala Pro Gly Gln Gly Leu Glu Trp Met
            35                  40                  45

Gly Tyr Ile Asn Pro Ser Ser Ser Tyr Thr Asn Tyr Asn Gln Asn Phe
    50                  55                      60

Lys Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Ser Tyr Ser Leu Asp Tyr Trp Gly Gln Gly Thr Leu
                100                 105                 110

Val Thr Val Ser Ser
        115

<210> SEQ ID NO 30
<211> LENGTH: 117
<212> TYPE: PRT
<213> ORGANISM: Artificial Sequence
<220> FEATURE:
<223> OTHER INFORMATION: 5F12.VH.3

<400> SEQUENCE: 30

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Thr Met His Trp Ile Arg Gln Ala Pro Gly Gln Gly Leu Glu Trp Ile
            35                  40                  45

Gly Tyr Ile Asn Pro Ser Ser Ser Tyr Thr Asn Tyr Asn Gln Asn Phe
    50                  55                      60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Ser Tyr Ser Leu Asp Tyr Trp Gly Gln Gly Thr Leu
                100                 105                 110

Val Thr Val Ser Ser
        115

<210> SEQ ID NO 31
<211> LENGTH: 117
<212> TYPE: PRT
<213> ORGANISM: Artificial Sequence
<220> FEATURE:
<223> OTHER INFORMATION: 5F12.VH.4

<400> SEQUENCE: 31

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30
```

```
Thr Met His Trp Ile Arg Gln Ala Pro Gly Gln Gly Leu Glu Trp Ile
        35                  40                  45

Gly Tyr Ile Asn Pro Ser Ser Ser Tyr Thr Asn Tyr Asn Gln Asn Phe
 50                  55                  60

Lys Asp Arg Ala Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Ser Ser Tyr Ser Leu Asp Tyr Trp Gly Gln Gly Thr Leu
                100                 105                 110

Val Thr Val Ser Ser
        115

<210> SEQ ID NO 32
<211> LENGTH: 107
<212> TYPE: PRT
<213> ORGANISM: Artificial Sequence
<220> FEATURE:
<223> OTHER INFORMATION: 5F12.VL.V1

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
                20                  25                  30

Ile Ala Trp Tyr Gln His Lys Pro Gly Lys Gly Pro Lys Leu Leu Ile
            35                  40                  45

His Ser Thr Ser Thr Leu Tyr Pro Gly Ile Pro Ser Arg Phe Ser Gly
 50                  55                  60

Ser Gly Ser Gly Lys Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Leu Trp
                85                  90                  95

Thr Phe Gly Gln Gly Thr Lys Val Glu Ile Lys
                100                 105

<210> SEQ ID NO 33
<211> LENGTH: 107
<212> TYPE: PRT
<213> ORGANISM: Artificial Sequence
<220> FEATURE:
<223> OTHER INFORMATION: 5F12.VL.1

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
                20                  25                  30

Ile Ala Trp Tyr Gln Gln Lys Pro Gly Lys Gly Pro Lys Leu Leu Ile
            35                  40                  45

His Ser Thr Ser Thr Leu Tyr Pro Gly Ile Pro Ser Arg Phe Ser Gly
 50                  55                  60

Ser Gly Ser Gly Lys Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Leu Trp
                85                  90                  95

Thr Phe Gly Gln Gly Thr Lys Val Glu Ile Lys
```

<210> SEQ ID NO 34
<211> LENGTH: 107
<212> TYPE: PRT
<213> ORGANISM: Artificial Sequence
<220> FEATURE:
<223> OTHER INFORMATION: 5F12.VL.2

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Ile Ala Trp Tyr Gln His Lys Pro Gly Lys Ala Pro Lys Leu Leu Ile
        35                  40                  45

His Ser Thr Ser Thr Leu Tyr Pro Gly Ile Pro Ser Arg Phe Ser Gly
    50                  55                  60

Ser Gly Ser Gly Lys Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Leu Trp
                85                  90                  95

Thr Phe Gly Gln Gly Thr Lys Val Glu Ile Lys
            100                 105

<210> SEQ ID NO 35
<211> LENGTH: 107
<212> TYPE: PRT
<213> ORGANISM: Artificial Sequence
<220> FEATURE:
<223> OTHER INFORMATION: 5F12.VL.3

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Ile Ala Trp Tyr Gln His Lys Pro Gly Lys Gly Pro Lys Leu Leu Ile
        35                  40                  45

Tyr Ser Thr Ser Thr Leu Tyr Pro Gly Ile Pro Ser Arg Phe Ser Gly
    50                  55                  60

Ser Gly Ser Gly Lys Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Leu Trp
                85                  90                  95

Thr Phe Gly Gln Gly Thr Lys Val Glu Ile Lys
            100                 105

<210> SEQ ID NO 36
<211> LENGTH: 107
<212> TYPE: PRT
<213> ORGANISM: Artificial Sequence
<220> FEATURE:
<223> OTHER INFORMATION: 5F12.VL.4

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Ile Ala Trp Tyr Gln His Lys Pro Gly Lys Gly Pro Lys Leu Leu Ile
            35                  40                  45

His Ser Thr Ser Thr Leu Tyr Pro Gly Val Pro Ser Arg Phe Ser Gly
        50                  55                  60

Ser Gly Ser Gly Lys Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Leu Trp
                85                  90                  95

Thr Phe Gly Gln Gly Thr Lys Val Glu Ile Lys
                100                 105

<210> SEQ ID NO 37
<211> LENGTH: 107
<212> TYPE: PRT
<213> ORGANISM: Artificial Sequence
<220> FEATURE:
<223> OTHER INFORMATION: 5F12.VL.5

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
                20                  25                  30

Ile Ala Trp Tyr Gln His Lys Pro Gly Lys Gly Pro Lys Leu Leu Ile
            35                  40                  45

His Ser Thr Ser Thr Leu Tyr Pro Gly Ile Pro Ser Arg Phe Ser Gly
        50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Leu Trp
                85                  90                  95

Thr Phe Gly Gln Gly Thr Lys Val Glu Ile Lys
                100                 105

<210> SEQ ID NO 38
<211> LENGTH: 107
<212> TYPE: PRT
<213> ORGANISM: Artificial Sequence
<220> FEATURE:
<223> OTHER INFORMATION: 5F12.VL.6

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
                20                  25                  30

Ile Ala Trp Tyr Gln His Lys Pro Gly Lys Gly Pro Lys Leu Leu Ile
            35                  40                  45

His Ser Thr Ser Thr Leu Tyr Pro Gly Ile Pro Ser Arg Phe Ser Gly
        50                  55                  60

Ser Gly Ser Gly Lys Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Leu Trp
                85                  90                  95

Thr Phe Gly Gln Gly Thr Lys Val Glu Ile Lys
                100                 105

<210> SEQ ID NO 39
<211> LENGTH: 117
<212> TYPE: PRT
<213> ORGANISM: Artificial Sequence
<220> FEATURE:
<223> OTHER INFORMATION: 5G9.VH.V1

<400> SEQUENCE: 39

```
Glu Val Gln Leu Val Gln Ser Gly Ala Glu Val Lys Lys Pro Gly Ser
1               5                   10                  15

Ser Val Lys Val Ser Cys Lys Thr Ser Gly Tyr Thr Phe Ser Ser Tyr
            20                  25                  30

Thr Ile His Trp Val Arg Gln Ala Pro Gly Gln Gly Leu Glu Trp Ile
        35                  40                  45

Gly Tyr Ile Asn Pro Ser Ser Asp Tyr Thr Ala Tyr Asn Gln Lys Phe
    50                  55                  60

Arg Asp Arg Ala Thr Leu Thr Ala Asp Gln Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Ala Phe Ser Leu Asp Phe Trp Gly Gln Gly Thr Leu
            100                 105                 110

Val Thr Val Ser Ser
        115
```

<210> SEQ ID NO 40
<211> LENGTH: 117
<212> TYPE: PRT
<213> ORGANISM: Artificial Sequence
<220> FEATURE:
<223> OTHER INFORMATION: 5G9.VH.1

<400> SEQUENCE: 40

```
Glu Val Gln Leu Val Gln Ser Gly Ala Glu Val Lys Lys Pro Gly Ser
1               5                   10                  15

Ser Val Lys Val Ser Cys Lys Thr Ser Gly Tyr Thr Phe Ser Ser Tyr
            20                  25                  30

Thr Ile His Trp Val Arg Gln Ala Pro Gly Gln Gly Leu Glu Trp Ile
        35                  40                  45

Gly Tyr Ile Asn Pro Ser Ser Asp Tyr Thr Ala Tyr Asn Gln Lys Phe
    50                  55                  60

Arg Asp Arg Val Thr Leu Thr Ala Asp Gln Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Ala Phe Ser Leu Asp Phe Trp Gly Gln Gly Thr Leu
            100                 105                 110

Val Thr Val Ser Ser
        115
```

<210> SEQ ID NO 41
<211> LENGTH: 117
<212> TYPE: PRT
<213> ORGANISM: Artificial Sequence
<220> FEATURE:
<223> OTHER INFORMATION: 5G9.VH.2

<400> SEQUENCE: 41

```
Glu Val Gln Leu Val Gln Ser Gly Ala Glu Val Lys Lys Pro Gly Ser
1               5                   10                  15
```

-continued

Ser Val Lys Val Ser Cys Lys Thr Ser Gly Tyr Thr Phe Ser Ser Tyr
            20                  25                  30

Thr Ile His Trp Val Arg Gln Ala Pro Gly Gln Gly Leu Glu Trp Ile
            35                  40                  45

Gly Tyr Ile Asn Pro Ser Ser Asp Tyr Thr Ala Tyr Asn Gln Lys Phe
        50                  55                  60

Arg Asp Arg Ala Thr Ile Thr Ala Asp Gln Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Ala Phe Ser Leu Asp Phe Trp Gly Gln Gly Thr Leu
            100                 105                 110

Val Thr Val Ser Ser
            115

<210> SEQ ID NO 42
<211> LENGTH: 117
<212> TYPE: PRT
<213> ORGANISM: Artificial Sequence
<220> FEATURE:
<223> OTHER INFORMATION: 5G9.VH.3

<400> SEQUENCE: 42

Glu Val Gln Leu Val Gln Ser Gly Ala Glu Val Lys Lys Pro Gly Ser
1               5                   10                  15

Ser Val Lys Val Ser Cys Lys Thr Ser Gly Tyr Thr Phe Ser Ser Tyr
            20                  25                  30

Thr Ile His Trp Val Arg Gln Ala Pro Gly Gln Gly Leu Glu Trp Ile
            35                  40                  45

Gly Tyr Ile Asn Pro Ser Ser Asp Tyr Thr Ala Tyr Asn Gln Lys Phe
        50                  55                  60

Arg Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Ala Phe Ser Leu Asp Phe Trp Gly Gln Gly Thr Leu
            100                 105                 110

Val Thr Val Ser Ser
            115

<210> SEQ ID NO 43
<211> LENGTH: 117
<212> TYPE: PRT
<213> ORGANISM: Artificial Sequence
<220> FEATURE:
<223> OTHER INFORMATION: 5G9.VH.4

<400> SEQUENCE: 43

Glu Val Gln Leu Val Gln Ser Gly Ala Glu Val Lys Lys Pro Gly Ser
1               5                   10                  15

Ser Val Lys Val Ser Cys Lys Thr Ser Gly Tyr Thr Phe Ser Ser Tyr
            20                  25                  30

Thr Ile His Trp Val Arg Gln Ala Pro Gly Gln Gly Leu Glu Trp Ile
            35                  40                  45

Gly Tyr Ile Asn Pro Ser Ser Asp Tyr Thr Ala Tyr Asn Gln Lys Phe
        50                  55                  60

Arg Asp Arg Ala Thr Leu Thr Ala Asp Gln Ser Thr Ser Thr Ala Tyr

```
                65                  70                  75                  80
Met Glu Leu Ser Ser Leu Arg Ser Glu Asp Thr Ala Val Tyr Tyr Cys
                    85                  90                  95

Ala Arg Ala Ser Ala Phe Ser Leu Asp Phe Trp Gly Gln Gly Thr Leu
                100                 105                 110

Val Thr Val Ser Ser
        115

<210> SEQ ID NO 44
<211> LENGTH: 117
<212> TYPE: PRT
<213> ORGANISM: Artificial Sequence
<220> FEATURE:
<223> OTHER INFORMATION: 5G9.VH.5

<400> SEQUENCE: 44

Glu Val Gln Leu Val Gln Ser Gly Ala Glu Val Lys Lys Pro Gly Ser
1               5                   10                  15

Ser Val Lys Val Ser Cys Lys Thr Ser Gly Tyr Thr Phe Ser Ser Tyr
                20                  25                  30

Thr Ile His Trp Val Arg Gln Ala Pro Gly Gln Gly Leu Glu Trp Met
            35                  40                  45

Gly Tyr Ile Asn Pro Ser Ser Asp Tyr Thr Ala Tyr Asn Gln Lys Phe
        50                  55                  60

Arg Asp Arg Ala Thr Leu Thr Ala Asp Gln Ser Thr Asn Thr Ala Tyr
65                  70                  75                  80

Met Glu Leu Ser Ser Leu Arg Ser Glu Asp Thr Ala Val Tyr Tyr Cys
                    85                  90                  95

Ala Arg Ala Ser Ala Phe Ser Leu Asp Phe Trp Gly Gln Gly Thr Leu
                100                 105                 110

Val Thr Val Ser Ser
        115

<210> SEQ ID NO 45
<211> LENGTH: 107
<212> TYPE: PRT
<213> ORGANISM: Artificial Sequence
<220> FEATURE:
<223> OTHER INFORMATION: 5G9.VL.V1

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Lys Ala Ser His Asp Ile Asp Arg Tyr
                20                  25                  30

Ile Ala Trp Tyr Gln His Lys Pro Gly Lys Gly Pro Lys Leu Leu Ile
            35                  40                  45

His Tyr Thr Ser Thr Leu Gln Pro Gly Ile Pro Ser Arg Phe Ser Gly
        50                  55                  60

Ser Gly Ser Gly Arg Asp Tyr Thr Leu Thr Ile Ser Ser Leu Gln Pro
65                  70                  75                  80

Glu Asp Val Ala Thr Tyr Tyr Cys Leu Asn Tyr Asp Asn Leu Leu Trp
                    85                  90                  95

Thr Phe Gly Gln Gly Thr Lys Val Glu Ile Lys
                100                 105

<210> SEQ ID NO 46
<211> LENGTH: 107
```

```
<212> TYPE: PRT
<213> ORGANISM: Artificial Sequence
<220> FEATURE:
<223> OTHER INFORMATION: 5G9.VL.1

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ala Ser His Asp Ile Asp Arg Tyr
            20                  25                  30

Ile Ala Trp Tyr Gln Gln Lys Pro Gly Lys Pro Lys Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Val Ala Thr Tyr Tyr Cys Leu Asn Tyr Asp Asn Leu Leu Trp
                85                  90                  95

Thr Phe Gly Gln Gly Thr Lys Val Glu Ile Lys
                100                 105

<210> SEQ ID NO 47
<211> LENGTH: 107
<212> TYPE: PRT
<213> ORGANISM: Artificial Sequence
<220> FEATURE:
<223> OTHER INFORMATION: 5G9.VL.2

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Lys Ala Ser His Asp Ile Asp Arg Tyr
            20                  25                  30

Ile Ala Trp Tyr Gln His Lys Pro Gly Lys Val Pro Lys Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Val Ala Thr Tyr Tyr Cys Leu Asn Tyr Asp Asn Leu Leu Trp
                85                  90                  95

Thr Phe Gly Gln Gly Thr Lys Val Glu Ile Lys
                100                 105

<210> SEQ ID NO 48
<211> LENGTH: 107
<212> TYPE: PRT
<213> ORGANISM: Artificial Sequence
<220> FEATURE:
<223> OTHER INFORMATION: 5G9.VL.3

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Lys Ala Ser His Asp Ile Asp Arg Tyr
            20                  25                  30

Ile Ala Trp Tyr Gln His Lys Pro Gly Lys Gly Pro Lys Leu Leu Ile
        35                  40                  45

Tyr Tyr Thr Ser Thr Leu Gln Pro Gly Ile Pro Ser Arg Phe Ser Gly
```

50                  55                  60
Ser Gly Ser Gly Arg Asp Tyr Thr Leu Thr Ile Ser Ser Leu Gln Pro
 65                  70                  75                  80

Glu Asp Val Ala Thr Tyr Tyr Cys Leu Asn Tyr Asp Asn Leu Leu Trp
                 85                  90                  95

Thr Phe Gly Gln Gly Thr Lys Val Glu Ile Lys
            100                 105

<210> SEQ ID NO 49
<211> LENGTH: 107
<212> TYPE: PRT
<213> ORGANISM: Artificial Sequence
<220> FEATURE:
<223> OTHER INFORMATION: 5G9.VL.4

<400> SEQUENCE: 49

Asp Ile Gln Met Thr Gln Ser Pro Ser Ser Leu Ser Ala Ser Val Gly
 1               5                  10                  15

Asp Arg Val Thr Ile Thr Cys Lys Ala Ser His Asp Ile Asp Arg Tyr
                20                  25                  30

Ile Ala Trp Tyr Gln His Lys Pro Gly Lys Gly Pro Lys Leu Leu Ile
             35                  40                  45

His Tyr Thr Ser Thr Leu Gln Pro Gly Val Pro Ser Arg Phe Ser Gly
         50                  55                  60
Ser Gly Ser Gly Arg Asp Tyr Thr Leu Thr Ile Ser Ser Leu Gln Pro
 65                  70                  75                  80

Glu Asp Val Ala Thr Tyr Tyr Cys Leu Asn Tyr Asp Asn Leu Leu Trp
                 85                  90                  95

Thr Phe Gly Gln Gly Thr Lys Val Glu Ile Lys
            100                 105

<210> SEQ ID NO 50
<211> LENGTH: 107
<212> TYPE: PRT
<213> ORGANISM: Artificial Sequence
<220> FEATURE:
<223> OTHER INFORMATION: 5G9.VL.5

<400> SEQUENCE: 50

Asp Ile Gln Met Thr Gln Ser Pro Ser Ser Leu Ser Ala Ser Val Gly
 1               5                  10                  15

Asp Arg Val Thr Ile Thr Cys Lys Ala Ser His Asp Ile Asp Arg Tyr
                20                  25                  30

Ile Ala Trp Tyr Gln His Lys Pro Gly Lys Gly Pro Lys Leu Leu Ile
             35                  40                  45

His Tyr Thr Ser Thr Leu Gln Pro Gly Ile Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Val Ala Thr Tyr Tyr Cys Leu Asn Tyr Asp Asn Leu Leu Trp
                 85                  90                  95

Thr Phe Gly Gln Gly Thr Lys Val Glu Ile Lys
            100                 105

<210> SEQ ID NO 51
<211> LENGTH: 107
<212> TYPE: PRT
<213> ORGANISM: Artificial Sequence
<220> FEATURE:

<223> OTHER INFORMATION: 5G9.VL.6

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Lys Ala Ser His Asp Ile Asp Arg Tyr
            20                  25                  30

Ile Ala Trp Tyr Gln His Lys Pro Gly Lys Gly Pro Lys Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Phe Thr Leu Thr Ile Ser Ser Leu Gln Pro
65                  70                  75                  80

Glu Asp Val Ala Thr Tyr Tyr Cys Leu Asn Tyr Asp Asn Leu Leu Trp
                85                  90                  95

Thr Phe Gly Gln Gly Thr Lys Val Glu Ile Lys
            100                 105

<210> SEQ ID NO 52
<211> LENGTH: 30
<212> TYPE: PRT
<213> ORGANISM: Artificial Sequence
<220> FEATURE:
<223> OTHER INFORMATION: H-FR1
<220> FEATURE:
<221> NAME/KEY: misc_feature
<222> LOCATION: (24)..(24)
<223> OTHER INFORMATION: Xaa can be Ala or Thr
<220> FEATURE:
<221> NAME/KEY: misc_feature
<222> LOCATION: (30)..(30)
<223> OTHER INFORMATION: Xaa can be Ser or Thr

<400> SEQUENCE: 52

Gln Val Gln Leu Val Gln Ser Gly Ala Glu Val Lys Lys Pro Gly Ser
1               5                   10                  15

Ser Val Lys Val Ser Cys Lys Xaa Ser Gly Gly Thr Phe Xaa
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: H-FR3
<220> FEATURE:
<221> NAME/KEY: misc_feature
<222> LOCATION: (2)..(2)
<223> OTHER INFORMATION: Xaa can be Ala or Val
<220> FEATURE:
<221> NAME/KEY: misc_feature
<222> LOCATION: (8)..(8)
<223> OTHER INFORMATION: Xaa can be Lys or Gln
<220> FEATURE:
<221> NAME/KEY: misc_feature
<222> LOCATION: (11)..(11)
<223> OTHER INFORMATION: Xaa can be Ser or Asn

<400> SEQUENCE: 53

Arg Xaa Thr Ile Thr Ala Asp Xaa Ser Thr Xaa Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 54

```
<211> LENGTH: 15
<212> TYPE: PRT
<213> ORGANISM: Artificial Sequence
<220> FEATURE:
<223> OTHER INFORMATION: L-FR2
<220> FEATURE:
<221> NAME/KEY: misc_feature
<222> LOCATION: (4)..(4)
<223> OTHER INFORMATION: Xaa can be Gln or His
<220> FEATURE:
<221> NAME/KEY: misc_feature
<222> LOCATION: (15)..(15)
<223> OTHER INFORMATION: Xaa can be Tyr or His

<400> SEQUENCE: 54

Trp Tyr Gln Xaa Lys Pro Gly Lys Gly Pro Lys Leu Leu Ile Xaa
1               5                   10                  15

<210> SEQ ID NO 55
<211> LENGTH: 32
<212> TYPE: PRT
<213> ORGANISM: Artificial Sequence
<220> FEATURE:
<223> OTHER INFORMATION: L-FR3
<220> FEATURE:
<221> NAME/KEY: misc_feature
<222> LOCATION: (2)..(2)
<223> OTHER INFORMATION: Xaa can be Ile or Val
<220> FEATURE:
<221> NAME/KEY: misc_feature
<222> LOCATION: (13)..(13)
<223> OTHER INFORMATION: Xaa can be Lys, Thr or Arg
<220> FEATURE:
<221> NAME/KEY: misc_feature
<222> LOCATION: (15)..(15)
<223> OTHER INFORMATION: Xaa can be Tyr or Phe
<220> FEATURE:
<221> NAME/KEY: misc_feature
<222> LOCATION: (17)..(17)
<223> OTHER INFORMATION: Xaa can be Leu or Phe

<400> SEQUENCE: 55

Gly Xaa Pro Ser Arg Phe Ser Gly Ser Gly Ser Gly Xaa Asp Xaa Thr
1               5                   10                  15

Xaa Thr Ile Ser Ser Leu Gln Pro Glu Asp Phe Ala Thr Tyr Tyr Cys
            20                  25                  30

<210> SEQ ID NO 56
<211> LENGTH: 5
<212> TYPE: PRT
<213> ORGANISM: Mus musculus

<400> SEQUENCE: 56

Ser Tyr Thr Met His
1               5

<210> SEQ ID NO 57
<211> LENGTH: 17
<212> TYPE: PRT
<213> ORGANISM: Mus musculus

<400> SEQUENCE: 57

Tyr Ile Asn Pro Ser Ser Gly Tyr Thr Thr Tyr Asn Gln Lys Phe Lys
1               5                   10                  15

Asp

<210> SEQ ID NO 58
<211> LENGTH: 8
<212> TYPE: PRT
```

-continued

<213> ORGANISM: Mus musculus

<400> SEQUENCE: 58

Ala Ser Ala Tyr Ser Leu Asp Tyr
1               5

<210> SEQ ID NO 59
<211> LENGTH: 11
<212> TYPE: PRT
<213> ORGANISM: Mus musculus

<400> SEQUENCE: 59

Lys Ala Ser His Asp Ile Asp Arg Tyr Ile Ala
1               5                   10

<210> SEQ ID NO 60
<211> LENGTH: 7
<212> TYPE: PRT
<213> ORGANISM: Mus musculus

<400> SEQUENCE: 60

Tyr Thr Ser Thr Leu Gln Pro
1               5

<210> SEQ ID NO 61
<211> LENGTH: 9
<212> TYPE: PRT
<213> ORGANISM: Mus musculus

<400> SEQUENCE: 61

Leu Lys Tyr Asp Asn Leu Leu Trp Thr
1               5

<210> SEQ ID NO 62
<211> LENGTH: 5
<212> TYPE: PRT
<213> ORGANISM: Mus musculus

<400> SEQUENCE: 62

Ser Tyr Thr Ile His
1               5

<210> SEQ ID NO 63
<211> LENGTH: 17
<212> TYPE: PRT
<213> ORGANISM: Mus musculus

<400> SEQUENCE: 63

Tyr Ile Asn Pro Ser Ser Gly Tyr Thr Thr Tyr Asn Gln Arg Phe Lys
1               5                   10                  15

Asp

<210> SEQ ID NO 64
<211> LENGTH: 8
<212> TYPE: PRT
<213> ORGANISM: Mus musculus

<400> SEQUENCE: 64

Ala Ser Ala Tyr Ser Leu Asp Tyr
1               5

<210> SEQ ID NO 65
<211> LENGTH: 11
<212> TYPE: PRT

<213> ORGANISM: Mus musculus

<400> SEQUENCE: 65

Lys Ala Ser Gln Asp Ile Asp Arg Tyr Ile Ala
1               5                   10

<210> SEQ ID NO 66
<211> LENGTH: 7
<212> TYPE: PRT
<213> ORGANISM: Mus musculus

<400> SEQUENCE: 66

Tyr Thr Ser Thr Leu Gln Pro
1               5

<210> SEQ ID NO 67
<211> LENGTH: 9
<212> TYPE: PRT
<213> ORGANISM: Mus musculus

<400> SEQUENCE: 67

Leu Lys Tyr Asp Asn Leu Leu Trp Thr
1               5

<210> SEQ ID NO 68
<211> LENGTH: 5
<212> TYPE: PRT
<213> ORGANISM: Mus musculus

<400> SEQUENCE: 68

Ser Tyr Thr Met His
1               5

<210> SEQ ID NO 69
<211> LENGTH: 17
<212> TYPE: PRT
<213> ORGANISM: Mus musculus

<400> SEQUENCE: 69

Tyr Ile Asn Pro Ser Ser Ala Tyr Thr Asn Tyr Asn Gln Lys Phe Lys
1               5                   10                  15

Asp

<210> SEQ ID NO 70
<211> LENGTH: 8
<212> TYPE: PRT
<213> ORGANISM: Mus musculus

<400> SEQUENCE: 70

Ala Ser Ala Tyr Ser Leu Asp Tyr
1               5

<210> SEQ ID NO 71
<211> LENGTH: 11
<212> TYPE: PRT
<213> ORGANISM: Mus musculus

<400> SEQUENCE: 71

Lys Ala Ser Gln Asp Ile Asn Lys Tyr Ile Ala
1               5                   10

<210> SEQ ID NO 72
<211> LENGTH: 7
<212> TYPE: PRT

<213> ORGANISM: Mus musculus

<400> SEQUENCE: 72

Ser Thr Ser Thr Leu Tyr Pro
1               5

<210> SEQ ID NO 73
<211> LENGTH: 9
<212> TYPE: PRT
<213> ORGANISM: Mus musculus

<400> SEQUENCE: 73

Leu Gln Tyr Asp Asn Leu Leu Trp Thr
1               5

<210> SEQ ID NO 74
<211> LENGTH: 5
<212> TYPE: PRT
<213> ORGANISM: Mus musculus

<400> SEQUENCE: 74

Ser Tyr Thr Met His
1               5

<210> SEQ ID NO 75
<211> LENGTH: 17
<212> TYPE: PRT
<213> ORGANISM: Mus musculus

<400> SEQUENCE: 75

Tyr Ile Asn Pro Ser Ser Ser Tyr Thr Asn Tyr Asn Gln Asn Phe Lys
1               5                   10                  15

Asp

<210> SEQ ID NO 76
<211> LENGTH: 8
<212> TYPE: PRT
<213> ORGANISM: Mus musculus

<400> SEQUENCE: 76

Ala Ser Ser Tyr Ser Leu Asp Tyr
1               5

<210> SEQ ID NO 77
<211> LENGTH: 11
<212> TYPE: PRT
<213> ORGANISM: Mus musculus

<400> SEQUENCE: 77

Lys Ala Ser Gln Asp Ile Asn Lys Tyr Ile Ala
1               5                   10

<210> SEQ ID NO 78
<211> LENGTH: 7
<212> TYPE: PRT
<213> ORGANISM: Mus musculus

<400> SEQUENCE: 78

Ser Thr Ser Thr Leu Tyr Pro
1               5

<210> SEQ ID NO 79
<211> LENGTH: 9
<212> TYPE: PRT

<213> ORGANISM: Mus musculus

<400> SEQUENCE: 79

Leu Gln Tyr Asp Asn Leu Leu Trp Thr
1               5

<210> SEQ ID NO 80
<211> LENGTH: 5
<212> TYPE: PRT
<213> ORGANISM: Mus musculus

<400> SEQUENCE: 80

Ser Tyr Thr Ile His
1               5

<210> SEQ ID NO 81
<211> LENGTH: 17
<212> TYPE: PRT
<213> ORGANISM: Mus musculus

<400> SEQUENCE: 81

Tyr Ile Asn Pro Ser Ser Asp Tyr Thr Ala Tyr Asn Gln Lys Phe Arg
1               5                   10                  15

Asp

<210> SEQ ID NO 82
<211> LENGTH: 8
<212> TYPE: PRT
<213> ORGANISM: Mus musculus

<400> SEQUENCE: 82

Ala Ser Ala Phe Ser Leu Asp Phe
1               5

<210> SEQ ID NO 83
<211> LENGTH: 11
<212> TYPE: PRT
<213> ORGANISM: Mus musculus

<400> SEQUENCE: 83

Lys Ala Ser His Asp Ile Asp Arg Tyr Ile Ala
1               5                   10

<210> SEQ ID NO 84
<211> LENGTH: 7
<212> TYPE: PRT
<213> ORGANISM: Mus musculus

<400> SEQUENCE: 84

Tyr Thr Ser Thr Leu Gln Pro
1               5

<210> SEQ ID NO 85
<211> LENGTH: 9
<212> TYPE: PRT
<213> ORGANISM: Mus musculus

<400> SEQUENCE: 85

Leu Asn Tyr Asp Asn Leu Leu Trp Thr
1               5

<210> SEQ ID NO 86
<211> LENGTH: 5
<212> TYPE: PRT

```
<213> ORGANISM: Artificial Sequence
<220> FEATURE:
<223> OTHER INFORMATION: 5F12.VH.V1 CDR-H1

<400> SEQUENCE: 86

Ser Tyr Thr Met His
1               5

<210> SEQ ID NO 87
<211> LENGTH: 17
<212> TYPE: PRT
<213> ORGANISM: Artificial Sequence
<220> FEATURE:
<223> OTHER INFORMATION: 5F12.VH.V1 CDR-H2

<400> SEQUENCE: 87

Tyr Ile Asn Pro Ser Ser Ser Tyr Thr Asn Tyr Asn Gln Asn Phe Lys
1               5                   10                  15

Asp

<210> SEQ ID NO 88
<211> LENGTH: 8
<212> TYPE: PRT
<213> ORGANISM: Artificial Sequence
<220> FEATURE:
<223> OTHER INFORMATION: 5F12.VH.V1 CDR-H3

<400> SEQUENCE: 88

Ala Ser Ser Tyr Ser Leu Asp Tyr
1               5

<210> SEQ ID NO 89
<211> LENGTH: 5
<212> TYPE: PRT
<213> ORGANISM: Artificial Sequence
<220> FEATURE:
<223> OTHER INFORMATION: 5F12.VH.1 CDR-H1

<400> SEQUENCE: 89

Ser Tyr Thr Met His
1               5

<210> SEQ ID NO 90
<211> LENGTH: 17
<212> TYPE: PRT
<213> ORGANISM: Artificial Sequence
<220> FEATURE:
<223> OTHER INFORMATION: 5F12.VH.1 CDR-H2

<400> SEQUENCE: 90

Tyr Ile Asn Pro Ser Ser Ser Tyr Thr Asn Tyr Asn Gln Asn Phe Lys
1               5                   10                  15

Asp

<210> SEQ ID NO 91
<211> LENGTH: 8
<212> TYPE: PRT
<213> ORGANISM: Artificial Sequence
<220> FEATURE:
<223> OTHER INFORMATION: 5F12.VH.1 CDR-H3

<400> SEQUENCE: 91

Ala Ser Ser Tyr Ser Leu Asp Tyr
1               5
```

```
<210> SEQ ID NO 92
<211> LENGTH: 5
<212> TYPE: PRT
<213> ORGANISM: Artificial Sequence
<220> FEATURE:
<223> OTHER INFORMATION: 5F12.VH.2 CDR-H1

<400> SEQUENCE: 92

Ser Tyr Thr Met His
1               5

<210> SEQ ID NO 93
<211> LENGTH: 17
<212> TYPE: PRT
<213> ORGANISM: Artificial Sequence
<220> FEATURE:
<223> OTHER INFORMATION: 5F12.VH.2 CDR-H2

<400> SEQUENCE: 93

Tyr Ile Asn Pro Ser Ser Ser Tyr Thr Asn Tyr Asn Gln Asn Phe Lys
1               5                   10                  15

Asp

<210> SEQ ID NO 94
<211> LENGTH: 8
<212> TYPE: PRT
<213> ORGANISM: Artificial Sequence
<220> FEATURE:
<223> OTHER INFORMATION: 5F12.VH.2 CDR-H3

<400> SEQUENCE: 94

Ala Ser Ser Tyr Ser Leu Asp Tyr
1               5

<210> SEQ ID NO 95
<211> LENGTH: 5
<212> TYPE: PRT
<213> ORGANISM: Artificial Sequence
<220> FEATURE:
<223> OTHER INFORMATION: 5F12.VH.3 CDR-H1

<400> SEQUENCE: 95

Ser Tyr Thr Met His
1               5

<210> SEQ ID NO 96
<211> LENGTH: 17
<212> TYPE: PRT
<213> ORGANISM: Artificial Sequence
<220> FEATURE:
<223> OTHER INFORMATION: 5F12.VH.3 CDR-H2

<400> SEQUENCE: 96

Tyr Ile Asn Pro Ser Ser Ser Tyr Thr Asn Tyr Asn Gln Asn Phe Lys
1               5                   10                  15

Asp

<210> SEQ ID NO 97
<211> LENGTH: 8
<212> TYPE: PRT
<213> ORGANISM: Artificial Sequence
<220> FEATURE:
<223> OTHER INFORMATION: 5F12.VH.3 CDR-H3

<400> SEQUENCE: 97

Ala Ser Ser Tyr Ser Leu Asp Tyr
```

```
1               5

<210> SEQ ID NO 98
<211> LENGTH: 5
<212> TYPE: PRT
<213> ORGANISM: Artificial Sequence
<220> FEATURE:
<223> OTHER INFORMATION: 5F12.VH.4 CDR-H1

<400> SEQUENCE: 98

Ser Tyr Thr Met His
1               5

<210> SEQ ID NO 99
<211> LENGTH: 17
<212> TYPE: PRT
<213> ORGANISM: Artificial Sequence
<220> FEATURE:
<223> OTHER INFORMATION: 5F12.VH.4 CDR-H2

<400> SEQUENCE: 99

Tyr Ile Asn Pro Ser Ser Ser Tyr Thr Asn Tyr Asn Gln Asn Phe Lys
1               5                   10                  15

Asp

<210> SEQ ID NO 100
<211> LENGTH: 8
<212> TYPE: PRT
<213> ORGANISM: Artificial Sequence
<220> FEATURE:
<223> OTHER INFORMATION: 5F12.VH.4 CDR-H3

<400> SEQUENCE: 100

Ala Ser Ser Tyr Ser Leu Asp Tyr
1               5

<210> SEQ ID NO 101
<211> LENGTH: 11
<212> TYPE: PRT
<213> ORGANISM: Artificial Sequence
<220> FEATURE:
<223> OTHER INFORMATION: 5F12.VL.V1 CDR-L1

<400> SEQUENCE: 101

Lys Ala Ser Gln Asp Ile Asn Lys Tyr Ile Ala
1               5                   10

<210> SEQ ID NO 102
<211> LENGTH: 7
<212> TYPE: PRT
<213> ORGANISM: Artificial Sequence
<220> FEATURE:
<223> OTHER INFORMATION: 5F12.VL.V1 CDR-L2

<400> SEQUENCE: 102

Ser Thr Ser Thr Leu Tyr Pro
1               5

<210> SEQ ID NO 103
<211> LENGTH: 9
<212> TYPE: PRT
<213> ORGANISM: Artificial Sequence
<220> FEATURE:
<223> OTHER INFORMATION: 5F12.VL.V1 CDR-L3

<400> SEQUENCE: 103
```

Leu Gln Tyr Asp Asn Leu Leu Trp Thr
1               5

<210> SEQ ID NO 104
<211> LENGTH: 11
<212> TYPE: PRT
<213> ORGANISM: Artificial Sequence
<220> FEATURE:
<223> OTHER INFORMATION: 5F12.VL.1 CDR-L1

<400> SEQUENCE: 104

Lys Ala Ser Gln Asp Ile Asn Lys Tyr Ile Ala
1               5                   10

<210> SEQ ID NO 105
<211> LENGTH: 7
<212> TYPE: PRT
<213> ORGANISM: Artificial Sequence
<220> FEATURE:
<223> OTHER INFORMATION: 5F12.VL.1 CDR-L2

<400> SEQUENCE: 105

Ser Thr Ser Thr Leu Tyr Pro
1               5

<210> SEQ ID NO 106
<211> LENGTH: 9
<212> TYPE: PRT
<213> ORGANISM: Artificial Sequence
<220> FEATURE:
<223> OTHER INFORMATION: 5F12.VL.1 CDR-L3

<400> SEQUENCE: 106

Leu Gln Tyr Asp Asn Leu Leu Trp Thr
1               5

<210> SEQ ID NO 107
<211> LENGTH: 11
<212> TYPE: PRT
<213> ORGANISM: Artificial Sequence
<220> FEATURE:
<223> OTHER INFORMATION: 5F12.VL.2 CDR-L1

<400> SEQUENCE: 107

Lys Ala Ser Gln Asp Ile Asn Lys Tyr Ile Ala
1               5                   10

<210> SEQ ID NO 108
<211> LENGTH: 7
<212> TYPE: PRT
<213> ORGANISM: Artificial Sequence
<220> FEATURE:
<223> OTHER INFORMATION: 5F12.VL.2 CDR-L2

<400> SEQUENCE: 108

Ser Thr Ser Thr Leu Tyr Pro
1               5

<210> SEQ ID NO 109
<211> LENGTH: 9
<212> TYPE: PRT
<213> ORGANISM: Artificial Sequence
<220> FEATURE:
<223> OTHER INFORMATION: 5F12.VL.2 CDR-L3

<400> SEQUENCE: 109

Leu Gln Tyr Asp Asn Leu Leu Trp Thr

```
1               5

<210> SEQ ID NO 110
<211> LENGTH: 11
<212> TYPE: PRT
<213> ORGANISM: Artificial Sequence
<220> FEATURE:
<223> OTHER INFORMATION: 5F12.VL.3 CDR-L1

<400> SEQUENCE: 110

Lys Ala Ser Gln Asp Ile Asn Lys Tyr Ile Ala
1               5                   10

<210> SEQ ID NO 111
<211> LENGTH: 7
<212> TYPE: PRT
<213> ORGANISM: Artificial Sequence
<220> FEATURE:
<223> OTHER INFORMATION: 5F12.VL.3 CDR-L2

<400> SEQUENCE: 111

Ser Thr Ser Thr Leu Tyr Pro
1               5

<210> SEQ ID NO 112
<211> LENGTH: 9
<212> TYPE: PRT
<213> ORGANISM: Artificial Sequence
<220> FEATURE:
<223> OTHER INFORMATION: 5F12.VL.3 CDR-L3

<400> SEQUENCE: 112

Leu Gln Tyr Asp Asn Leu Leu Trp Thr
1               5

<210> SEQ ID NO 113
<211> LENGTH: 11
<212> TYPE: PRT
<213> ORGANISM: Artificial Sequence
<220> FEATURE:
<223> OTHER INFORMATION: 5F12.VL.4 CDR-L1

<400> SEQUENCE: 113

Lys Ala Ser Gln Asp Ile Asn Lys Tyr Ile Ala
1               5                   10

<210> SEQ ID NO 114
<211> LENGTH: 7
<212> TYPE: PRT
<213> ORGANISM: Artificial Sequence
<220> FEATURE:
<223> OTHER INFORMATION: 5F12.VL.4 CDR-L2

<400> SEQUENCE: 114

Ser Thr Ser Thr Leu Tyr Pro
1               5

<210> SEQ ID NO 115
<211> LENGTH: 9
<212> TYPE: PRT
<213> ORGANISM: Artificial Sequence
<220> FEATURE:
<223> OTHER INFORMATION: 5F12.VL.4 CDR-L3

<400> SEQUENCE: 115

Leu Gln Tyr Asp Asn Leu Leu Trp Thr
1               5
```

<210> SEQ ID NO 116
<211> LENGTH: 11
<212> TYPE: PRT
<213> ORGANISM: Artificial Sequence
<220> FEATURE:
<223> OTHER INFORMATION: 5F12.VL.5 CDR-L1

<400> SEQUENCE: 116

Lys Ala Ser Gln Asp Ile Asn Lys Tyr Ile Ala
1               5                   10

<210> SEQ ID NO 117
<211> LENGTH: 7
<212> TYPE: PRT
<213> ORGANISM: Artificial Sequence
<220> FEATURE:
<223> OTHER INFORMATION: 5F12.VL.5 CDR-L2

<400> SEQUENCE: 117

Ser Thr Ser Thr Leu Tyr Pro
1               5

<210> SEQ ID NO 118
<211> LENGTH: 9
<212> TYPE: PRT
<213> ORGANISM: Artificial Sequence
<220> FEATURE:
<223> OTHER INFORMATION: 5F12.VL.5 CDR-L3

<400> SEQUENCE: 118

Leu Gln Tyr Asp Asn Leu Leu Trp Thr
1               5

<210> SEQ ID NO 119
<211> LENGTH: 11
<212> TYPE: PRT
<213> ORGANISM: Artificial Sequence
<220> FEATURE:
<223> OTHER INFORMATION: 5F12.VL.6 CDR-L1

<400> SEQUENCE: 119

Lys Ala Ser Gln Asp Ile Asn Lys Tyr Ile Ala
1               5                   10

<210> SEQ ID NO 120
<211> LENGTH: 7
<212> TYPE: PRT
<213> ORGANISM: Artificial Sequence
<220> FEATURE:
<223> OTHER INFORMATION: 5F12.VL.6 CDR-L2

<400> SEQUENCE: 120

Ser Thr Ser Thr Leu Tyr Pro
1               5

<210> SEQ ID NO 121
<211> LENGTH: 9
<212> TYPE: PRT
<213> ORGANISM: Artificial Sequence
<220> FEATURE:
<223> OTHER INFORMATION: 5F12.VL.6 CDR-L3

<400> SEQUENCE: 121

Leu Gln Tyr Asp Asn Leu Leu Trp Thr
1               5

```
<210> SEQ ID NO 122
<211> LENGTH: 5
<212> TYPE: PRT
<213> ORGANISM: Artificial Sequence
<220> FEATURE:
<223> OTHER INFORMATION: 5G9.VH.V1 CDR-H1

<400> SEQUENCE: 122

Ser Tyr Thr Ile His
1               5

<210> SEQ ID NO 123
<211> LENGTH: 17
<212> TYPE: PRT
<213> ORGANISM: Artificial Sequence
<220> FEATURE:
<223> OTHER INFORMATION: 5G9.VH.V1 CDR-H2

<400> SEQUENCE: 123

Tyr Ile Asn Pro Ser Ser Asp Tyr Thr Ala Tyr Asn Gln Lys Phe Arg
1               5                   10                  15

Asp

<210> SEQ ID NO 124
<211> LENGTH: 8
<212> TYPE: PRT
<213> ORGANISM: Artificial Sequence
<220> FEATURE:
<223> OTHER INFORMATION: 5G9.VH.V1 CDR-H3

<400> SEQUENCE: 124

Ala Ser Ala Phe Ser Leu Asp Phe
1               5

<210> SEQ ID NO 125
<211> LENGTH: 5
<212> TYPE: PRT
<213> ORGANISM: Artificial Sequence
<220> FEATURE:
<223> OTHER INFORMATION: 5G9.VH.1 CDR-H1

<400> SEQUENCE: 125

Ser Tyr Thr Ile His
1               5

<210> SEQ ID NO 126
<211> LENGTH: 17
<212> TYPE: PRT
<213> ORGANISM: Artificial Sequence
<220> FEATURE:
<223> OTHER INFORMATION: 5G9.VH.1 CDR-H2

<400> SEQUENCE: 126

Tyr Ile Asn Pro Ser Ser Asp Tyr Thr Ala Tyr Asn Gln Lys Phe Arg
1               5                   10                  15

Asp

<210> SEQ ID NO 127
<211> LENGTH: 8
<212> TYPE: PRT
<213> ORGANISM: Artificial Sequence
<220> FEATURE:
<223> OTHER INFORMATION: 5G9.VH.1 CDR-H3

<400> SEQUENCE: 127
```

Ala Ser Ala Phe Ser Leu Asp Phe
1               5

<210> SEQ ID NO 128
<211> LENGTH: 5
<212> TYPE: PRT
<213> ORGANISM: Artificial Sequence
<220> FEATURE:
<223> OTHER INFORMATION: 5G9.VH.2 CDR-H1

<400> SEQUENCE: 128

Ser Tyr Thr Ile His
1               5

<210> SEQ ID NO 129
<211> LENGTH: 17
<212> TYPE: PRT
<213> ORGANISM: Artificial Sequence
<220> FEATURE:
<223> OTHER INFORMATION: 5G9.VH.2 CDR-H2

<400> SEQUENCE: 129

Tyr Ile Asn Pro Ser Ser Asp Tyr Thr Ala Tyr Asn Gln Lys Phe Arg
1               5                   10                  15
Asp

<210> SEQ ID NO 130
<211> LENGTH: 8
<212> TYPE: PRT
<213> ORGANISM: Artificial Sequence
<220> FEATURE:
<223> OTHER INFORMATION: 5G9.VH.2 CDR-H3

<400> SEQUENCE: 130

Ala Ser Ala Phe Ser Leu Asp Phe
1               5

<210> SEQ ID NO 131
<211> LENGTH: 5
<212> TYPE: PRT
<213> ORGANISM: Artificial Sequence
<220> FEATURE:
<223> OTHER INFORMATION: 5G9.VH.3 CDR-H1

<400> SEQUENCE: 131

Ser Tyr Thr Ile His
1               5

<210> SEQ ID NO 132
<211> LENGTH: 17
<212> TYPE: PRT
<213> ORGANISM: Artificial Sequence
<220> FEATURE:
<223> OTHER INFORMATION: 5G9.VH.3 CDR-H2

<400> SEQUENCE: 132

Tyr Ile Asn Pro Ser Ser Asp Tyr Thr Ala Tyr Asn Gln Lys Phe Arg
1               5                   10                  15
Asp

<210> SEQ ID NO 133
<211> LENGTH: 8
<212> TYPE: PRT
<213> ORGANISM: Artificial Sequence
<220> FEATURE:
<223> OTHER INFORMATION: 5G9.VH.3 CDR-H3

```
<400> SEQUENCE: 133

Ala Ser Ala Phe Ser Leu Asp Phe
1               5

<210> SEQ ID NO 134
<211> LENGTH: 5
<212> TYPE: PRT
<213> ORGANISM: Artificial Sequence
<220> FEATURE:
<223> OTHER INFORMATION: 5G9.VH.4 CDR-H1

<400> SEQUENCE: 134

Ser Tyr Thr Ile His
1               5

<210> SEQ ID NO 135
<211> LENGTH: 17
<212> TYPE: PRT
<213> ORGANISM: Artificial Sequence
<220> FEATURE:
<223> OTHER INFORMATION: 5G9.VH.4 CDR-H2

<400> SEQUENCE: 135

Tyr Ile Asn Pro Ser Ser Asp Tyr Thr Ala Tyr Asn Gln Lys Phe Arg
1               5                   10                  15

Asp

<210> SEQ ID NO 136
<211> LENGTH: 8
<212> TYPE: PRT
<213> ORGANISM: Artificial Sequence
<220> FEATURE:
<223> OTHER INFORMATION: 5G9.VH.4 CDR-H3

<400> SEQUENCE: 136

Ala Ser Ala Phe Ser Leu Asp Phe
1               5

<210> SEQ ID NO 137
<211> LENGTH: 5
<212> TYPE: PRT
<213> ORGANISM: Artificial Sequence
<220> FEATURE:
<223> OTHER INFORMATION: 5G9.VH.5 CDR-H1

<400> SEQUENCE: 137

Ser Tyr Thr Ile His
1               5

<210> SEQ ID NO 138
<211> LENGTH: 17
<212> TYPE: PRT
<213> ORGANISM: Artificial Sequence
<220> FEATURE:
<223> OTHER INFORMATION: 5G9.VH.5 CDR-H2

<400> SEQUENCE: 138

Tyr Ile Asn Pro Ser Ser Asp Tyr Thr Ala Tyr Asn Gln Lys Phe Arg
1               5                   10                  15

Asp

<210> SEQ ID NO 139
<211> LENGTH: 8
<212> TYPE: PRT
```

```
<213> ORGANISM: Artificial Sequence
<220> FEATURE:
<223> OTHER INFORMATION: 5G9.VH.5 CDR-H3

<400> SEQUENCE: 139

Ala Ser Ala Phe Ser Leu Asp Phe
1               5

<210> SEQ ID NO 140
<211> LENGTH: 11
<212> TYPE: PRT
<213> ORGANISM: Artificial Sequence
<220> FEATURE:
<223> OTHER INFORMATION: 5G9.VL.V1 CDR-L1

<400> SEQUENCE: 140

Lys Ala Ser His Asp Ile Asp Arg Tyr Ile Ala
1               5                   10

<210> SEQ ID NO 141
<211> LENGTH: 7
<212> TYPE: PRT
<213> ORGANISM: Artificial Sequence
<220> FEATURE:
<223> OTHER INFORMATION: 5G9.VL.V1 CDR-L2

<400> SEQUENCE: 141

Tyr Thr Ser Thr Leu Gln Pro
1               5

<210> SEQ ID NO 142
<211> LENGTH: 9
<212> TYPE: PRT
<213> ORGANISM: Artificial Sequence
<220> FEATURE:
<223> OTHER INFORMATION: 5G9.VL.V1 CDR-L3

<400> SEQUENCE: 142

Leu Asn Tyr Asp Asn Leu Leu Trp Thr
1               5

<210> SEQ ID NO 143
<211> LENGTH: 11
<212> TYPE: PRT
<213> ORGANISM: Artificial Sequence
<220> FEATURE:
<223> OTHER INFORMATION: 5G9.VL.1 CDR-L1

<400> SEQUENCE: 143

Lys Ala Ser His Asp Ile Asp Arg Tyr Ile Ala
1               5                   10

<210> SEQ ID NO 144
<211> LENGTH: 7
<212> TYPE: PRT
<213> ORGANISM: Artificial Sequence
<220> FEATURE:
<223> OTHER INFORMATION: 5G9.VL.1 CDR-L2

<400> SEQUENCE: 144

Tyr Thr Ser Thr Leu Gln Pro
1               5

<210> SEQ ID NO 145
<211> LENGTH: 9
<212> TYPE: PRT
<213> ORGANISM: Artificial Sequence
```

<220> FEATURE:
<223> OTHER INFORMATION: 5G9.VL.1 CDR-L3

<400> SEQUENCE: 145

Leu Asn Tyr Asp Asn Leu Leu Trp Thr
1               5

<210> SEQ ID NO 146
<211> LENGTH: 11
<212> TYPE: PRT
<213> ORGANISM: Artificial Sequence
<220> FEATURE:
<223> OTHER INFORMATION: 5G9.VL.2 CDR-L1

<400> SEQUENCE: 146

Lys Ala Ser His Asp Ile Asp Arg Tyr Ile Ala
1               5                   10

<210> SEQ ID NO 147
<211> LENGTH: 7
<212> TYPE: PRT
<213> ORGANISM: Artificial Sequence
<220> FEATURE:
<223> OTHER INFORMATION: 5G9.VL.2 CDR-L2

<400> SEQUENCE: 147

Tyr Thr Ser Thr Leu Gln Pro
1               5

<210> SEQ ID NO 148
<211> LENGTH: 9
<212> TYPE: PRT
<213> ORGANISM: Artificial Sequence
<220> FEATURE:
<223> OTHER INFORMATION: 5G9.VL.2 CDR-L3

<400> SEQUENCE: 148

Leu Asn Tyr Asp Asn Leu Leu Trp Thr
1               5

<210> SEQ ID NO 149
<211> LENGTH: 11
<212> TYPE: PRT
<213> ORGANISM: Artificial Sequence
<220> FEATURE:
<223> OTHER INFORMATION: 5G9.VL.3 CDR-L1

<400> SEQUENCE: 149

Lys Ala Ser His Asp Ile Asp Arg Tyr Ile Ala
1               5                   10

<210> SEQ ID NO 150
<211> LENGTH: 7
<212> TYPE: PRT
<213> ORGANISM: Artificial Sequence
<220> FEATURE:
<223> OTHER INFORMATION: 5G9.VL.3 CDR-L2

<400> SEQUENCE: 150

Tyr Thr Ser Thr Leu Gln Pro
1               5

<210> SEQ ID NO 151
<211> LENGTH: 9
<212> TYPE: PRT
<213> ORGANISM: Artificial Sequence
<220> FEATURE:

<223> OTHER INFORMATION: 5G9.VL.3 CDR-L3

<400> SEQUENCE: 151

Leu Asn Tyr Asp Asn Leu Leu Trp Thr
1               5

<210> SEQ ID NO 152
<211> LENGTH: 11
<212> TYPE: PRT
<213> ORGANISM: Artificial Sequence
<220> FEATURE:
<223> OTHER INFORMATION: 5G9.VL.4 CDR-L1

<400> SEQUENCE: 152

Lys Ala Ser His Asp Ile Asp Arg Tyr Ile Ala
1               5                   10

<210> SEQ ID NO 153
<211> LENGTH: 7
<212> TYPE: PRT
<213> ORGANISM: Artificial Sequence
<220> FEATURE:
<223> OTHER INFORMATION: 5G9.VL.4 CDR-L2

<400> SEQUENCE: 153

Tyr Thr Ser Thr Leu Gln Pro
1               5

<210> SEQ ID NO 154
<211> LENGTH: 9
<212> TYPE: PRT
<213> ORGANISM: Artificial Sequence
<220> FEATURE:
<223> OTHER INFORMATION: 5G9.VL.4 CDR-L3

<400> SEQUENCE: 154

Leu Asn Tyr Asp Asn Leu Leu Trp Thr
1               5

<210> SEQ ID NO 155
<211> LENGTH: 11
<212> TYPE: PRT
<213> ORGANISM: Artificial Sequence
<220> FEATURE:
<223> OTHER INFORMATION: 5G9.VL.5 CDR-L1

<400> SEQUENCE: 155

Lys Ala Ser His Asp Ile Asp Arg Tyr Ile Ala
1               5                   10

<210> SEQ ID NO 156
<211> LENGTH: 7
<212> TYPE: PRT
<213> ORGANISM: Artificial Sequence
<220> FEATURE:
<223> OTHER INFORMATION: 5G9.VL.5 CDR-L2

<400> SEQUENCE: 156

Tyr Thr Ser Thr Leu Gln Pro
1               5

<210> SEQ ID NO 157
<211> LENGTH: 9
<212> TYPE: PRT
<213> ORGANISM: Artificial Sequence
<220> FEATURE:
<223> OTHER INFORMATION: 5G9.VL.5 CDR-L3

<400> SEQUENCE: 157

Leu Asn Tyr Asp Asn Leu Leu Trp Thr
1               5

<210> SEQ ID NO 158
<211> LENGTH: 11
<212> TYPE: PRT
<213> ORGANISM: Artificial Sequence
<220> FEATURE:
<223> OTHER INFORMATION: 5G9.VL.6 CDR-L1

<400> SEQUENCE: 158

Lys Ala Ser His Asp Ile Asp Arg Tyr Ile Ala
1               5                   10

<210> SEQ ID NO 159
<211> LENGTH: 7
<212> TYPE: PRT
<213> ORGANISM: Artificial Sequence
<220> FEATURE:
<223> OTHER INFORMATION: 5G9.VL.6 CDR-L2

<400> SEQUENCE: 159

Tyr Thr Ser Thr Leu Gln Pro
1               5

<210> SEQ ID NO 160
<211> LENGTH: 9
<212> TYPE: PRT
<213> ORGANISM: Artificial Sequence
<220> FEATURE:
<223> OTHER INFORMATION: 5G9.VL.6 CDR-L3

<400> SEQUENCE: 160

Leu Asn Tyr Asp Asn Leu Leu Trp Thr
1               5

<210> SEQ ID NO 161
<211> LENGTH: 30
<212> TYPE: PRT
<213> ORGANISM: Homo sapiens

<400> SEQUENCE: 161

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 162
<211> LENGTH: 14
<212> TYPE: PRT
<213> ORGANISM: Homo sapiens

<400> SEQUENCE: 162

Trp Val Arg Gln Ala Pro Gly Gln Gly Leu Glu Trp Met Gly
1               5                   10

<210> SEQ ID NO 163
<211> LENGTH: 32
<212> TYPE: PRT
<213> ORGANISM: Homo sapiens

<400> SEQUENCE: 163

Arg Val Thr Met Thr Arg Asp Thr Ser Thr Ser Thr Val Tyr Met Glu

```
                1               5                  10                  15
Leu Ser Ser Leu Arg Ser Glu Asp Thr Ala Val Tyr Tyr Cys Ala Arg
                        20                  25                  30
```

<210> SEQ ID NO 164
<211> LENGTH: 23
<212> TYPE: PRT
<213> ORGANISM: Homo sapiens

<400> SEQUENCE: 164

```
Asp Ile Gln Met Thr Gln Ser Pro Ser Ser Leu Ser Ala Ser Val Gly
1               5                  10                  15
Asp Arg Val Thr Ile Thr Cys
                        20
```

<210> SEQ ID NO 165
<211> LENGTH: 15
<212> TYPE: PRT
<213> ORGANISM: Homo sapiens

<400> SEQUENCE: 165

```
Trp Tyr Gln Gln Lys Pro Gly Lys Gly Pro Lys Leu Leu Ile Tyr
1               5                  10                  15
```

<210> SEQ ID NO 166
<211> LENGTH: 32
<212> TYPE: PRT
<213> ORGANISM: Homo sapiens

<400> SEQUENCE: 166

```
Gly Val Pro Ser Arg Phe Ser Gly Ser Gly Ser Gly Thr Asp Phe Thr
1               5                  10                  15
Leu Thr Ile Ser Ser Leu Gln Pro Glu Asp Phe Ala Thr Tyr Tyr Cys
                        20                  25                  30
```